.

US008536354B2

(12) United States Patent
Hormann et al.

(10) Patent No.: US 8,536,354 B2
(45) Date of Patent: Sep. 17, 2013

(54) STEROIDAL LIGANDS AND THEIR USE IN GENE SWITCH MODULATION

(75) Inventors: Robert E. Hormann, Melrose Park, PA (US); Silvia Lapenna, Leghorn (IT); Laurence Neil Dinan, Blandform Forum (GB)

(73) Assignee: Intrexon Corporation, Blacksburg, VA (US)

( * ) Notice: Subject to any disclaimer, the term of this patent is extended or adjusted under 35 U.S.C. 154(b) by 436 days.

(21) Appl. No.: 12/404,943

(22) Filed: Mar. 16, 2009

(65) Prior Publication Data

US 2009/0298175 A1     Dec. 3, 2009

Related U.S. Application Data

(60) Provisional application No. 61/060,706, filed on Jun. 11, 2008, provisional application No. 61/047,057, filed on Apr. 22, 2008, provisional application No. 61/036,648, filed on Mar. 14, 2008.

(51) Int. Cl.
*A61K 31/575*     (2006.01)
*C07J 9/00*        (2006.01)

(52) U.S. Cl.
CPC . *A61K 31/575* (2013.01); *C07J 9/00* (2013.01)
USPC .......................................... 552/541; 514/179

(58) Field of Classification Search
None
See application file for complete search history.

(56) References Cited

U.S. PATENT DOCUMENTS

| | | | |
|---|---|---|---|
| 6,333,318 | B1 | 12/2001 | Evans et al. |
| 7,091,038 | B2 | 8/2006 | Palli et al. |
| 2002/0110861 | A1 | 8/2002 | Dhadialla et al. |
| 2002/0119521 | A1 | 8/2002 | Palli et al. |
| 2004/0049037 | A1 | 3/2004 | Tice et al. |
| 2004/0087028 | A1* | 5/2004 | Cunningham ................ 435/456 |
| 2005/0137175 | A1* | 6/2005 | Bernard et al. ............... 514/169 |
| 2005/0191385 | A1 | 9/2005 | Amato |
| 2006/0240088 | A1* | 10/2006 | Lawrence et al. ............. 424/450 |

FOREIGN PATENT DOCUMENTS

WO     WO 99/58155     11/1999

OTHER PUBLICATIONS

Graham, L. D., "Ecdysone—Controlled Expresion of Transgenes" Expert Opin. Biol. Ther. (2002) vol. 2 No. 5 (pp. 525-535).*
Nagy et al., "Mechanism of the nuclear receptor molecular switch" Trends in Biochemical Sciences (2004) vol. 29 No. 6, pp. 317-324.*
Lin et al., "Spatially Discrete, Light-drivn Protein Expression" Chemistry and Biology (2002) vol. 9 pp. 1347-1353.*
Dinan, L. & Hormann, R.E., "Ecdysteroid Agonists and Antagonists," *Comprehensive Molecular Insect Science*, 1st ed.:197-242, Elsevier B.V., UK (2005).
Dinan, L. & Lafont, R., "Effects and applications of arthropod steroid hormones (edysteroids) in mammals," *Journal of Endocrinology*, 191:1-8, Society for Endocrinology, United States (2006).
Graham, L.D., et al., "Ligand binding by recombinant domains from insect ecdysone receptors," *Insect Biochemistry and Molecular Biology*, 37:611-626, Elsevier Ltd., Holland (2007).
Karzenowski, D., et al., "Inducible control of transgene expression with ecdysone receptor: gene switches with high sensitivity, robust expression, and reduced size," *BioTechniques*, 39:191-200, Informa Life Sciences Publishing, United States (2005).
Lafont, R. & Dinan, L., "Practical uses for ecysteroids in mammals including humans: and update," *J. Insect Sci.*, 3:1-30, JIS, United States (2003).
Lapenna, S., et al., "Ecdysteroid ligand-receptor selectivity-exploring trends to design orthogonal gene switches," *FEBS Journal*, 275:5785-5809, Blackwell Publishing Ltd., UK (2008).
No, D., et al., "Ecdysone-inducible gene expression in mammalian cells and transgenic mice," *PNAS*, 93:3346-3351, The National Academy of Sciences, United States (1996).
Palli, S.R., et al.,"Ecysteroid Receptors and Their Applications in Agriculture and Medicine," *Insect Hormones*, 73:59-100, Elsevier Academic Press, UK (2005).
Saez, E., et al., "Identification of ligands and coligands for the ecdysone-regulated gene switch," *PNAS*, 97:14512-14517, The National Academy of Sciences, United States (2000).
Tavva, V.S., et al.,"Applications of EcR Gene Switch Technology in Functional Genomics," *Arch. Insect Biochem. Physiol.*, 65:164-179, Wiley-Liss, Inc., United States (2007).
Weber, W. & Fussenegger, M., "Novel Gene Switches," *Handbook of Experimental Pharmacology*, 178:73-105, Springer-Verlag, Germany (2007).
International Search Report for International Application No. PCT/US09/01639, United States Patent and Trademark Office, Alexandria, Virginia, mailed on Aug. 19, 2009.
Written Opinion of the International Searching Authority for International Application No. PCT/US09/01639, United States Patent and Trademark Office, Alexandria, Virginia, mailed on Aug. 19, 2009.
Lapenna, S., "A Study of the Ligand-Receptor Interactions of Ecdysteroids," Thesis University of Exeter, Exeter, United Kingdom (Jul. 2006).

* cited by examiner

*Primary Examiner* — Eric S Olson
(74) *Attorney, Agent, or Firm* — Sterne, Kessler, Goldstein & Fox P.L.L.C.

(57) ABSTRACT

The present invention relates to steroidal ligands for use in nuclear receptor-based inducible gene expression systems. The invention further relates to methods of modulating the expression of genes of interest with a system containing one or more nuclear receptor complexes and one or more steroidal ligands. Further aspects include ligand compositions including therapeutic compositions.

31 Claims, 23 Drawing Sheets

FIGURE 2A

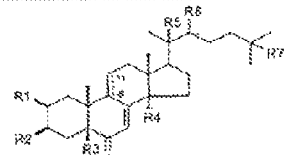

*1 = single bond, 2 = double bond

| No. | Name | R1 | R2 | R3 | R4 | R5 | R6 | R7 | C9-C11* |
|---|---|---|---|---|---|---|---|---|---|
| 1 | 20E 2-methyl ether | OCH₃ | OH | H | OH | OH | OH | OH | 1 |
| 2 | 20E 3-methyl ether | OH | OCH₃ | H | OH | OH | OH | OH | 1 |
| 3 | 20E 14-methyl ether | OH | OH | H | OCH₃ | OH | OH | OH | 1 |
| 4 | 20E 22-methyl ether | OH | OH | H | OH | OH | OCH₃ | OH | 1 |
| 5 | 20E 22-ethyl ether | OH | OH | H | OH | OH | OCH₂CH₃ | OH | 1 |
| 6 | 20E 22-n-propyl ether | OH | OH | H | OH | OH | O-n-Pr | OH | 1 |
| 7 | 20E 22-allyl ether | OH | OH | H | OH | OH | OCH₂CH=CH₂ | OH | 1 |
| 8 | 20E 22-n-butyl ether | OH | OH | H | OH | OH | O-n-Bu | OH | 1 |
| 9 | 20E 22-benzyl ether | OH | OH | H | OH | OH | OCH₂Ph | OH | 1 |
| 10 | 20E 25-methyl ether | OH | OH | H | OH | OH | OH | OCH₃ | 1 |
| 11 | 20E 2,22-dimethyl ether | OCH₃ | OH | H | OH | OH | OCH₃ | OH | 1 |
| 12 | 20E 3,22-dimethyl ether | OH | OCH₃ | H | OH | OH | OCH₃ | OH | 1 |
| 13 | 20E 14,22-dimethyl ether | OH | OH | H | OCH₃ | OH | OCH₃ | OH | 1 |
| 14 | 20E 22,25-dimethyl ether | OH | OH | H | OH | OH | OCH₃ | OCH₃ | 1 |
| 15 | 20E 2,3,14,22-tetramethyl ether | OCH₃ | OCH₃ | H | OCH₃ | OH | OCH₃ | OH | 1 |
| 16 | PoA 2-methyl ether | OCH₃ | OH | H | OH | OH | OH | H | 1 |
| 17 | PoA 14-methyl ether | OH | OH | H | OCH₃ | OH | OH | H | 1 |
| 18 | PoA 22-methyl ether | OH | OH | H | OH | OH | OCH₃ | H | 1 |
| 19 | PoA 2,22-dimethyl ether | OCH₃ | OH | H | OH | OH | OCH₃ | H | 1 |
| 20 | PoA 3,22-dimethyl ether | OH | OCH₃ | H | OH | OH | OCH₃ | H | 1 |
| 21 | PoA 14,22-dimethyl ether | OH | OH | H | OCH₃ | OH | OCH₃ | H | 1 |
| 22 | dacryhainansterone 22-methyl ether | OH | OH | H | OH | OH | OCH₃ | H | 2 |
| 23 | 20E 22-[(2'R/S)-2'-ethyloxiran-2'-yl)] ether | OH | OH | H | OH | OH | OC(cyclo-OCH₂- | OH | 1 |

FIGURE 2B

| | | | | | | )CH2CH3 | | |
|---|---|---|---|---|---|---|---|---|
| 24 | ecdysone | OH | OH | H | OH | H | OH | OH | 1 |
| 25 | 20-hydroxyecdysone | OH | OH | H | OH | OH | OH | OH | 1 |
| 26 | ponasterone A | OH | OH | H | OH | OH | OH | H | 1 |
| 27 | dacryhainansterone | OH | OH | H | OH | OH | OH | H | 2 |
| 28 | muristerone A | OH | OH | OH | OH | OH | OH | H | 1, 11-α-OH |
| 29 | polypodine B | OH | OH | OH | OH | OH | OH | OH | 1 |
| 30 | (3,5-Dimethyl-benzoic acid N-tert-butyl-N'-(2-ethyl-3-methoxy-benzoyl)-hydrazide) | | | | | | | | |

FIGURE 3

| No. | Structure | $B_{II}$ | | WT EcR | | VY-CfEcR | |
|---|---|---|---|---|---|---|---|
| | | -log ($EC_{50}$) | $EC_{50}$ (μM) | $EC_{50}$ (μM) | RMFI[a] | $EC_{50}$ (μM) | RMFI[a] |
| 1 | 20E 2-methyl ether | 5.96 | $1.1 \times 10^{-3}$ | > 33[b] | 0.00[b] | > 33[b] | 0.00[b] |
| 2 | 20E 3-methyl ether | 6.22 | $6.0 \times 10^{-4}$ | > 33[b] | 0.00[b] | ~ 20[b] | 0.21[b] |
| 3 | 20E 14-methyl ether | 5.49 | $3.2 \times 10^{-3}$ | > 33 | 0.00 | > 33 | 0.00 |
| 4 | 20E 22-methyl ether | 8.20 | $6.3 \times 10^{-6}$ | > 33[b] | 0.00[b] | > 33[b] | 0.03[b] |
| 5 | 20E 22-ethyl ether | 7.66 | $2.2 \times 10^{-5}$ | 4.85 | 0.77 | 0.76 | 1.10 |
| 6 | 20E 22-n-propyl ether | 6.08 | $8.3 \times 10^{-4}$ | > 33 | 0.00 | ~ 12 | 0.49 |
| 7 | 20E 22-allyl ether | 6.80 | $1.6 \times 10^{-4}$ | > 33 | 0.00 | ~ 20 | 0.08 |
| 8 | 20E 22-n-butyl ether | 7.00 | $1.0 \times 10^{-4}$ | > 33 | 0.01 | 8.99 | 0.29 |
| 9 | 20E 22-benzyl ether | 7.66 | $2.2 \times 10^{-5}$ | > 33 | 0.00 | ~ 10 | 0.37 |
| 10 | 20E 25-methyl ether | 7.22 | $6.0 \times 10^{-5}$ | > 33 | 0.00 | ~ 11 | 0.17 |
| 11 | 20E 2,22-dimethyl ether | 6.03 | $9.3 \times 10^{-4}$ | > 33[b] | 0.00[b] | > 33[b] | 0.00[b] |
| 12 | 20E 3,22-dimethyl ether | 6.66 | $2.2 \times 10^{-4}$ | > 33[b] | 0.00[b] | > 33[b] | 0.00[b] |
| 13 | 20E 14,22-dimethyl ether | 5.60 | $2.5 \times 10^{-3}$ | - | - | - | - |
| 14 | 20E 22,25-dimethyl ether | 6.92 | $1.2 \times 10^{-4}$ | > 33 | 0.00 | ~ 20 | 0.07 |
| 15 | 20E 2,3,14,22-tetramethyl ether | 4.05 | $9.0 \times 10^{-2}$ | > 33[b] | 0.00[b] | > 33[b] | 0.00[b] |
| 16 | PoA 2-methyl ether | 7.37 | $4.3 \times 10^{-5}$ | ~ 20 | 0.16 | ~ 3 | 0.54 |
| 17 | PoA 14-methyl ether | 7.22 | $6.0 \times 10^{-5}$ | ~ 20 | 0.16 | 6.60 | 0.76 |
| 18 | PoA 22-methyl ether | 7.66 | $2.2 \times 10^{-5}$ | ~ 2 | 0.58 | 0.7 | 0.58 |
| 19 | PoA 2,22-dimethyl ether | 7.52 | $3.0 \times 10^{-5}$ | 27.84 | 0.03 | 12.89 | 0.59 |
| 20 | PoA 3,22-dimethyl ether | 7.92 | $1.2 \times 10^{-5}$ | ~ 12 | 0.14 | ~ 2 | 0.47 |
| 21 | PoA 14,22-dimethyl ether | 6.77 | $1.7 \times 10^{-4}$ | > 33 | 0.00 | ~ 15 | 0.21 |
| 22 | dacryhainansterone 22-methyl ether | 7.00 | $1.0 \times 10^{-4}$ | 13.66 | 0.32 | 1.50 | 0.55 |
| 23 | 20E 22-[(2'R/S)-2'-ethyloxiran-2'-yl)] ether | 4.66 | $2.2 \times 10^{-2}$ | - | - | - | - |
| 24 | ecdysone | 5.98 | $1.0 \times 10^{-3}$ | > 33 | 0.00 | > 33 | 0.00 |
| 25 | 20-hydroxyecdysone | 8.12 | $7.6 \times 10^{-6}$ | > 33 | 0.00 | ~ 20 | 0.12 |
| 26 | ponasterone A | 9.59 | $2.6 \times 10^{-7}$ | 0.19 | 0.18 | 0.103 | 0.52 |
| 28 | muristerone A | 7.66 | $2.2 \times 10^{-5}$ | 7.39 | 0.62 | 1.03 | 0.80 |
| 29 | polypodine B | 9.00 | $1.0 \times 10^{-5}$ | ~ 12 | 0.21 | ~ 7 | 0.58 |
| | | | | reference FI (1 μM) | | | |
| 30 | 3,5-Dimethyl-benzoic acid N-tert-butyl-N'-(2-ethyl-3-methoxy-benzoyl)-hydrazide | - | | 3796 | | 8989 | |
| | | | | average background FI (DMSO control) | | | |
| | | | | 0.94 | | 2.1 | |

FIGURE 5

| | |
|---|---|
| No. of Training Set members | 140 |
| No. of descriptors | 1250 |
| Minimum $\sigma$ | 0.50 |
| Optimal no. of components | 6 |
| | |
| $S_{PRESS}$ | 0.858 |
| $r^2$ | 0.866 |
| $S$ | 0.463 |
| $q^2$ | 0.538 |
| F value (n1 = 6, n2 = 133) | 143.084[b] |
| Probability of $R^2 = 0$ | 0 |
| | |
| Model relative contributions: | |
| CoMFA indicator steric | 0.251 |
| CoMFA indicator electrostatic | 0.269 |
| CoMSIA H-bond acceptor | 0.180 |
| CoMSIA H-bond donor | 0.167 |
| CoMSIA hydrophobic | 0.102 |
| PSA | 0.032 |

FIGURE 6

| Functional group | Δ -LogEC₅₀ | Average |
|---|---|---|
| 2β-OH → 2β-OMe | -2.16 (1,25) | -1.67 |
| | -2.17 (11,4) | |
| | -2.22 (16,26) | |
| | -0.13 (19,18) | |
| 3β-OH → 3β-OMe | -1.90 (2,25) | -1.06 |
| | -1.54 (12,4) | |
| | 0.26 (20,18) | |
| 14α-OH → 14α-OMe | -2.63 (3,25) | -2.12 |
| | -2.60 (13,4) | |
| | -2.36 (17,26) | |
| | -0.89 (21,18) | |
| 22R-OH → 22R-OMe | 0.08 (4,25) | -0.35 |
| | 0.07 (11,1) | |
| | 0.44 (12,2) | |
| | 0.11 (13,3) | |
| | -0.30 (14,10) | |
| | -1.93 (18,26) | |
| | -1.28 (22,27) | |
| | 0.16 (19,16) | |
| | -0.45 (21,17) | |
| 22R-OH → 22R-OEt | -0.46 (5,25) | -0.46 |
| 22R-OH → 22R-O-nPr | -2.04 (6,25) | -2.04 |
| 22R-OH → 22R-O-Al | -1.32 (7,25) | -1.32 |
| 22R-OH → 22R-O-nBu | -1.82 (8,25) | -1.82 |
| 22R-OH → 22R-O-Bz | -0.46 (9,25) | -0.46 |
| 25-OH → 25-OMe | -0.90 (10,25) | -1.09 |
| | -1.28 (14,4) | |
| 2β-,22R-di-OH → 2β-,22R-di-OMe | -2.09 (11,25) | -2.08 |
| | -2.06 (19,26) | |
| 3β-,22R-di-OH → 3β-,22R-di-OMe | -1.46 (12,25) | -1.56 |
| | -1.66 (20,26) | |
| 14α-,22R-di-OH → 14α-,22R-di-OMe | -2.52 (13,25) | -2.67 |
| | -2.82 (21,26) | |
| 22R-,25-di-OH → 22R-,25-di-OMe | -1.20 (14,25) | -1.20 |
| 2β-,3β-,14α-,22R-tetra-OH → 2β-,3β-,14α-,22R-tetra-OMe | -4.08 (15,25) | -4.08 |

FIGURE 7

| No. | Compound | MlogP | BBB $\log(C_{brain}/C_{blood})$ | Caco-2 (cm/sec) | HSA bind (M) | $H_2O$ solubility (mg/mL) |
|---|---|---|---|---|---|---|
| 4 | 20E 22-methyl ether | 0.98 | -0.48 | $16.3 \times 10^{-6}$ | 2.31 | 0.54 |
| 5 | 20-hydroxyecdysone 22-ethyl ether | 0.81 | -0.61 | $13.9 \times 10^{-6}$ | $2.1 \times 10^{-4}$ | 0.922 |
| 7 | 20-hydroxyecdysone 22-allyl ether | 1.26 | -0.31 | $20.4 \times 10^{-6}$ | $2.5 \times 10^{-4}$ | 0.856 |
| 10 | 20-hydroxyecdysone 25-methyl ether | 1.38 | -0.77 | $17.3 \times 10^{-6}$ | $2.3 \times 10^{-4}$ | 0.510 |
| 14 | 20-hydroxyecdysone 22,25-dimethyl ether | 1.52 | -0.55 | $24.1 \times 10^{-6}$ | $2.7 \times 10^{-4}$ | 0.293 |
| 16 | ponasterone A 2-methyl ether | 1.88 | 0.16 | $20.0 \times 10^{-6}$ | $3.4 \times 10^{-4}$ | 0.137 |
| 18 | ponasterone A 22-methyl ether | 2.1 | 0.23 | $26.5 \times 10^{-6}$ | $3.1 \times 10^{-4}$ | 0.052 |
| 20 | ponasterone A 3,22-dimethyl ether | 2.31 | -0.47 | $29.1 \times 10^{-6}$ | $3.8 \times 10^{-4}$ | 0.083 |
| 25 | 20-hydroxyecdysone | 1.25[1] | -0.89 | $16.3 \times 10^{-6}$ | $2.7 \times 10^{-4}$ | 0.755[2] |
| 26 | ponasterone A | 2.19[1] | -0.35 | $19.0 \times 10^{-6}$ | $2.5 \times 10^{-4}$ | 0.270[2] |
| 28 | muristerone A | 0.69 | -0.69 | $12.7 \times 10^{-6}$ | $2.2 \times 10^{-4}$ | 1.031[2] |
| 30 | Diacylhydrazine 30 | 2.24[1] | -0.45 | $20.9 \times 10^{-6}$ | $19.3 \times 10^{-4}$ | 3.590[2] |

FIGURE 8

| No. | Structure | AaEcR | | DmEcR | |
|---|---|---|---|---|---|
| | | $EC_{50}$ (μM) | RMFI | $EC_{50}$ (μM) | RMFI[p] |
| 7 | 20E 22-allyl ether | 0.138 | 0.91 | ~ 5 | 0.22 |
| 8 | 20E 22-n-butyl ether | 2.72 | 0.63 | 14.6 | 0.50 |
| 10 | 20E 25-methyl ether | ~ 0.3 | 0.58 | 5.45 | 0.49 |
| 14 | 20E 22,25-dimethyl ether | 0.122 | 1.03 | 1.58 | 0.62 |
| 18 | PoA 22-methyl ether | 0.00038 | 0.76 | 0.066 | 1.31 |
| 25 | 20-hydroxyecdysone | 0.93 | 0.91 | ~ 10 | 0.47 |
| 26 | ponasterone A | 0.0011 | 0.67 | 0.113 | 0.64 |
| 28 | muristerone A | 0.0093 | 1.01 | 0.112 | 1.13 |
| | | reference FI (1 μM) | | | |
| 30 | 3,5-Dimethyl-benzoic acid N-tert-butyl-N'-(2-ethyl-3-methoxy-benzoyl)-hydrazide | 160 | | 494 | |
| | | average background FI (DMSO control) | | | |
| | | 7.7 | | 0.76 | |

FIGURE 9

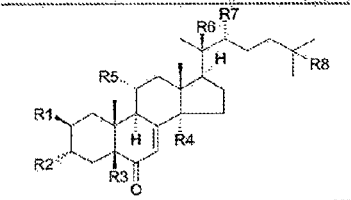

| Name | R1 | R2 | R3 | R4 | R5 | R6 | R7 | R8 |
|---|---|---|---|---|---|---|---|---|
| 2-deoxyecdysone | H | β-OH | H | OH | H | H | OH | OH |
| ecdysone | OH | β-OH | H | OH | H | H | OH | OH |
| 2-deoxy-20-hydroxyecdysone | H | β-OH | H | OH | H | OH | OH | OH |
| 22-deoxy-20-hydroxyecdysone (taxisterone) | OH | β-OH | H | OH | H | OH | H | OH |
| ponasterone A | OH | β-OH | H | OH | H | OH | OH | H |
| 20-hydroxyecdysone | OH | β-OH | H | OH | H | OH | OH | OH |
| 3-epi-20-hydroxyecdysone (coronatasterone) | OH | α-OH | H | OH | H | OH | OH | OH |
| 20E 2-methyl ether | OCH$_3$ | β-OH | H | OH | H | OH | OH | OH |
| 20E 3-methyl ether | OH | β-OCH$_3$ | H | OH | H | OH | OH | OH |
| 20E 22-methyl ether | OH | β-OH | H | OH | H | OH | OCH$_3$ | OH |
| 20E 2,22-dimethyl ether | OCH$_3$ | β-OH | H | OH | H | OH | OCH$_3$ | OH |
| 20E 3,22-dimethyl ether | OH | β-OCH$_3$ | H | OH | H | OH | OCH$_3$ | OH |
| 20E 2,3,14,22-tetramethyl ether | OCH$_3$ | β-OCH$_3$ | H | OCH$_3$ | H | OH | OCH$_3$ | OH |
| 20-hydroxyecdysone-22-acetate | OH | β-OH | H | OH | H | OH | -C(O)CH$_3$ | OH |
| 20-hydroxyecdysone 22-acetoxyacetate | OH | β-OH | H | OH | H | OH | -OC(O)CH$_2$OC(O)CH$_3$ | OH |
| 20-hydroxyecdysone 22-O-pyrrole carboxylate | OH | β-OH | H | OH | H | OH | -OC(O)-2'-pyrrole | OH |
| 20-hydroxyecdysone-2,3-acetonide | β,β-OC(CH$_3$)$_2$O- | | H | OH | H | H | OH | OH |
| 20-hydroxyecdysone-20,22-acetonide | OH | β-OH | H | OH | H | -OC(CH$_3$)$_2$O- | | OH |
| polypodine B | OH | β-OH | OH | OH | H | OH | OH | OH |
| muristerone A | OH | β-OH | OH | OH | OH | OH | OH | H |
| ajugasterone C | OH | β-OH | H | OH | OH | OH | OH | H |
| turkesterone | OH | β-OH | H | OH | OH | OH | OH | OH |
| turkesterone-11 α-propionate | OH | β-OH | H | OH | -OC(O)CH$_2$CH$_3$ | OH | OH | OH |
| turkesterone-11 α-hexanoate | OH | β-OH | H | OH | -OC(O)(CH$_2$)$_4$CH$_3$ | OH | OH | OH |
| turkesterone-11α-decanoate | OH | β-OH | H | OH | -OC(O)(CH$_2$)$_8$CH$_3$ | OH | OH | OH |

FIGURE 10

| Name | R1 |
|---|---|
| stachysterone C | ![OH group with alkene] |
| 25,26-didehydroponasterone A, (iso-stachysterone C (Δ25(26))) | ![OH group with terminal alkene] |
| 22-dehydro-20-hydroxyecdysone | ![ketone with OH] |
| (25S)-inokosterone | ![diol structure] |
| (25R)-inokosterone | ![diol structure] |
| makisterone A | ![OH with methyl groups and OH] |
| makisterone C | ![OH with ethyl and OH] |
| carthamosterone | ![lactone structure with OH] |
| cyasterone | ![lactone structure with OH] |
| canescensterone | ![pyrrole ester with OH] |

FIGURE 11
| Name | Structure |
|---|---|
| poststerone | 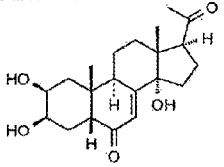 |
| 25-hydroxydacryhainansterone | 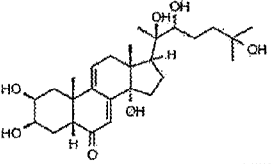 |
| (5α-H)-20-hydroxyecdysone | 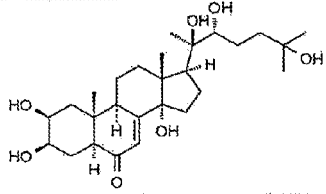 |
| 6α-hydroxy-20-hydroxyecdysone | 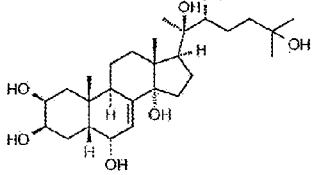 |
| 6β-hydroxy-20-hydroxyecdysone | 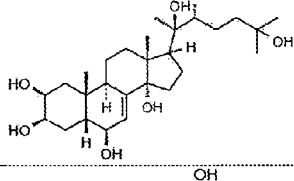 |
| integristerone A | 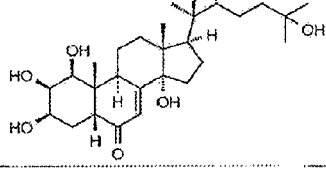 |
| iso-homobrassinolide | 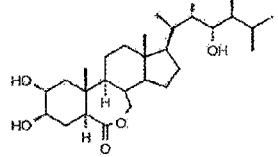 |

FIGURE 12

```
             --------H1--------    --H2---                  ---------H3-
                 |           |       |    |                     |
Bm/349    LSANQKS--LIARLVWYQEGYEQPSDEDLKRVTQTWQSDEEDEE-SDLPFRQITEMTILT 405
Ms/290    LSANQKS--LIARLVWYQEGYEQPSEEDLKRVTQTWQLEEEEEEETDMPFRQITEMTILT 347
Cf/284    LTANQQF--LIARLIWYQDGYEQPSDEDLKRITQTWQQADDENEESDTPFRQITEMTILT 341
VY/284    LTANQQF--LIARLIWYQDGYEQPSDEDLKRITQTWQQADDENEESDTPFRQITEMTILT 341
Dm/416    LTYNQLA--VIYKLIWYQDGYEQPSEEDLRRIMS---QPDENESQTDVSFRHITEITILT 470
Aa/333    LTANQMA--VIYKLIWYQDGYEQPSEEDLKRIMIG--SPNEEEDQHDVHFRHITEITILT 388
Ama/334   LSSSQED--LINKLVYYQQEFESPSEEDMKKTTP--PPLGDSEEDNQRRFQHITEITILT 389
Ba/213    ITPEQEE--LIHRLVYFQNEYEHPSPEDIKRIVN--AAP-EEENVAEERFRHITEITILT 267
Nc/137    LSPEQEE--LIHRLVYFQNEYEHPAEEDLKRIEN--LPC-DDDDPCDVRYKHITEITILT 191
Tm/251    ISPEQEELILIHRLVYFQNEYEHPSEEDVKRIIN--QPI-DGEDQCEIRFRHTTEITILT 307
          ::  .*    :*  :*:::*: :* *: **:::     :  :,   :  ::: **:****
                                  o●A●                        OA▲ A●OO●

---H3----    ----H4----  ----H5----
              |           |          |          |         |
Bm/406    VQLIVEFAKGLPGFSKISQSDQITLLKASSSEVMMLRVARRYDAASDSVLFANNKAYTRD 465
Ms/348    VQLIVEFAKGLPGFSKISQSDQITLLKASSSEVMMLRVARRYDAATDSVLFANNQAYTRD 407
Cf/342    VQLIVEFAKGLPGFAKISQPDQITLLKACSSEVMMLRVARRYDAASDSVLFANNQAYTRD 401
VY/342    VQLIVEFAKGLPGFAKISQPDQITLLKACSSEVMMLRVARRYDAASDSILFANNQAYTRD 401
Dm/471    VQLIVEFAKGLPAFTKIPQEDQITLLKACSSEVMMLRMARRYDHSSDSIFFANNRSYTRD 530
Aa/389    VQLIVEFAKGLPAFTKIPQEDQITLLKACSSEVMMLRMARRYDAATDSILFANNRSYTRD 448
Ama/390   VQLIVEFSKRVPGFDTLAREDQITLLKACSSEVMMLRGARKYDVKTDSIVFANNQPYTRD 449
Ba/268    VQLIVEFSKRLPGFDKLIREDQIALLLKACSSEVMMFRMARRYDAETDSILFATNQPYTRE 327
Nc/192    VQLIVEFAKKLPGFDKLLREDQIVLLKACSSEVMMLRMARRYDVQTDSILFANNQPYTRE 251
Tm/308    VQLIVEFAKRLPGFDKLLQEDQIALLLKACSSEVMMFRMARRYDVQSDSILFVNNQPYPRD 367
          *******:*  :*.*  ..:  : ***.****.******:* **:**   :**:.*.,*:.*.*:
           o   ●                       ●●  ●A ●            ▲A▲●AO

H6--    -------H7-------    -----H8------        -------H9--
            |         |       |         |      |              |      |
Bm/466    NYRQGGMAYVIEDLLHFCRCMFAMGMDNVHFALLTAIVIFSDRPGLEQPSLVEEIQRYYL 525
Ms/408    NYRKAGMSYVIEDLLHFCRCMYSMSMDNVHYALLTAIVIFSDRPGLEQPLLVEEIQRYYL 467
Cf/402    NYRKAGMAYVIEDLLHFCRCMYSMALDNIHYALLTAVVIFSDRPGLEQPQLVEEIQRYYL 461
VY/402    NYRKAGMAEVIEDLLHFCRCMYSMALDNIHYALLTAVVIFSDRPGLEQPQLVEEIQRYYL 461
Dm/531    SYKMAGMADNIEDLLHFCRQMFSMKVDNVEYALLTAIVIFSDRPGLEKAQLVEAIQSYYI 590
Aa/449    SYRMAGMADTIEDLLHFCRQMFSLTVDNVEYALLTAIVIFSDRPGLEQAELVEHIQSYYI 508
Ama/450   NYRSASVGDSADALFRFCRKMCQLRVDNAEYALLTAIVIFSERPSLVDPHKVERIQEYYI 509
Ba/328    SYTVAGMGDTVEDLLRFCRHMCAMKVDNAEYALLTAIVIFSERPSLSEGWKVEKIQEIYI 387
Nc/252    SYTMAGVGEVIEDLLRFGRLMCSMKVDNAEYALLTAIVIFSERPNLAEGWKVEKIQEIYL 311
Tm/368    SYNLAGMGETIEDLLHFCRTMYSMKVDNAEYALLTAIVIFSERPSLIEGWKVEKIQEIYL 427
           .*  ..:.    :  *::*   * *   : :**  .:*****:****;**,* ,  ** **   *;
                    ●     ▲ AO   ●

---H9------    ----------H10---------   ----H11---    --H12--
              |              |              |         |             |
Bm/526    NTLRIYIINQNSASSRCAVIYGRILSVLTELRTLGTQNSNMCISLKLKNRKLPPFLEEIWDVA 588
Ms/468    KTLRVYILNQHSASPRCAVLFGKILGVLTELRTLGTQNSNMCISLKLKNRKLPPFLEEIWDVA 530
Cf/462    NTLRIYILNQLSGSARSSVIYGKILSILSELRTLGMQNSNMCISLKLKNRKLPPFLEEIWDVA 524
VY/462    NTLRIYILNQLSGSARSSVIYGKILSILSELRTLGMQNSNMCISLKLKNRKLPPFLEEIWDVA 524
Dm/591    DTLRIYILNRHCGDSMSLVFYAKLLSILTELRTLGNQNAEMCFSLKLKNRKLPKFLEEIWDVH 653
Aa/509    DTLRIYILNRHAGDPKCSVIFAKLLSILTELRTLGNQNSEMCFSLKLKNRKLPRFLEEIWDVQ 571
Ama/510   ETLRMYSENH--RPP-GKNYFARLLSILTELRTLGNMNAEMCFSLKVQNKKLPPFLAEIWDIQ 569
Ba/388    EALKAYVENR--RKPYATTIFAKLLSVLTELRTLGNMNSETCFSLKLKNRKVPSFLEEIWDVV 448
Nc/402    EALKSYVDNR--VKPRSPTIFAKLLSVLTELRTLGNQNSEMCFSLNYATANMPPFLEEIWX-- 370
Tm/428    EALRAYVDNR--RSPSRGTIFAKLLSVLTELRTLGNQNSEMCISLKLKNKKLPPFLDEIWDVD 488
          .:*: * *:       .    :.::*.:*:****  *:: *:**:   .   ::* ** ***
                                              ●  ●● o    oo  o    ●
```

FIGURE 13A

| Name | BmEcR | | MsEcR | | CfEcR | | VY-CfEcR | |
|---|---|---|---|---|---|---|---|---|
| | EC50 (μM) | RMFI | EC50 (μM) | RMFI | EC50 (μM) | RMFI | EC50 (μM) | RMFI |
| 2-deoxyecdysone | > 33 | 0.001 | > 33 | 0.021 | > 33 | 0.000 | > 33 | 0.000 |
| ecdysone | > 33 | 0.001 | > 33 | 0.030 | > 33 | 0.001 | > 33 | 0.001 |
| 2-deoxy-20-hydroxyecdysone | > 33 | 0.018 | ~ 10 | 0.513 | > 33 | 0.000 | > 33 | 0.010 |
| 22-deoxy-20-hydroxyecdysone (taxisterone) | > 33 | 0.001 | ~ 15 | 0.046 | > 33 | 0.001 | > 33 | 0.003 |
| ponasterone A | 0.113 | 0.977 | ~ 0.03 | 0.811 | 0.195 | 0.180 | 0.109 | 0.520 |
| 20-hydroxyecdysone | ~ 20 | 0.132 | ~ 10 | 0.700 | > 33 | 0.005 | ~ 20 | 0.119 |
| 3-epi-20-hydroxyecdysone (coronatasterone) | > 33 | 0.003 | ~ 10 | 0.109 | > 33 | 0.001 | > 33 | 0.003 |
| 20-hydroxyecdysone-22-acetate | > 33 | 0.006 | ~ 2 | 0.049 | > 33 | 0.001 | > 33 | 0.003 |
| 20-hydroxyecdysone 22-acetoxyacetate | > 33 | 0.032 | ~ 10 | 0.523 | > 33 | 0.001 | > 33 | 0.018 |
| 20-hydroxyecdysone 22-O-pyrrole carboxylate | > 33 | 0.002 | > 33 | 0.034 | > 33 | 0.001 | > 33 | 0.000 |
| 20-hydroxyecdysone-2,3-acetonide | > 33 | 0.016 | ~ 10 | 0.442 | > 33 | 0.001 | > 33 | 0.006 |
| 20-hydroxyecdysone-20,22-acetonide | > 33 | 0.014 | ~ 12 | 0.094 | > 33 | 0.000 | ~ 15 | 0.117 |
| polypodine B | ~ 8 | 0.830 | ~ 2 | 1.004 | ~ 12 | 0.212 | ~ 7 | 0.583 |
| muristerone A | 2.985 | 0.989 | 0.660 | 1.061 | 7.393 | 0.623 | 1.069 | 0.803 |
| ajugasterone C | ~ 10 | 0.60 | ~ 7 | 0.95 | ~ 20 | 0.08 | 8.91 | 0.52 |
| turkesterone | > 33 | 0.003 | ~ 12 | 0.114 | > 33 | 0.001 | > 33 | 0.003 |
| turkesterone-11 a -propionate | > 33 | 0.002 | > 33 | 0.019 | > 33 | 0.000 | > 33 | 0.001 |
| turkesterone-11 a -hexanoate | > 33 | 0.001 | > 33 | 0.010 | > 33 | 0.001 | > 33 | 0.001 |
| turkesterone-11a-decanoate | > 33 | 0.001 | > 33 | 0.009 | > 33 | 0.001 | > 33 | 0.001 |
| stachysterone C | ~ 5 | 1.266 | 0.872 | 1.254 | ~ 10 | 0.514 | ~ 4 | 1.012 |
| 25,26-didehydroponasterone A, (iso-stachysterone C (Δ25(26))) | 6.279 | 1.150 | 0.608 | 0.999 | ~ 12 | 0.361 | 4.322 | 0.896 |
| 22-dehydro-20-hydroxyecdysone | > 33 | 0.005 | 10.277 | 0.259 | > 33 | 0.000 | > 33 | 0.007 |
| (25S)-inokosterone | > 33 | 0.001 | ~ 10 | 0.213 | > 33 | 0.001 | > 33 | 0.002 |
| (25R)-inokosterone | > 33 | 0.008 | ~ 10 | 0.295 | > 33 | 0.001 | > 33 | 0.013 |
| makisterone A | > 33 | 0.019 | ~ 10 | 0.412 | > 33 | 0.001 | > 33 | 0.012 |
| makisterone C | > 33 | 0.030 | ~ 4 | 0.378 | > 33 | 0.001 | > 33 | 0.042 |
| carthamosterone | > 33 | 0.002 | > 33 | 0.018 | > 33 | 0.001 | > 33 | 0.001 |
| cyasterone | ~ 1 | 0.343 | 1.533 | 1.407 | ~ 1 | 0.268 | ~ 0.6 | 0.634 |
| canescensterone | > 10 | 0.001 | > 10 | 0.007 | > 10 | 0.001 | > 10 | 0.001 |
| poststerone | > 33 | 0.001 | > 33 | 0.008 | > 33 | 0.000 | > 33 | 0.000 |

FIGURE 13B

| 25-hydroxydacryhainansterone | > 33 | 0.019 | ~ 10 | 0.542 | > 33 | 0.001 | > 33 | 0.017 |
|---|---|---|---|---|---|---|---|---|
| (5a-H)-20-hydroxyecdysone | > 33 | 0.001 | > 33 | 0.008 | > 33 | 0.091 | > 33 | 0.000 |
| 6a-hydroxy-20-hydroxyecdysone | > 33 | 0.001 | > 33 | 0.010 | > 33 | 0.000 | > 33 | 0.000 |
| 6b-hydroxy-20-hydroxyecdysone | > 33 | 0.009 | ~ 12 | 0.175 | > 33 | 0.091 | > 33 | 0.006 |
| integristerone A | > 33 | 0.537 | ~ 12 | 0.870 | > 33 | 0.585 | > 33 | 0.599 |
| iso-homobrassinolide | FI = 2 (10 µM) | | - | | FI = 0.44 (10 µM) | | FI = 0.25 (10 µM) | |
| | reference FI (1 µM) | | | | | | | |
| 2-ethyl-3-methoxy-benzoic acid N'-tert-butyl-N'-(3,5-dimethyl-benzoyl)-hydrazide | 1776 | | 164 | | 3797 | | 4393 | |
| | average background FI (DMSO control) | | | | | | | |
| | 2.9 | | 30.6 | | 0.94 | | 2.15 | |

FIGURE 14A

| Name | Bll EC50 (µM) | DmEcR EC50 (µM) | DmEcR RMFI | AaEcR EC50 (µM) | AaEcR RMFI | AmaEcR EC50 (µM) | AmaEcR RMFI | BaEcR EC50 (µM) | BaEcR RMFI | NcEcR EC50 (µM) | NcEcR RMFI | TmEcR EC50 (µM) | TmEcR RMFI |
|---|---|---|---|---|---|---|---|---|---|---|---|---|---|
| 2-deoxyecdysone | 34.674 | >33 | 0.008 | ~10 | 0.551 | ~1 | 0.319 | >33 | 0.104 | ~6 | 0.639 | >33 | 0.032 |
| ecdysone | 1.047 | >33 | 0.002 | ~15 | 0.491 | ~7 | 0.853 | >33 | 0.087 | 3.268 | 0.641 | >33 | 0.068 |
| 2-deoxy-20-hydroxyecdysone | 0.977 | >33 | 0.023 | ~5 | 1.400 | ~5 | 1.315 | ~15 | 0.943 | ~3.3 | 1.209 | ~20 | 0.228 |
| 22-deoxy-20-hydroxyecdysone (taxisterone) | 0.055 | ~20 | 0.055 | 1.677 | 1.020 | ~10 | 0.867 | ~10 | 1.717 | 3.045 | 0.762 | ~20 | 0.215 |
| ponasterone A | 2.57 x 10⁻⁴ | | 0.643 | 0.002 | 0.670 | 0.002 | 1.395 | 0.031 | 8.968 | 3.019 x 10⁻⁴ | 0.997 | 0.044 | 1.375 |
| 20-hydroxyecdysone | 7.586 x 10⁻³ | ~10 | 0.473 | 0.932 | 0.908 | ~2 | 1.098 | ~5 | 1.342 | ~0.8 | 1.420 | ~15 | 0.380 |
| 3-epi-20-hydroxyecdysone (coronatasterone) | 0.151 | ~20 | 0.045 | ~8 | 0.872 | ~10 | 0.766 | ~20 | 0.169 | 4.842 | 0.837 | >33 | 0.022 |
| 20-hydroxyecdysone-22-acetate | 2.089 | >33 | 0.007 | ~2 | 0.099 | ~2 | 0.471 | ~2 | 0.160 | 2.440 | 0.469 | ~2 | 0.092 |
| 20-hydroxyecdysone 22-acetoxyacetate | 0.034 | ~20 | 0.172 | ~3.3 | 0.864 | ~3.3 | 1.280 | ~12 | 1.981 | 0.755 | 0.975 | ~10 | 0.063 |
| 20-hydroxyecdysone 22-O-pyrrole carboxylate | - | ~20 | 0.057 | ~10 | 0.656 | ~5 | 0.719 | ~15 | 0.955 | ~5 | 0.559 | ~20 | 0.077 |
| 20-hydroxyecdysone-2,3-acetonide | 0.151 | >33 | 0.003 | ~15 | 0.403 | ~7 | 0.474 | ~15 | 0.152 | 2.904 | 0.893 | ~10 | 0.422 |
| 20-hydroxyecdysone-20,22-acetonide | 0.362 | >33 | 0.036 | ~12 | 0.175 | ~20 | 0.323 | >33 | 0.080 | ~10 | 1.033 | ~10 | 0.074 |
| polypodine B | 1.060 x 10⁻³ | ~2 | 0.892 | 0.173 | 1.043 | ~3.3 | 1.563 | ~3.3 | 1.752 | ~0.1 | 0.723 | ~10 | 0.568 |
| muristerone A | 0.022 | 0.058 | 1.130 | 0.023 | 1.012 | 0.128 | 1.254 | 0.829 | 1.527 | <0.01 | 0.709 | ~5 | 1.185 |
| ajugasterone C | 0.056 | ~2 | 1.17 | 0.97 | 0.82 | ~0.2 | 1.21 | 2.06 | 2.04 | 0.08 | 0.95 | 0.51 | 0.66 |
| turkesterone | 1.072 | ~15 | 0.342 | 3.363 | 0.874 | ~10 | 0.986 | ~20 | 0.727 | 1.346 | 1.069 | >33 | 0.086 |
| turkesterone-11 α -propionate | 8.318 | >33 | 0.004 | ~15 | 0.367 | ~10 | 0.501 | >33 | 0.065 | ~10 | 0.698 | >33 | 0.046 |

FIGURE 14B

| | | | | | | | | | | | | |
|---|---|---|---|---|---|---|---|---|---|---|---|---|
| turkesterone-11a-hexanoate | 21.878 | >33 | 0.003 | ~12 | 0.312 | ~10 | 0.465 | >33 | 0.057 | ~7 | 0.417 | >33 | 0.058 |
| turkesterone-11a-decanoate | 1.096 | >33 | 0.003 | >33 | 0.037 | >33 | 0.216 | >33 | 0.062 | >33 | 0.052 | >33 | 0.064 |
| stachysterone C | 0.011 | 0.385 | 1.243 | 0.044 | 1.203 | ~0.1 | 1.337 | 0.658 | 2.051 | 0.013 | 0.866 | 1.469 | 1.413 |
| 25,26-didehydroponasterone A, (iso-stachysterone C (D25(26))) | 6.457 × 10⁻³ | 0.912 | 1.006 | 0.024 | 1.133 | 0.025 | 1.195 | 0.382 | 1.101 | 0.066 | 0.903 | 1.402 | 1.502 |
| 22-dehydro-20-hydroxyecdysone | 0.170 | ~20 | 0.052 | ~2 | 0.951 | ~7 | 0.988 | ~12 | 1.418 | 1.843 | 0.973 | ~15 | 0.101 |
| (25S)-inokosterone | 0.269 | ~20 | 0.051 | ~4 | 0.907 | ~3.3 | 0.784 | ~10 | 1.322 | ~1.5 | 0.810 | ~10 | 0.155 |
| (25R)-inokosterone | 0.151 | 9.466 | 0.293 | ~2.5 | 1.001 | ~3.3 | 0.939 | ~10 | 0.560 | 0.867 | 0.777 | ~20 | 0.177 |
| makisterone A | 0.013 | ~20 | 0.175 | 3.327 | 1.111 | 1.396 | 1.095 | ~15 | 0.322 | 0.117 | 0.878 | ~20 | 0.091 |
| makisterone C | 0.200 | ~5 | 0.109 | 1.021 | 0.670 | ~2 | 1.133 | ~3.3 | 0.404 | ~0.1 | 1.145 | ~4 | 0.316 |
| carthamosterone | 0.437 | >33 | 0.003 | ~15 | 0.396 | ~20 | 0.298 | >33 | 0.070 | ~10 | 0.880 | >33 | 0.027 |
| cyasterone | 0.032 | >33 | 0.027 | 2.966 | 0.820 | ~0.3 | 0.352 | ~10 | 0.744 | 1.825 | 1.061 | >33 | 0.029 |
| canescensterone | 5.25 × 10⁻⁴ | ~0.5 | 0.043 | ~0.2 | 0.346 | ~0.3 | 0.345 | ~0.2 | 4.851 | ~0.33 | 0.070 | ~0.33 | 0.076 |
| poststerone | 158.489 | >33 | 0.002 | >33 | 0.039 | >33 | 0.181 | >33 | 0.036 | >33 | 0.044 | >33 | 0.065 |
| 25-hydroxydacryhainansterone | 0.257 | >33 | 0.029 | ~5 | 1.066 | ~3.3 | 1.258 | ~15 | 0.678 | 1.260 | 0.877 | ~20 | 0.223 |
| (5α-H)-20-hydroxyecdysone | 3.311 | >33 | 0.002 | ~20 | 0.129 | >33 | 0.137 | >33 | 0.342 | ~15 | 0.114 | >33 | 0.018 |
| 6a-hydroxy-20-hydroxyecdysone | 1.995 | >33 | 0.003 | ~12 | 0.256 | 10.000 | 0.410 | >33 | 0.057 | ~10 | 0.415 | >33 | 0.053 |
| 6b-hydroxy-20-hydroxyecdysone | 0.170 | ~20 | 0.048 | ~6 | 0.698 | ~3.3 | 0.924 | ~20 | 0.572 | 1.704 | 0.750 | ~20 | 0.116 |
| integristerone A | 0.398 | >33 | 0.008 | ~10 | 0.832 | ~10 | 0.526 | ~20 | 0.195 | ~2 | 0.776 | ~8 | 0.112 |
| iso-homobrassinolide | inactive | FI = 0.8 (10 μM) | | FI = 0.58 (10 μM) | | FI = 0.68 (1 μM) | | FI = 0.78 (10 μM) | | FI = 0.23 (10 μM) | | FI = 0.81 (10 μM) |
| | | | | | | reference FI (1 μM) | | | | | | | |
| 2-ethyl-3-methoxy-benzoic acid N-tert-butyl-N'-(3,5-dimethyl-benzoyl)-hydrazide | - | | 789.3 | | 58.79 | | 7.82 | | 3.63 | | 79.0 | | 29.97 |
| | - | | 14.19 | | 318.6 | | 317.3 | | 63.49 | | 6.69 | | 12.03 |
| | | | | | average background FI (DMSO control) | | | | | | | | |

FIGURE 15

| Name | BmEcR | | MsEcR | | CfEcR | | VY-CfEcR | |
|---|---|---|---|---|---|---|---|---|
| | EC50 (µM) | RMFI | EC50 (µM) | RMFI | EC50 (µM) | RMFI | EC50 (µM) | RMFI |
| ecdysone | >33 | 0.00 | >33 | 0.01 | >33 | 0.00 | >33 | 0.00 |
| ponasterone A | 0.34 | 1.07 | 0.17 | 0.98 | 8.42 | 0.57 | 1.19 | 0.85 |
| 20-hydroxyecdysone | ~20 | 0.18 | ~10 | 0.62 | >33 | 0.00 | ~20 | 0.08 |
| 20E 2-methyl ether | >33 | 0.02 | ~20 | 0.10 | >33 | 0.00 | >33 | 0.00 |
| 20E 3-methyl ether | >33 | 0.04 | ~10 | 0.71 | >33 | 0.00 | ~20 | 0.21 |
| 20E 22-methyl ether | >33 | 0.02 | ~10 | 0.80 | >33 | 0.00 | >33 | 0.03 |
| 20E 2,22-dimethyl ether | >33 | 0.03 | ~20 | 0.09 | >33 | 0.00 | >33 | 0.00 |
| 20E 3,22-dimethyl ether | >33 | 0.06 | ~10 | 0.51 | >33 | 0.00 | >33 | 0.00 |
| 20E 2,3,14,22-tetramethyl ether | >33 | 0.02 | >33 | 0.00 | >33 | 0.00 | >33 | 0.00 |
| 20-hydroxyecdysone-20,22-acetonide | ~20 | 0.09 | ~12 | 0.80 | >33 | 0.00 | ~20 | 0.07 |
| polypodine B | ~9 | 0.96 | 4.35 | 1.14 | >33 | 0.16 | 11.42 | 0.54 |
| ajugasterone C | ~10 | 0.60 | ~7 | 0.95 | ~20 | 0.08 | 8.91 | 0.52 |
| poststerone | >33 | 0.00 | >33 | 0.00 | >33 | 0.00 | >33 | 0.00 |
| iso-homobrassinolide | FI = 2 (10 µM) | | - | | FI = 0.44 (10 µM) | | FI = 0.25 (10 µM) | |
| 2-ethyl-3-methoxy-benzoic acid N'-tert-butyl-N'-(3,5-dimethyl-benzoyl)-hydrazide | 36.44 | | 489.54 | | 806.17 | | 1012.93 | |
| | | | reference FI (1 µM) | | | | | |
| | | | average background FI (DMSO control) | | | | | |
| | 0.65 | | 11.16 | | 0.995 | | 1.12 | |

FIGURE 16

| Name | BII EC50 (µM) | DmEcR EC50 (µM) | DmEcR RMFI | VgEcR/RXR EC50 (µM) | VgEcR/RXR RMFI | AaEcR EC50 (µM) | AaEcR RMFI | AmaEcR EC50 (µM) | AmaEcR RMFI | BaEcR EC50 (µM) | BaEcR RMFI | NcEcR EC50 (µM) | NcEcR RMFI | TmEcR EC50 (µM) | TmEcR EC50 (µM) |
|---|---|---|---|---|---|---|---|---|---|---|---|---|---|---|---|
| ponasterone A | 2.570 x 10⁻⁴ | 0.84 | 0.75 | 0.036319 | 0.97 | < 0.01 | 1.04 | < 0.01 | 1.28 | 0.01 | 2.28 | 0.01 | 0.87 | 0.07 | 1.11 |
| ecdysone | 1.047 | > 33 | 0.01 | > 33 | 0.22 | 3.43 | 1.16 | > 33 | 0.35 | > 33 | 0.06 | 2.52 | 0.76 | > 33 | 0.04 |
| 20-hydroxyecdysone | 7.586 x 10⁻³ | ~ 15 | 0.92 | ~ 6 | 0.59 | 4.38 | 0.36 | ~ 0.8 | 0.99 | 5.35 | 1.83 | 0.60 | 0.89 | ~ 12 | 0.57 |
| 20E 2-methyl ether | 1.096 | > 33 | 0.00 | > 33 | 0.22 | > 10 | 0.31 | ~ 10 | 0.64 | > 33 | 0.06 | ~ 8 | 0.73 | > 33 | 0.04 |
| 20E 3-methyl ether | 0.603 | > 33 | 0.02 | ~ 20 | 0.34 | > 10 | 0.62 | ~ 3.3 | 0.90 | ~ 15 | 0.53 | 1.69 | 0.90 | ~ 10 | 0.65 |
| 20E 22-methyl ether | 6.310 x 10⁻³ | ~ 4 | 0.80 | ~ 1 | 1.32 | 1.04 | 0.90 | ~ 1 | 1.07 | ~ 3 | 2.82 | 2.59 | 0.91 | 7.08 | 0.91 |
| 20E 2,22-dimethyl ether | 0.933 | ~ 20 | 0.11 | ~ 15 | 0.46 | ~ 8 | 0.83 | ~ 8 | 0.93 | ~ 10 | 0.43 | ~ 10 | 0.75 | ~ 20 | 0.14 |
| 20E 3,22-dimethyl ether | 0.219 | ~ 20 | 0.07 | ~ 7 | 0.48 | 7.15 | 0.83 | ~ 2 | 1.03 | ~ 10 | 0.69 | ~ 8 | 0.92 | ~ 6 | 0.78 |
| 20E 2,3,14,22-tetramethyl ether | 89.125 | > 33 | 0.01 | > 33 | 0.22 | > 33 | 0.02 | > 33 | 0.33 | > 33 | 0.03 | > 33 | 0.01 | > 33 | 0.03 |
| 20-hydroxyecdysone-20,22-acetonide | 0.302 | ~ 12 | 0.48 | ~ 7 | 0.64 | 2.38 | 1.08 | ~ 1 | 1.29 | 8.57 | 1.46 | 1.04 | 1.04 | ~ 3 | 0.17 |
| polypodine B | 1.000 x 10⁻³ | 2.54 | 0.87 | ~ 1.5 | 0.95 | 0.05 | 0.68 | ~ 0.3 | 1.25 | 2.59 | 2.07 | 0.05 | 1.06 | ~ 3 | 0.58 |
| ajugasterone C | 0.056 | ~ 2 | 1.17 | ~ 0.6 | 0.98 | 0.07 | 0.82 | ~ 0.2 | 1.21 | 2.06 | 2.04 | 0.08 | 0.99 | 9.51 | 0.66 |
| poststerone | 158.489 | > 33 | 0.01 | > 33 | 0.23 | 10.46 | 0.71 | ~ 10 | 0.69 | > 33 | 0.17 | ~ 10 | 0.52 | > 33 | 0.03 |
| iso-homobrassinolide | inactive | FI = 0.8 (10 µM) | | | | FI = 0.58 (10 µM) | | FI = 0.68 (10 µM) | | FI = 0.78 (10 µM) | | FI = 0.23 (10 µM) | | FI = 0.81 (10 µM) | |
| | | | | | | reference FI (1 µM) | | | | | | | | | |
| 2-ethyl-3-methoxy-benzoic acid N'-tert-butyl-N'-(3,5-dimethyl-benzoyl)-hydrazide | - | 464.5 | | 5.80 | | 50.6 | | 2.55 | | 1.24 | | 124 | | 16.9 | |
| | | | | | | average background FI (DMSO control) | | | | | | | | | |
| | | 1.9 | | 2311 | | 5.94 | | 199 | | 3.00 | | 11.7 | | 32.4 | |

SEQUENCE LISTING

<160> NUMBER OF SEQ ID NOS: 30

<210> SEQ ID NO 1
<211> LENGTH: 1054
<212> TYPE: DNA
<213> ORGANISM: Chorietoneura fumiferana

<400> SEQUENCE: 1

```
cctgagtgcg tagtacccga gactcagtgc gccatgaagc ggaaagagaa gaaagcacag      60
aaggagaagg acaaactgcc tgtcagcacg acgacggtgg acgaccacat gccgcccatt     120
atgcagtgtg aacctccacc tcctgaagca gcaaggattc acgaagtggt cccaaggttt     180
ctctccgaca agctgttgga gacaaaccgg cagaaaaaca tcccccagtt gacagccaac     240
cagcagttcc ttatcgccag gctcatctgg taccaggacg ggtacgagca gccttctgat     300
gaagatttga agaggattac gcagacgtgg cagcaagcgg acgatgaaaa cgaagagtct     360
gacactccct tccgccagat cacagagatg actatcctca cggtccaact tatcgtggag     420
ttcgcgaagg gattgccagg gttcgccaag atctcgcagc ctgatcaaat tacgctgctt     480
aaggcttgct caagtgaggt aatgatgctc cgagtcgcgc gacgatacga tgcggcctca     540
gacagtgttc tgttcgcgaa caaccaagcg tacactcgcg acaactaccg caaggctggc     600
atggcctacg tcatcgagga tctactgcac ttctgccggt gcatgtactc tatggcgttg     660
gacaacatcc attacgcgct gctcacggct gtcgtcatct tttctgaccg gccagggttg     720
gcgcagccgc aactggtgga agaaatccag cggtactacc tgaatacgct ccgcatctat     780
atcctgaacc agctgagcgg gtcggcgcgt tcgtccgtca tatacggcaa gatcctctca     840
atcctctctg agctacgcac gctcggcatg caaaactcca acatgtgcat ctccctcaag     900
ctcaagaaca gaaagctgcc gcctttcctc gaggagatct gggatgtggc ggacatgtcg     960
cacacccaac cgccgcctat cctcgagtcc cccacgaatc tctagcccct gcgcgcacgc    1020
atcgccgatg ccgcgtccgg ccgcgctgct ctga                                1054
```

```
<210> SEQ ID NO 2
<211> LENGTH: 441
<212> TYPE: DNA
<213> ORGANISM: Saccharomyces cerevisiae

<400> SEQUENCE: 2
atgaagctac tgtcttctat cgaacaagca tgcgatattt gccgacttaa aaagctcaag      60
tgctccaaag aaaaaccgaa gtgcgccaag tgtctgaaga caactggga gtgtcgctac     120 tctcccaaaa ccaaaaggtc tccgctgact agggcacatc tgacagaagt ggaatcaagg     180 ctagaaaagac tggaacagct atttctactg attttcctc gagaagacct tgacatgatt     240
ttgaaaatgg attctttaca ggatataaaa gcattgttaa caggattatt tgtacaagat     300
aatgtgaata agatgccgt cacagataga ttggcttcag tggagactga tatgcctcta     360
acattgagac agcatagaat aagtgcgaca tcatcatcgg aagagagtag taacaaaggt     420
caaagacagt tgactgtatc g                                               441

<210> SEQ ID NO 3
<211> LENGTH: 659
<212> TYPE: DNA
<213> ORGANISM: Cytomegalovirus

<400> SEQUENCE: 3
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca aacttacgg taaatggccc     240 gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccccctattg acgtcaatga     420 cggtaaatgg cccgcctggc attatgccca gtacatgacc ttacgggact ttcctacttg     480
gcagtacatc tacgtattag tcatcgctat taccatggtg atgaggtttt ggcagtacac     540
caatgggcgt ggatagcggt ttgactcacg gggatttcca gtctccacc ccattgacgt     600 caatgggagt ttgttttggc accaaaatca acgggacttt ccaaaatgtc gtaacaact     659

<210> SEQ ID NO 4
<211> LENGTH: 720
<212> TYPE: DNA
<213> ORGANISM: Homo sapiens

<400> SEQUENCE: 4
gcccccgagg agatgcctgt ggacaggatc ctggaggcag agcttgctgt ggaacagaag      60
agtgaccagg gcgttgaggg tcctggggga accgggggta gcggcagcag cccaaatgac     120
cctgtgacta acatctgtca ggcagctgac aaacagctat tcacgcttgt tgagtgggcg     180
aagaggatcc cacactttt ctccttgcct ctggatgatc aggtcatatt gctgcgggca     240
ggctggaatg aactcctcat tgcctccttt tcacaccgat ccattgatgt tcgagatggc     300
atcctccttg ccacaggtct tcacgtgcac cgcaactcag cccattcagc aggagtagga     360
gccatctttg atcgggtgct gacagagcta gtgtccaaaa tgcgtgacat gaggatggac     420
aagacagagc ttggctgcct gagggcaatc attctgttta atccagatgc caagggcctc     480
tccaacccta gtgaggtgga ggtcctgcgg gagaaagtgt atgcatcact ggagacctac     540
```

```
tgcaaacaga agtaccctga gcagcaggga cggtttgcca agctgctgct acgtcttcct    600
gccctccggt ccattggcct taagtgtcta gagcatctgt ttttcttcaa gctcattggt    660
gtccccccca tcgacacctt cctcatggag atgcttgagg ctccccatca actggcctga    720
```

<210> SEQ ID NO 5
<211> LENGTH: 635
<212> TYPE: DNA
<213> ORGANISM: Locusta migratoria

<400> SEQUENCE: 5

```
tgcatacaga catgcctgtt gaacgcatac ttgaagctga aaacgagtg gagtgcaaag      60 cagaaaacca agtggaatat gagctggtgg agtgggctaa acacatcccg cacttcacat    120
ccctacctct ggaggaccag gttctcctcc tcagagcagg ttggaatgaa ctgctaattg    180
cagcattttc acatcgatct gtagatgtta aagatggcat agtacttgcc actggtctca    240
cagtgcatcg aaattctgcc catcaagctg gagtcggcac aatatttgac agagttttga    300
cagaactggt agcaaagatg agagaaatga aaatggataa aactgaactt ggctgcttgc    360
gatctgttat tcttttcaat ccagaggtga ggggtttgaa atccgcccag gaagttgaac    420
ttctacgtga aaaagtatat gccgctttgg aagaatatac tagaacaaca catcccgatg    480
aaccaggaag atttgcaaaa cttttgcttc gtctgccttc tttacgttcc ataggcctta    540
agtgtttgga gcatttgttt ttctttcgcc ttattggaga tgttccaatt gatacgttcc    600
tgatggagat gcttgaatca ccttctgatt cataa                                635
```

<210> SEQ ID NO 6
<211> LENGTH: 271
<212> TYPE: DNA
<213> ORGANISM: herpes simplex virus 7

<400> SEQUENCE: 6

```
atgggcccta aaagaagcg taaagtcgcc ccccgaccg atgtcagcct ggggacgag        60 ctccacttag acggcgagga cgtggcgatg gcgcatgccg acgcgctaga cgatttcgat    120
ctggacatgt tggggacgg ggattccccg gggccgggat ttacccccca cgactccgcc    180
ccctacggcg ctctggatat ggccgacttc gagtttgagc agatgtttac cgatgccctt    240
ggaattgacg agtacggtgg ggaattcccg g                                    271
```

<210> SEQ ID NO 7
<211> LENGTH: 309
<212> TYPE: DNA
<213> ORGANISM: Simian virus 40

<400> SEQUENCE: 7

```
ggtgtggaaa gtccccaggc tccccagcag gcagaagtat gcaaagcatg catctcaatt     60
agtcagcaac caggtgtgga agtccccag gctcccagc aggcagaagt atgcaaagca      120
tgcatctcaa ttagtcagca accatagtcc cgcccctaac tccgcccatc cgcccctaa     180 ctccgcccag ttccgcccat tctccgcccc atggctgact aatttttttt atttatgcag    240
aggccgaggc cgcctcggcc tctgagctat tccagaagta gtgaggaggc ttttttggag    300
gcctaggct                                                            309
```

<210> SEQ ID NO 8
<211> LENGTH: 19
<212> TYPE: DNA
<213> ORGANISM: Artificial Sequence
<220> FEATURE:

<223> OTHER INFORMATION: Synthetic GAL4 response element

<400> SEQUENCE: 8
ggagtactgt cctccgagc                                            19

<210> SEQ ID NO 9
<211> LENGTH: 6
<212> TYPE: DNA
<213> ORGANISM: Artificial Sequence
<220> FEATURE:
<223> OTHER INFORMATION: Synthetic promoter

<400> SEQUENCE: 9 tatata                                                           6

<210> SEQ ID NO 10
<211> LENGTH: 1653
<212> TYPE: DNA
<213> ORGANISM: Artificial Sequence
<220> FEATURE:
<223> OTHER INFORMATION: Synthetic luciferase gene

<400> SEQUENCE: 10
atggaagacg ccaaaaacat aaagaaaggc ccggcgccat tctatcctct agaggatgga    60
accgctggag agcaactgca taaggctatg aagagatacg ccctggttcc tggaacaatt   120
gcttttacag atgcacatat cgaggtgaac atcacgtacg cggaatactt cgaaatgtcc   180
gttcggttgg cagaagctat gaaacgatat gggctgaata caaatcacag aatcgtcgta   240
tgcagtgaaa actctcttca attctttatg ccggtgttgg gcgcgttatt tatcggagtt   300
gcagttgcgc ccgcgaacga catttataat gaacgtgaat tgctcaacag tatgaacatt   360
tcgcagccta ccgtagtgtt tgtttccaaa aaggggttgc aaaaaatttt gaacgtgcaa   420
aaaaaattac caataatcca gaaaattatt atcatggatt ctaaaacgga ttaccaggga   480
tttcagtcga tgtacacgtt cgtcacatct catctacctc ccggttttaa tgaatacgat   540
tttgtaccag agtcctttga tcgtgacaaa acaattgcac tgataatgaa ttcctctgga   600
tctactgggt tacctaaggg tgtggccctt ccgcatagaa ctgcctgcgt cagattctcg   660
catgccagag atcctatttt tggcaatcaa atcattccgg atactgcgat tttaagtgtt   720
gttccattcc atcacggttt tggaatgttt actacactcg atatttgat atgtggattt   780 cgagtcgtct taatgtatag atttgaagaa gagctgtttt tacgatccct tcaggattac   840
aaaattcaaa gtgcgttgct agtaccaacc ctattttcat tcttcgccaa agcactctg    900 attgacaaat acgatttatc taatttacac gaaattgctt ctgggggcgc acctctttcg   960
aaagaagtcg ggaagcggt tgcaaaacgc ttccatcttc cagggatacg acaaggatat   1020
gggctcactg agactacatc agctattctg attacacccg agggggatga taaaccgggc   1080
gcggtcggta agttgttcc attttttgaa gcgaaggttg tggatctgga taccgggaaa   1140
acgctgggcg ttaatcagag aggcgaatta tgtgtcagag gacctatgat tatgtccggt   1200
tatgtaaaca atccggaagc gaccaacgcc ttgattgaca aggatggatg gctacattct   1260
ggagacatag cttactggga cgaagacgaa cacttcttca tagttgaccg cttgaagtct   1320
ttaattaaat acaaaggata tcaggtggcc cccgctgaat tggaatcgtt attgttacaa   1380
caccccaaca tcttcgacgc gggcgtggca ggtcttcccg acgatgacgc cggtgaactt   1440
cccgccgccg ttgttgtttt ggagcacgga aagacgatga cggaaaaaga tcgtcggat   1500 tacgtcccca gtcaagtaac aaccgcgaaa aagttgcgcg gaggagttgt gtttgtggac   1560

```
gaagtaccga aaggtcttac cggaaaactc gacgcaagaa aaatcagaga gatcctcata    1620
aaggccaaga agggcggaaa gtccaaattg taa                                 1653

<210> SEQ ID NO 11
<211> LENGTH: 1263
<212> TYPE: DNA
<213> ORGANISM: Aedes aegypti

<400> SEQUENCE: 11
cggccggagt gcgtcgtgcc ggagaaccag tgcgccatca agcggaagga gaagaaagcc     60
cagaaggaga aggacaaggt gcaaacgaac gccaccgtca gtacaacgaa cagcacctac    120
cggtcggaga tactgccgat cctgatgaaa tgtgatccac cgccgcacca agcgatacct    180
ctactaccgg aaaagctcct gcaggagaat aggctaagaa acatacctct actgacggcg    240
aaccaaatgg ccgtcattta caaactcatc tggtaccagg acgggtacga gcaaccctcg    300
gaggaagatc tcaaacggat aatgatcggt tcacccaacg aggaggaaga tcaacatgac    360
gtgcacttcc ggcacataac ggaaatcaca atcctaacag tacaactaat cgtggagttc    420
gccaagggac tgccagcatt taccaagatt ccacaggagg accagatcac gctgctgaag    480
gcctgctcaa gcgaggttat gatgttgcga atggcccgcc gctacgacgc tgccaccgat    540
tcgatcctgt tcgcgaacaa ccggtcctac acgagggact cctaccggat ggccggcatg    600
gcggacacga tagaggacct gctgcacttc tgccggcaga tgttctccct cacggtagac    660
aacgtcgagt acgcactcct cacggcgata gtcatcttct cggatcggcc cggactggag    720
caagccgaac tggtcgagca catccagagc tactacatcg acacgctgcg gatctacatc    780
ctgaataggc acgcgggcga tccgaagtgc agtgtgatat tcgccaaact gctgtcgatc    840
ctgacggagc tccgaacgct gggcaaccag aactcggaga tgtgcttctc gctcaagctg    900
aagaaccgca aactgccacg gttcctggag gagatctggg acgtccagga cataccgccc    960
tcgatgcagg cccagatgca cagccatggc acccagtcct cgtcctcatc gtcctccagt   1020
agtagtagta gtagtaacgg tagtagtaac ggtaacagta gtagtaatag taatagttca   1080
cagcacgggc cacatccgca tccgcacggg cagcaattaa cgccaaatca gcagcagcat   1140
cagcagcagc acagtcagtt acagcaagtt cacgccaacg gcagcggaag tggtggcggc   1200
agtaacaata atagcagtag tgggggcgta gtcccgggcc tcggcatgct cgaccaggta   1260
tag                                                                 1263

<210> SEQ ID NO 12
<211> LENGTH: 948
<212> TYPE: DNA
<213> ORGANISM: Amblyomma americanum

<400> SEQUENCE: 12
cggccggaat gtgtggtgcc ggagtaccag tgtgccatca agcgggagtc taagaagcac     60
cagaaggacc ggccaaacag cacaacgcgg gaaagtccct cggcgctgat ggcgccatct    120
tctgtgggtg gcgtgagccc caccagccag cccatgggtg gcgaggcag ctccctgggc     180 agcagcaatc acgaggagga taagaagcca gtggtgctca gcccaggagt caagcccctc    240
tcttcatctc aggaggacct catcaacaag ctagtctact accagcagga gtttgagtcg    300
ccttctgagg aagacatgaa gaaaaccacg cccttccccc tgggagacag tgaggaagac    360
aaccagcggc gattccagca cattactgag atcaccatcc tgacagtgca gctcattgtg    420
gagttctcca gcgggtccc tggctttgac acgctggcac gagaagacca gattactttg    480
```

```
ctgaaggcct gctccagtga agtgatgatg ctgagaggtg cccggaaata tgatgtgaag      540
acagattcta tagtgtttgc caataaccag ccgtacacga gggacaacta ccgcagtgcc      600
agtgtggggg actctgcaga tgccctgttc cgcttctgcc gcaagatgtg tcagctgaga      660
gtagacaacg ctgaatacgc actcctgacg gccattgtaa ttttctctga acggccatca      720
ctggtggacc cgcacaaggt ggagcgcatc caggagtact acattgagac cctgcgcatg      780
tactccgaga accaccggcc cccaggcaag aactactttg cccggctgct gtccatcttg      840
acagagctgc gcaccttggg caacatgaac gccgaaatgt gcttctcgct caaggtgcag      900
aacaagaagc tgccaccgtt cctggctgag atttgggaca tccaagag                   948
```

```
<210> SEQ ID NO 13
<211> LENGTH: 1586
<212> TYPE: DNA
<213> ORGANISM: Bamecia argentifoli

<400> SEQUENCE: 13
gaattcgcgg ccgctcgcaa acttccgtac ctctcacccc ctcgccagga cccccgcca      60 accagttcac cgtcatctcc tccaatggat actcatcccc catgtcttcg ggcagctacg     120
acccttatag tcccaccaat ggaagaatag ggaaagaaga gctttcgccg gcgaatagtc     180
tgaacgggta caacgtggat agctgcgatg cgtcgcggaa gaagaaggga ggaacgggtc     240
ggcagcagga ggagctgtgt ctcgtctgcg gggaccgcgc ctccggctac cactacaacg     300
ccctcacctg cgaaggctgc aagggcttct tccgtcggag catcaccaag aatgccgtct     360
accagtgtaa atatggaaat aattgtgaaa ttgacatgta catgaggcga aaatgccaag     420
agtgtcgtct caagaagtgt ctcagcgttg gcatgaggcc agaatgtgta gttcccgaat     480
tccagtgtgc tgtgaagcga aaagagaaaa aagcgcaaaa ggacaaagat aaacctaact     540
caacgacgag ttgttctcca gatgaatca aacaagagat agatcctcaa aggctggata     600
cagattcgca gctattgtct gtaaatggag ttaaacccat tactccagag caagaagagc     660
tcatccatag gctagtttat tttcaaaatg aatatgaaca tccatcccca gaggatatca     720
aaaggatagt taatgctgca ccagaagaag aaaatgtagc tgaagaaagg tttaggcata     780
ttacagaaat tacaattctc actgtacagt taattgtgga attttctaag cgattacctg     840
gttttgacaa actaattcgt gaagatcaaa tagctttatt aaaggcatgt agtagtgaag     900
taatgatgtt tagaatggca aggaggtatg atgctgaaac agattcgata ttgtttgcaa     960
ctaaccagcc gtatacgaga gaatcataca ctgtagctgg catgggtgat actgtggagg    1020
atctgctccg attttgtcga catatgtgtg ccatgaaagt cgataacgca gaatatgctc    1080
ttctcactgc cattgtaatt ttttcagaac gaccatctct aagtgaaggc tggaaggttg    1140
agaagattca agaaatttac atagaagcat taaaagcata tgttgaaaat cgaaggaaac    1200
catatgcaac aaccattttt gctaagttac tatctgtttt aactgaacta cgaacattag    1260
ggaatatgaa ttcagaaaca tgcttctcat tgaagctgaa gaatagaaag gtgccatcct    1320
tcctcgagga gatttgggat gttgtttcat aaacagtctt acctcaattc catgttactt    1380
ttcatatttg atttatctca gcaggtggct cagtacttat cctcacatta ctgagctcac    1440
ggtatgctca tacaattata acttgtaata tcatatcggt gatgacaaat tgttacaat     1500 attcttttgtt accttaacac aatgttgatc tcataatgat gtatgaattt ttctgttttt    1560
gcaaaaaaaa aagcggccgc gaattc                                           1586
```

```
<210> SEQ ID NO 14
```

```
<211> LENGTH: 1650
<212> TYPE: DNA
<213> ORGANISM: Drosophila melanogaster

<400> SEQUENCE: 14
cggccggaat gcgtcgtccc ggagaaccaa tgtgcgatga agcggcgcga aaagaaggcc      60
cagaaggaga aggacaaaat gaccacttcg ccgagctctc agcatggcgg caatggcagc     120
ttggcctctg gtggcggcca agactttgtt aagaaggaga ttcttgacct tatgacatgc     180
gagccgcccc agcatgccac tattccgcta ctacctgatg aaatattggc caagtgtcaa     240
gcgcgcaata taccttcctt aacgtacaat cagttggccg ttatatacaa gttaatttgg     300
taccaggatg gctatgagca gccatctgaa gaggatctca ggcgtataat gagtcaaccc     360
gatgagaacg agagccaaac ggacgtcagc tttcggcata taaccgagat aaccatactc     420
acggtccagt tgattgttga gtttgctaaa ggtctaccag cgtttacaaa gatacccag      480 gaggaccaga tcacgttact aaaggcctgc tcgtcggagg tgatgatgct gcgtatggca     540
cgacgctatg accacagctc ggactcaata ttcttcgcga ataatagatc atatacgcgg     600
gattcttaca aaatggccgg aatggctgat aacattgaag acctgctgca tttctgccgc     660
caaatgttct cgatgaaggt ggacaacgtc gaatacgcgc ttctcactgc cattgtgatc     720
ttctcggacc ggccgggcct ggagaaggcc caactagtcg aagcgatcca gagctactac     780
atcgacacgc tacgcattta tatactcaac cgccactgcg gcgactcaat gagcctcgtc     840
ttctacgcaa agctgctctc gatcctcacc gagctgcgta cgctgggcaa ccagaacgcc     900
gagatgtgtt tctcactaaa gctcaaaaac cgcaaactgc ccaagttcct cgaggagatc     960
tgggacgttc atgccatccc gccatcggtc cagtcgcacc ttcagattac ccaggaggag    1020
aacgagcgtc tcgagcgggc tgagcgtatg cgggcatcgg ttgggggcgc cattaccgcc    1080
ggcattgatt gcgactctgc ctccacttcg gcggcggcag ccgcggccca gcatcagcct    1140
cagcctcagc cccagcccca accctcctcc ctgacccaga acgattccca gcaccagaca    1200
cagccgcagc tacaacctca gctaccacct cagctgcaag gtcaactgca accccagctc    1260
caaccacagc ttcagacgca actccagcca cagattcaac cacagccaca gctccttccc    1320
gtctccgctc ccgtgcccgc ctccgtaacc gcacctggtt ccttgtccgc ggtcagtacg    1380
agcagcgaat acatgggcgg aagtgcggcc ataggaccca tcacgccggc aaccaccagc    1440
agtatcacgg ctgccgttac cgctagctcc accacatcag cggtaccgat gggcaacgga    1500
gttggagtcg gtgttggggt gggcggcaac gtcagcatgt atgcgaacgc ccagacggcg    1560
atggccttga tgggtgtagc cctgcattcg caccaagagc agcttatcgg gggagtggcg    1620
gttaagtcgg agcactcgac gactgcatag                                     1650

<210> SEQ ID NO 15
<211> LENGTH: 2840
<212> TYPE: DNA
<213> ORGANISM: Manduca sexta

<400> SEQUENCE: 15
tccgttgacg acggtcgcac gcgtgcaacg tgctcgtttt tacggctcaa gcgaacgcgt      60
aacctccgtc tccacatcac cgagcgaact ctagaactcg cgtactcttc tcacctgttg     120
cttcggattg tgttgtgact gaaaagcgac gcgtatcgtg gtcgaagatt ctctataagt     180
gcataatata ttcgagacag tggatagcga ttcgtttcgg tttcatcgcg cggatgagtg     240
gttcatgccc gtagagacgc gtttagatag ttatggcgag gaaaaagtga agtgaaagcc     300
```

```
tacgtcagag gatgtccctc ggtggtcacg gaagccgggg cgtgtgacgc gctcttcgac      360
atgagacgcc gctggtcaaa caacggatgt ttccctctgc gaatgtttga ggagagctcc      420
tctgaagtga cttcttcctc ggcgttcggg atgccggcgg ccatggtaat gtcaccggag      480
tcgctggcgt cgccagagta cggcggcctc gagctctgga gctacgatga gaccatgaca      540
aactatccgg cgcagtcact gctcggcgcg tgtaatgcgc cgcagcagca gcagcaacag      600
caacaacagc agccgtccgc tcagccgctg ccgtctatgc cgctgccgat gcctcctaca      660
actcctaaat cagagaacga gtccatgtcg tcaggtcgag aagaattatc accggcctca      720
agtataaatg gatgtagtac tgatggggaa ccaagacgac agaagaaagg ccagcgccg       780 cgccagcagg aggaactgtg ccttgtttgc ggcgacaggg cttcgggata tcactataac      840
gcgcttacgt gcgaaggatg taaagggttc ttcaggcgga gtgtgaccaa gaatgcggta      900
tatatttgta aatttggaca cgcctgcgag atggacatgt acatgaggag aaaatgccaa      960
gagtgtcggt tgaagaaatg cctcgcggtg ggcatgaggc ccgagtgcgt cgtcccagag     1020
tccacgtgca agaacaaaag aagagaaaag gaagcacaga gagaaaaaga caaactgcca     1080
gtcagtacga cgacagtgga cgatcatatg cctgccataa tgcaatgtga ccctccgccc     1140
ccagaggcgg caaggattca cgaagtggtc ccgaggttcc taacggagaa gctaatggag     1200
cagaacagac tgaagaatgt gacgccgctg tcggcgaacc agaagtccct gatcgcgagg     1260
ctcgtgtggt accaggaggg gtacgagcag ccgtcggagg aagatctcaa gagagttaca     1320
cagacatggc agttagaaga agaagaagag gaggaaactg acatgccctt ccgtcagatc     1380
acagagatga cgatcttaac agtgcagctt attgtagaat tcgcaaaggg actaccggga     1440
ttctccaaga tatctcagtc cgatcaaatt acattattaa aggcgtcatc aagcgaagtg     1500
atgatgctgc gagtggcgcg acggtacgac gcggcgacga cagcgtgct  gttcgcgaac     1560 aaccaggcgt acacgcgcga caactaccgc aaggcgggca tgtcctacgt catcgaggac     1620
ctgctgcact tctgtcggtg tatgtactcc atgagcatgg acaatgtgca ctacgcgctg     1680
ctcaccgcca tcgttatatt ctcagaccgg ccaggcctcg agcaaccccct tttagtggag     1740 gaaatccaga gatactactt gaagacgctg cgggtttaca tttttaaatca gcacagcgcg     1800 tcgcctcgct gcgccgtgct gttcggcaag atcctcggcg tgctgacgga actgcgcacg     1860
ctcggcacgc agaactccaa catgtgcatc tcgctgaagc tgaagaacag gaaacttccg     1920
ccattcctcg aggagatctg ggacgtggcc gaagtgtcga cgacgcagcc gacgccgggg     1980
gtggcggcgc aggtgacccc catcgtggtg gacaaccccg cggcgctcta gctggcgcgc     2040
cggcgccgcg ccccgccgcc cccgccgccg ccgctccccc gcgccgccgc gcgcgccccc     2100
cgcggcctgc gctgagtgcg ggacccgccc cgaggagaga acgctcatag actggctagt     2160
tttagtgaag tgcacggacg cgatcgtggg accgcatcga cgcgtccgtg aggacagtgc     2220
aaatattacc gctagggccg gttcgtacgt gtccggtgac cgacgacgat gatgcgcgtg     2280
agattagtga atatatgtgt tgttgaacgt ttggagagta tatttagtgt tgatcgtcgg     2340
gagcgcgcgg ccggcgcgtg tcggcgagct gtccgccgcg cgccggccgc ggcgactccg     2400 cgttttttc gtttgcgacc ggaaaccgag tcggtcactc ggatacgccc gtatgataag      2460
acttctttcg ataaataagt tcacctgtat tgcgcgtaca tacgagaatt ataaagaaaa     2520
aaagtaatat atgaagagat gtttctattg ggtgaaaagt ttaaacttat gtttatttac     2580
caaaattaac tatacgttga tcgacctttt gactataata ttgtgctggg tcgttggcag     2640
cggccgacga acgcgcgccg accatatttg tttatatata gttatgtgaa gacgttatcg     2700
```

```
tgtcgtgtcc acttagttcc gattcatgtt ccaccaggtc ggtgtagtga tcagggcggg      2760
ccagggtgac ggccaccacg gataacaggc aaagagcgac gaatgttttc atgttgagac      2820
tttgggagac gttattcctc                                                   2840
```

<210> SEQ ID NO 16
<211> LENGTH: 1109
<212> TYPE: DNA
<213> ORGANISM: Nephotetix cincticeps

<400> SEQUENCE: 16

```
caggaggagc tctgcctgtt gtgcggagac cgagcgtcgg gataccacta caacgctctc        60
acctgcgaag gatgcaaggg cttctttcgg aggagtatca ccaaaaacgc agtgtaccag       120
tccaaatacg gcaccaattg tgaaatagac atgtatatgc ggcgcaagtg ccaggagtgc       180
cgactcaaga agtgcctcag tgtagggatg aggccagaat gtgtagtacc tgagtatcaa       240
tgtgccgtaa aaggaaaga gaaaaaagct caaaaggaca agataaaacc tgtctcttca       300
accaatggct cgcctgaaat gagaatagac caggacaacc gttgtgtggt gttgcagagt       360
gaagacaaca ggtacaactc gagtacgccc agtttcggag tcaaacccct cagtccagaa       420
caagaggagc tcatccacag gctcgtctac ttccagaacg agtacgaaca ccctgccgag       480
gaggatctca gcggatcga gaacctcccc tgtgacgacg atgacccgtg tgatgttcgc       540
tacaaacaca ttacggagat cacaatactc acagtccagc tcatcgtgga gtttgcgaaa       600
aaactgcctg gtttcgacaa actactgaga gaggaccaga tcgtgttgct caaggcgtgt       660
tcgagcgagg tgatgatgct gcggatggcg cggaggtacg acgtccagac agactcgatc       720
ctgttcgcca acaaccagcc gtacacgcga gagtcgtaca cgatggcagg cgtgggggaa       780
gtcatcgaag atctgctgcg gttcggccga ctcatgtgct ccatgaaggt ggacaatgcc       840
gagtatgctc tgctcacggc catcgtcatc ttctccgagc ggccgaacct ggcggaagga       900
tggaaggttg agaagatcca ggagatctac ctggaggcgc tcaagtccta cgtggacaac       960
cgagtgaaac ctcgcagtcc gaccatcttc gccaaactgc tctccgttct caccgagctg      1020
cgaacactcg gcaaccagaa ctccgagatg tgcttctcgt taaactacgc aaccgcaaac      1080
atgccaccgt tcctcgaaga aatctggga                                        1109
```

<210> SEQ ID NO 17
<211> LENGTH: 894
<212> TYPE: DNA
<213> ORGANISM: Tenebrio molitor

<400> SEQUENCE: 17

```
aggccggaat gtgtggtacc ggaagtacag tgtgctgtta agagaaaaga gaagaaagcc        60
caaaaggaaa aagataaacc aaacagcact actaacggct caccagacgt catcaaaatt       120
gaaccagaat tgtcagattc agaaaaaaca ttgactaacg gacgcaatag gatatccacca     180 gagcaagagg agctcatact catacatcga ttggtttatt tccaaaacga atatgaacat       240
ccgtctgaag aagacgttaa acggattatc aatcagccga tagatggtga agatcagtgt       300
gagatacggt ttaggcatac cacggaaatt acgatcctga ctgtgcagct gatcgtggag       360
tttgccaagc ggttaccagg cttcgataag ctcctgcagg aagatcaaat tgctctcttg       420
aaggcatgtt caagcgaagt gatgatgttc aggatggccc gacgttacga cgtccagtcg       480
gattccatcc tcttcgtaaa caaccagcct tatccgaggg acagttacaa tttggccggt       540 atggggggaaa ccatcgaaga tctcttgcat tttgcagaa ctatgtactc catgaaggtg      600
```

```
gataatgccg aatatgcttt actaacagcc atcgttattt tctcagagcg accgtcgttg    660
atagaaggct ggaaggtgga gaagatccaa gaaatctatt tagaggcatt gcgggcgtac    720
gtcgacaacc gaagaagccc aagccggggc acaatattcg cgaaactcct gtcagtacta    780
actgaattgc ggacgttagg caaccaaaat tcagagatgt gcatctcgtt gaaattgaaa    840
aacaaaaagt taccgccgtt cctggacgaa atctgggacg tcgacttaaa agca          894
```

<210> SEQ ID NO 18
<211> LENGTH: 719
<212> TYPE: DNA
<213> ORGANISM: Mus musculus

<400> SEQUENCE: 18

```
ttcgagatgc ctgtggacag gatcctggag gcagagcttg ctgtggaaca gaagagtgac     60
cagggcgttg agggtcctgg gggaaccggg ggtagcggca gcagcccaaa tgaccctgtg    120
actaacatct gtcaggcagc tgacaaacag ctattcacgc ttgttgagtg ggcgaagagg    180
atcccacact tttcctcctt gcctctggat gatcaggtca tattgctgcg ggcaggctgg    240
aatgaactcc tcattgcctc cttttcacac cgatccattg atgttcgaga tggcatcctc    300
cttgccacag gtcttcacgt gcaccgcaac tcagcccatt cagcaggagt aggagccatc    360
tttgatcggg tgctgacaga gctagtgtcc aaaatgcgtg acatgaggat ggacaagaca    420
gagcttggct gcctgagggc aatcattctg tttaatccag atgccaaggg cctctccaac    480
cctagtgagg tggaggtcct gcgggagaaa gtgtatgcat cactgagac ctactgcaaa    540 cagaagtacc ctgagcagca gggacggttt gccaagctgc tgctacgtct tcctgccctc    600
cggtccattg gccttaagtg tctagagcat ctgttttctt tcaagctcat tggtgacacc    660
cccatcgaca ccttcctcat ggagatgctt gaggctcccc atcaactggc ctgaaagct    719
```

<210> SEQ ID NO 19
<211> LENGTH: 541
<212> TYPE: PRT
<213> ORGANISM: Choristoneura fumiferana

<400> SEQUENCE: 19

```
Met Arg Arg Arg Trp Ser Asn Asn Gly Gly Phe Gln Thr Leu Arg Met
1               5                   10                  15

Leu Glu Glu Ser Ser Glu Val Thr Ser Ser Ser Ala Leu Gly Leu
            20                  25                  30

Pro Ala Ala Met Val Met Ser Pro Glu Ser Leu Ala Ser Pro Glu Tyr
        35                  40                  45

Gly Gly Leu Glu Leu Trp Gly Tyr Asp Asp Gly Leu Ser Tyr Asn Thr
    50                  55                  60

Ala Gln Ser Leu Leu Gly Asn Thr Cys Thr Met Gln Gln Gln Gln Gln
65                  70                  75                  80

Thr Gln Pro Leu Pro Ser Met Pro Leu Pro Met Pro Thr Thr Pro
                85                  90                  95

Lys Ser Glu Asn Glu Ser Ile Ser Ser Gly Arg Glu Glu Leu Ser Pro
            100                 105                 110

Ala Ser Ser Ile Asn Gly Cys Ser Thr Asp Gly Glu Ala Arg Arg Gln
        115                 120                 125

Lys Lys Gly Pro Ala Pro Arg Gln Gln Glu Glu Leu Cys Leu Val Cys
    130                 135                 140

Gly Asp Arg Ala Ser Gly Tyr His Tyr Asn Ala Leu Thr Cys Glu Gly
145                 150                 155                 160
```

```
Cys Lys Gly Phe Phe Arg Arg Ser Val Thr Lys Asn Ala Val Tyr Ile
            165                 170                 175

Cys Lys Phe Gly His Ala Cys Glu Met Asp Met Tyr Met Arg Arg Lys
        180                 185                 190

Cys Gln Glu Cys Arg Leu Lys Lys Cys Leu Ala Val Gly Met Arg Pro
    195                 200                 205

Glu Cys Val Val Pro Glu Thr Gln Cys Ala Met Lys Arg Lys Glu Lys
210                 215                 220

Lys Ala Gln Lys Glu Lys Asp Lys Leu Pro Val Ser Thr Thr Thr Val
225                 230                 235                 240

Asp Asp His Met Pro Pro Ile Met Gln Cys Glu Pro Pro Pro Pro Glu
                245                 250                 255

Ala Ala Arg Ile His Glu Val Val Pro Arg Phe Leu Ser Asp Lys Leu
            260                 265                 270

Leu Glu Thr Asn Arg Gln Lys Asn Ile Pro Gln Leu Thr Ala Asn Gln
        275                 280                 285

Gln Phe Leu Ile Ala Arg Leu Ile Trp Tyr Gln Asp Gly Tyr Glu Gln
    290                 295                 300

Pro Ser Asp Glu Asp Leu Lys Arg Ile Thr Gln Thr Trp Gln Gln Ala
305                 310                 315                 320

Asp Asp Glu Asn Glu Glu Ser Asp Thr Pro Phe Arg Gln Ile Thr Glu
                325                 330                 335

Met Thr Ile Leu Thr Val Gln Leu Ile Val Glu Phe Ala Lys Gly Leu
            340                 345                 350

Pro Gly Phe Ala Lys Ile Ser Gln Pro Asp Gln Ile Thr Leu Leu Lys
        355                 360                 365

Ala Cys Ser Ser Glu Val Met Met Leu Arg Val Ala Arg Arg Tyr Asp
370                 375                 380

Ala Ala Ser Asp Ser Val Leu Phe Ala Asn Asn Gln Ala Tyr Thr Arg
385                 390                 395                 400

Asp Asn Tyr Arg Lys Ala Gly Met Ala Tyr Val Ile Glu Asp Leu Leu
                405                 410                 415

His Phe Cys Arg Cys Met Tyr Ser Met Ala Leu Asp Asn Ile His Tyr
            420                 425                 430

Ala Leu Leu Thr Ala Val Val Ile Phe Ser Asp Arg Pro Gly Leu Glu
        435                 440                 445

Gln Pro Gln Leu Val Glu Glu Ile Gln Arg Tyr Tyr Leu Asn Thr Leu
    450                 455                 460

Arg Ile Tyr Ile Leu Asn Gln Leu Ser Gly Ser Ala Arg Ser Ser Val
465                 470                 475                 480

Ile Tyr Gly Lys Ile Leu Ser Ile Leu Ser Glu Leu Arg Thr Leu Gly
                485                 490                 495

Met Gln Asn Ser Asn Met Cys Ile Ser Leu Lys Leu Lys Asn Arg Lys
            500                 505                 510

Leu Pro Pro Phe Leu Glu Glu Ile Trp Asp Val Ala Asp Met Ser His
        515                 520                 525

Thr Gln Pro Pro Pro Ile Leu Glu Ser Pro Thr Asn Leu
530                 535                 540

<210> SEQ ID NO 20
<211> LENGTH: 37
<212> TYPE: DNA
<213> ORGANISM: Artificial Sequence
<220> FEATURE:
<223> OTHER INFORMATION: Synthetic primer
<220> FEATURE:
```

```
<221> NAME/KEY: misc_feature
<222> LOCATION: (16)..(18)
<223> OTHER INFORMATION: n is a, c, g, or t

<400> SEQUENCE: 20
gcgtacactc gcgacnnnta ccgcaaggct ggcatgg                              37

<210> SEQ ID NO 21
<211> LENGTH: 37
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(22)
<223> OTHER INFORMATION: n is a, c, g, or t

<400> SEQUENCE: 21
ccatgccagc cttgcggtan nngtcgcgag tgtacgc                              37

<210> SEQ ID NO 22
<211> LENGTH: 32
<212> TYPE: DNA
<213> ORGANISM: Artificial Sequence
<220> FEATURE:
<223> OTHER INFORMATION: Synthetic primer

<400> SEQUENCE: 22
ggtaatgatg ctccgaaccg cgcgacgata cg                                   32

<210> SEQ ID NO 23
<211> LENGTH: 32
<212> TYPE: DNA
<213> ORGANISM: Artificial Sequence
<220> FEATURE:
<223> OTHER INFORMATION: Synthetic primer

<400> SEQUENCE: 23
cgtatcgtcg cgcggttcgg agcatcatta cc                                   32

<210> SEQ ID NO 24
<211> LENGTH: 30
<212> TYPE: DNA
<213> ORGANISM: Artificial Sequence
<220> FEATURE:
<223> OTHER INFORMATION: Synthetic primer

<400> SEQUENCE: 24
gcggcctcag acagtattct gttcgcgaac                                      30

<210> SEQ ID NO 25
<211> LENGTH: 30
<212> TYPE: DNA
<213> ORGANISM: Artificial Sequence
<220> FEATURE:
<223> OTHER INFORMATION: Synthetic primer

<400> SEQUENCE: 25
gttcgcgaac agaatactgt ctgaggccgc                                      30

<210> SEQ ID NO 26
<211> LENGTH: 29
<212> TYPE: DNA
<213> ORGANISM: Artificial Sequence
<220> FEATURE:
<223> OTHER INFORMATION: Synthetic primer
```

```
<400> SEQUENCE: 26
caaggctggc atggccgagg tcatcgagg                                29

<210> SEQ ID NO 27
<211> LENGTH: 29
<212> TYPE: DNA
<213> ORGANISM: Artificial Sequence
<220> FEATURE:
<223> OTHER INFORMATION: Synthetic primer

<400> SEQUENCE: 27
cctcgatgac ctcggccatg ccagccttg                                29

<210> SEQ ID NO 28
<211> LENGTH: 17
<212> TYPE: DNA
<213> ORGANISM: Artificial Sequence
<220> FEATURE:
<223> OTHER INFORMATION: Synthetic response element of the ecdysone
      receptor
<220> FEATURE:
<221> NAME/KEY: misc_feature
<222> LOCATION: (9)..(9)
<223> OTHER INFORMATION: n is a, c, g, or t

<400> SEQUENCE: 28
rrggttcant gacacyy                                             17

<210> SEQ ID NO 29
<211> LENGTH: 13
<212> TYPE: DNA
<213> ORGANISM: Artificial Sequence
<220> FEATURE:
<223> OTHER INFORMATION: Synthetic response element of the ecdysone
      receptor
<220> FEATURE:
<221> NAME/KEY: misc_feature
<222> LOCATION: (7)..(7)
<223> OTHER INFORMATION: n is a, c, g, or t

<400> SEQUENCE: 29
aggtcanagg tca                                                 13

<210> SEQ ID NO 30
<211> LENGTH: 15
<212> TYPE: DNA
<213> ORGANISM: Artificial Sequence
<220> FEATURE:
<223> OTHER INFORMATION: Synthetic response element of the ecdysone
      receptor

<400> SEQUENCE: 30
gggttgaatg aattt                                               15
```

STEROIDAL LIGANDS AND THEIR USE IN GENE SWITCH MODULATION

REFERENCE TO SEQUENCE LISTING SUBMITTED ELECTRONICALLY

The content of the electronically submitted sequence listing (Name Sequence_Listing_ST25.txt; Size: 30.918 bytes; and Date of Creation: Mar. 16, 2009) filed with the application is incorporated herein by reference in its entirety.

FIELD OF THE INVENTION

This invention relates to the fields of steroid chemistry and controlled gene expression. More specifically, this invention relates to steroidal ligands for natural and mutated nuclear receptors and their use in a nuclear receptor-based inducible gene expression system. The invention further relates to methods of modulating the expression of a gene of interest within a host cell using these ligands and corresponding gene switches. The invention further relates to compositions and therapeutic compositions containing one or more steroidal ligands.

BACKGROUND OF THE INVENTION

All patents, patent applications and publications cited herein are fully incorporated by reference herein in their entirety.

Precise control of gene expression is a valuable tool for studying, manipulating, and controlling development and other physiological processes. Gene expression involves a number of specific protein-protein interactions. Transcription of DNA into RNA involves a transcriptional activator in the proximity of a promoter that controls gene transcription. Typically, a transcriptional activator is associated with a protein that has a DNA binding domain that binds to sites present in the promoter regions of genes. For gene expression to occur, a protein comprising a DNA binding domain and a transactivation domain must be brought into the correct position in the promoter region of a gene.

One transgenic approach utilizes a cell-type specific promoter to drive the expression of a transgene. A DNA construct containing the transgene is first incorporated into a host genome. When triggered by a transcriptional activator, expression of the transgene occurs in a given cell type.

Another approach is through inducible promoters. Examples include the PR1-a promoter, prokaryotic repressor-operator systems, immunosuppressive-immunophilin systems, and higher eukaryotic transcription activation systems such as steroid hormone receptor systems.

Gene regulation systems based on promoters induced by heat shock, interferon and heavy metals have been described (Wurn et al., 1986, Proc. Natl. Acad. Sci. USA 83:5414-5418; Arnheiter et al., 1990 Cell 62:51-61; Filmus et al., 1992 Nucleic Acids Research 20:27550-27560). However, these systems are leaky and have limitations due to their effect on expression of non-target genes.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-β-D-thiogalactoside. The use of such systems in plants and animals is restricted by unstable chemistry of the ligands (tetracycline and lactose), their toxicity, their natural presence, or the relatively high levels required for induction or repression.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulting from fusion of FK506-cyclosporine (FKCsA) can then be used to induce dimerization of these molecules (Spencer et al., 1993, *Science* 262:1019-24; Belshaw et al., 1996 *Proc Natl Acad Sci USA* 93:4604-7). Gal4 DNA-binding domain fused to FKBP12 and VP16 activator domain fused to cyclophilin, and FKCsA compound were used to show heterodimerization and activation of a reporter gene under the control of a promoter containing Gal-4-binding sites. This system includes immunosuppressants that can have unwanted side effects resulting in limited utility in mammalian gene switch applications.

Transcription activation systems such as steroid hormone receptor systems have also been employed. Steroid hormone receptors are members of a nuclear receptor superfamily and are found in vertebrate and invertebrate cells.

Growth, molting, and development in insects are regulated by the ecdysteroid hormones (molting hormones) and the juvenile hormones (Dhadialla, et al., 1998. Annu. Rev. Entomol. 43: 545-569). The molecular target for ecdysteroids in insects include ecdysteroid receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A, as well as non-steroidal compounds including commercially available tebufenozide and methoxyfenozide (see PCT/EP96/00686 and U.S. Pat. No. 5,530,028).

The insect ecdysteroid receptor (EcR) heterodimerizes with Ultraspiracle (USP, the insect homologue of the mammalian RXR), binds ecdysteroids, binds ecdysteroid receptor DNA response elements, and activates transcription of ecdysteroid responsive genes. The EcR/USP/ligand complexes play important roles during insect development and reproduction. The EcR is a member of the steroid hormone receptor superfamily and has five modular domains, A/B (transactivation), C (DNA binding, heterodimerization), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

A version of EcR-based gene switch used *Drosophila melanogaster* EcR (DmEcR) and *Mus musculus* RXR (MmRXR) and showed that these receptors in the presence of steroid, ponasterone A, transactivate reporter genes in mammalian cell lines and transgenic mice (Christopherson K. S., Mark M. R., Bajaj V., Godowski P. J. 1992, Proc. Natl. Acad. Sci. U.S.A. 89: 6314-6318; No D., Yao T. P., Evans R. M., 1996, Proc. Natl. Acad. Sci. U.S.A. 93: 3346-3351). Later, Suhr et al. 1998, Proc. Natl. Acad. Sci. 95:7999-8004 showed that tebufenozide induced transactivation of reporter genes in mammalian cells through *Bombyx mori* EcR (BmEcR) in the absence of exogenous heterodimer partner.

PCT/US97/05330 (WO 97/38117) and PCT/US99/08381 (WO99/58155) disclose methods for modulating the expression of an exogenous gene in which a DNA construct comprising the exogenous gene and an ecdysteroid response element is activated by an ecdysteroid receptor that in the presence of a ligand and optionally in the presence of a receptor capable of acting as a silent partner. The ecdysteroid receptor was isolated from *Drosophila melanogaster*. Typically, such systems require the presence of the silent partner, such as retinoid X receptor (RXR), in order to provide optimum activation. In mammalian cells, insect ecdysteroid receptor (EcR) heterodimerizes with retinoid X receptor (RXR) and regulates expression of target genes in a ligand-dependent manner. PCT/US98/14215 (WO 99/02683) discloses that the ecdysteroid receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* USP or fragments thereof comprising at least the dimerization domain of USP for use in a gene expression system. U.S. Pat. No. 5,880,333 discloses a *Drosophila melanogaster* EcR and USP heterodimer system used in plants in which the transactivation domain and the DNA binding domain are positioned on two different hybrid proteins. These USP-based systems are constitutive in animal cells and therefore are not effective for regulating expression of a gene of interest.

In each of these cases, the transactivation domain and the DNA binding domain (either as native EcR as in PCT/US98/14215 or as modified EcR as in PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880, 333).

Therefore, a need exists in the art for improved EcR-based systems to precisely modulate the expression of endogenous or exogenous genes of interest in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to non-steroidal ligands and is insensitive to steroids, e.g., endogenous steroids. Thus, improved systems that are simple, compact, and dependent on ligands that are relatively inexpensive, readily available, and of low toxicity to the host are useful for regulating biological systems.

It has been shown that a nuclear receptor-based inducible gene expression system in which the transactivation and DNA binding domains are separated from each other by placing them on two different proteins results in greatly reduced background activity in the absence of a ligand and significantly increased activity over background in the presence of a ligand (PCT/US01/09050). This two-hybrid gene expression system is a significantly improved inducible gene expression modulation system compared to the systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283, 173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

Furthermore, the two-hybrid system avoids some side effects due to overexpression of RXR that often occur when unmodified RXR is used as a switch partner. In one example of a two-hybrid system, native DNA binding and transactivation domains of EcR or RXR are eliminated. As a result, these hybrid molecules have lower interaction with other steroid hormone receptors present in the cell resulting in reduced side effects.

With the improvement in receptor-based gene regulation systems there is increased demand for ligands with higher activity than existing ligands. Disclosed herein are novel steroidal ligands which have the ability to modulate the expression of transgenes. See Silvia Lapenna Dissertation, United Kingdom.

Additional gene switch systems owned by applicant include those described in the following, each of which are incorporated by reference: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. No. 7,304,162; U.S. Pat. No. 7,304,161.

BRIEF DESCRIPTION OF THE DRAWINGS

FIGS. 2A and 2B show structures, names and numbering of ecdysteroid ether analogues (1-23) and reference compounds (24-30).

FIG. 3 shows potency and efficacy of O-alkylated ecdysteroids (1-23) and reference compounds (24-30) measured by the *Drosophila melanogaster* $B_{II}$ bioassay (BII) and the *Cho-*

Figure 1:
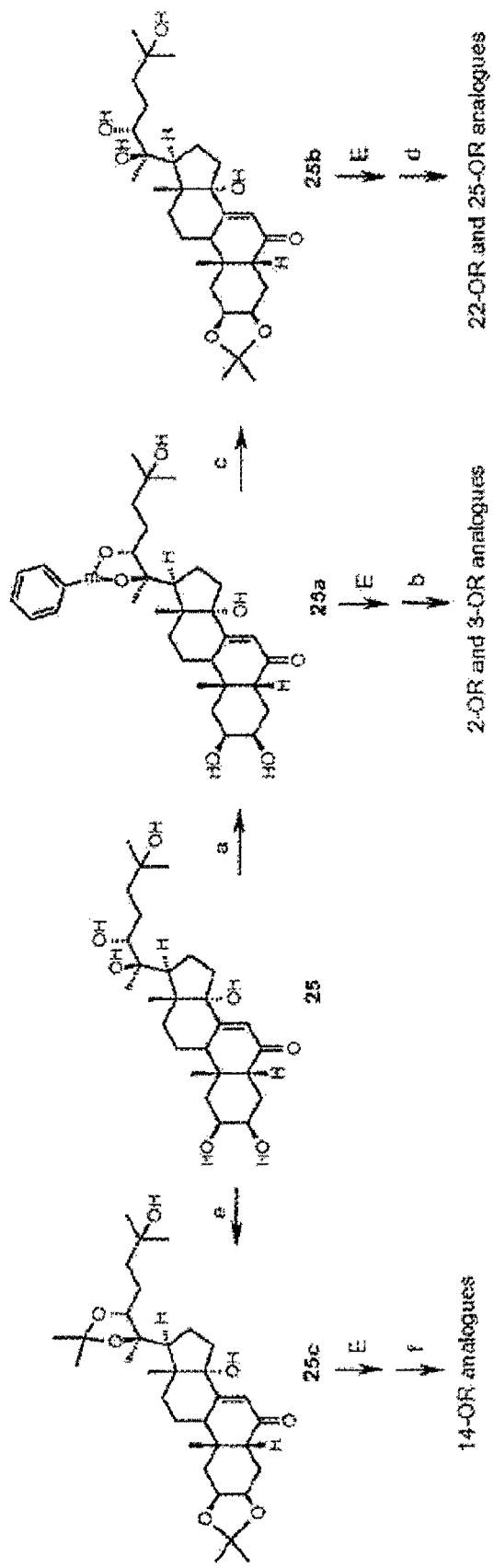
FIG. 1 shows protection/deprotection scheme for preparation of O-alkyl ethers of ecdysteroids. Prior to etherification reactions (E), the 2.3- and/or 20,22-diol groups of 20E (25) were selectively protected by transformation into the corresponding 20,22-phenylboronate (25a). 2,3-acetonide (25b) and 2.3; 14,22-diacetonide (25c) analogues. Protection/deprotection conditions: (a) phenylboronic acid (PBA). anhydrous DMF. rt. 1 h. (b) $H_2O_2$:THF 9:1 (v/v). pH=7. rt. 2.5 h. (c) 1.2.2-dimethoxypropane (DMP). dry acetone. fused p-TsOH. rt. 3 h; 2. $H_2O_2$/THF 9:1 (v/v). pH=7. rt. 2.5 h. (d) 0.1 M $HCl_{aq}$:1,4-dioxane 1:1. rt. 2.5 h. (e) DMP. dry acetone. fused p-TsOH. rt. 6 h. (f) AcOH 70%. 1,4-dioxane. reflux. 8 h. Synthesis of PoA 2,3-acetonide (26a) from PoA (26) was carried out under similar reaction conditions.
Figures 4A, 4B, 4C, 4D:
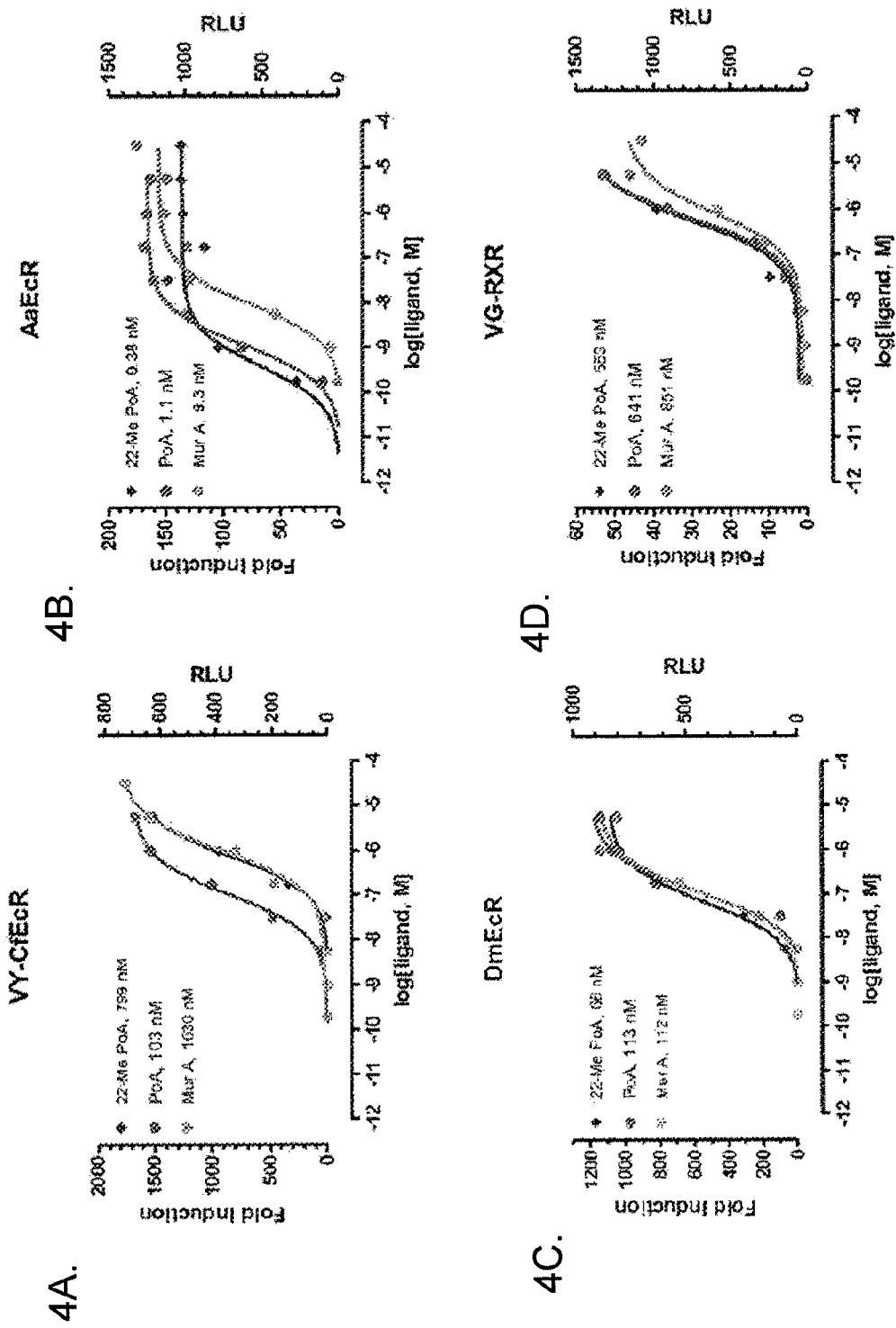

*ristoneura fumiferana* EcR-based gene switch assays using the wild-type (WT) EcR or the E274V/V390I/Y410E mutant EcR. [a]RMFI=relative maximum fold induction (relative to diacylhydrazine 30); [b]3T3 cell line; average background ~1; reference FI (1 microM)=806 (WT-CfEcR), 1012 (E274V/V390I/Y410E mutant-CfEcR).

FIGS. 4A-4D shows comparative dose-response curves of PoA 22-methyl ether, PoA, and MuA in gene switch assays based on the E274V/V390I/Y410E mutant-CfEcR, wild-type *Aedes aegypti* EcR, *Drosophila melanogaster* EcR, and the VgEcR/RXR system in mouse 3T3 fibroblasts. The reporter gene is luciferase; fold induction relative to a DMSO standard is plotted on the left axes and absolute relative light units (RLU) are plotted on the right axes. Calculated $EC_{50}$ values for each ligand and switch system appear in the figure.

FIG. 5 shows statistical summary of the 3D-QSAR model (CoMFA/CoMSIA interaction fields, leave-one-out cross-validated analysis, and conventional PLS analyses). Abbreviations: minimum σ=column filter (Kcal mol$^{-1}$), $S_{PRESS}$=standard error of prediction, $r^2$=conventional (non-validated) correlation coefficient of fit, S=standard error of estimate, $q^2$=leave-one-out cross-validated correlation coefficient, PSA=polar surface area.

FIG. 6 shows ether functional group contributions to ecdysteroid activity measured in the BII bioassay. Activity differences are expressed as Δ–log $EC_{50}$ between pairs of compounds that differ exclusively by the presence or absence of the indicated —OR substituents.

FIG. 7 shows calculated octanol-water partition coefficient, blood-brain barrier penetration, Caco-2 cell penetration, human serum albumin (HSA) binding, and aqueous solubility for a set of O-alkyl steroids. [1]Experimental logD values: 20-hydroxyecdysone, 0.01; ponasterone A, 1.95; diacylhydrazine 30, 3.4. [2]Experimental values: 20-hydroxyecdysone, 6.7 mg/mL; ponasterone A, 0.18 mg/mL; murisetone A, >2.9 mg/mL; diacylhydrazine 30 6.2 μg/mL.

FIG. 8 shows potency and efficacy of selected O-alkylated ecdysteroids and reference compounds measured by the *Aedes aegypti* (Aa) and *Drosophila melanogaster* (Dm) EcR-based gene switch assays. [a]RMFI=relative maximum fold induction (relative to diacylhydrazine 30).

FIG. 9 shows steroids with hydroxyl variations.

FIG. 10 shows steroids with side-chain variations.

FIG. 11 shows steroids with variations in oxidation state, degree of hydroxylation, ring system, and side-chain truncation.

FIG. 12 shows sequence alignment of EcR ligand-binding domains of silkworm (*Bombyx mori*, BmEcR), tobacco hornworm (*Manduca sexta*, MsEcR), spruce budworm (*Choristoneura fumiferana*, CfEcR and E274V/V390I/Y410E mutant-CfEcR, fruit fly (*Drosophila melanogaster*, DmEcR), yellow fever mosquito (*Aedes aegypti*, AaEcR), Ixodid tick (*Amblyomma americanum*, AmaEcR), silverleaf whitefly (*Bemisia argentifolii*, BaEcR), leaf hopper (*Nephotettix cincticeps*, NcEcR), and yellow meal worm (*Tenebrio molitor*, TmEcR). Helical regions are indicated above the sequence alignment. Identical residues are indicted with an asterisk; conserved residues with a colon. Residues indicated with a closed circle (conserved) or closed triangle (non-conserved) lie within 4.5 Å (heavy atoms only) of HvEcR-bound ponasterone A. Residues indicated with an open circle lie within 6.5 Å (heavy atoms only) of HvEcR-bound ponasterone A. The E274V/V390I/Y410E mutant-CfEcR are indicated in underscored boldface.

FIGS. 13A and 13B show gene switch $EC_{50}$ values for steroids as measured against lepidopteran EcRs in a two-hybrid system using GAL4-EcR (DEF regions), VP16-RXR-USP chimera, and a luciferase reporter in murine NIH 3T3 fibroblasts. FI=fold induction; RMFI, maximum fold induction relative to RSL1 maximum; "~", $EC_{50}$ assessed by visual inspection. EcR sources: BmEcR, silkworm; MsEcR, tobacco hornworm; CfEcR, spruce budworm; E274V/V390I/Y410E mutant-CfEcR.

FIGS. 14A and 14B show gene switch $EC_{50}$ values for steroids as measured against non-Lepidopteran EcRs in a two-hybrid system using GAL4-EcR (DEF regions), VP16-RXR-USP chimera, and a luciferase reporter in murine NIH 3T3 fibroblasts. BII cell transformation $EC_{50}$ values are included for comparison. FI, fold induction; RMFI, relative maximum fold induction; "~", $EC_{50}$ assessed by visual inspection. EcR sources: BII, fruit fly, DmEcR, fruit fly; AaEcR, yellow fever mosquito; AmaEcR, ixodid tick; BaEcR, silverleaf whitefly; NcEcR, leaf hopper; TmEcR, yellow meal worm.

FIG. 15 shows gene switch $EC_{50}$ values for steroids as measured against lepidopteran EcRs in a two-hybrid system using GAL4-EcR (DEF regions), VP16-RXR-USP chimera, and a luciferase reporter in murine NIH 3T3 fibroblasts. FI=fold induction; RMFI, maximum fold induction relative to RSL1 maximum; "~", $EC_{50}$ assessed by visual inspection. EcR sources: BmEcR, silkworm; MsEcR, tobacco hornworm; CfEcR, spruce budworm; E274V/V390I/Y410E mutant-CfEcR.

FIG. 16 shows gene switch $EC_{50}$ values for steroids as measured against non-Lepidopteran EcRs in a two-hybrid system using GAL4-EcR (DEF regions), VP16-RXR-USP chimera, or the VgEcR/RXR system, and a luciferase reporter in murine NIH 3T3 fibroblasts. BII cell transformation $EC_{50}$ values are included for comparison. FI, fold induction; RMFI, relative maximum fold induction; "~", $EC_{50}$ assessed by visual inspection. EcR sources: BII, fruit fly, DmEcR, fruit fly; VGECR/RXR, fruit fly; AaEcR, yellow fever mosquito; AmaEcR, ixodid tick; BaEcR, silverleaf whitefly; NcEcR, leaf hopper; TmEcR, yellow meal worm.

Figure 17:
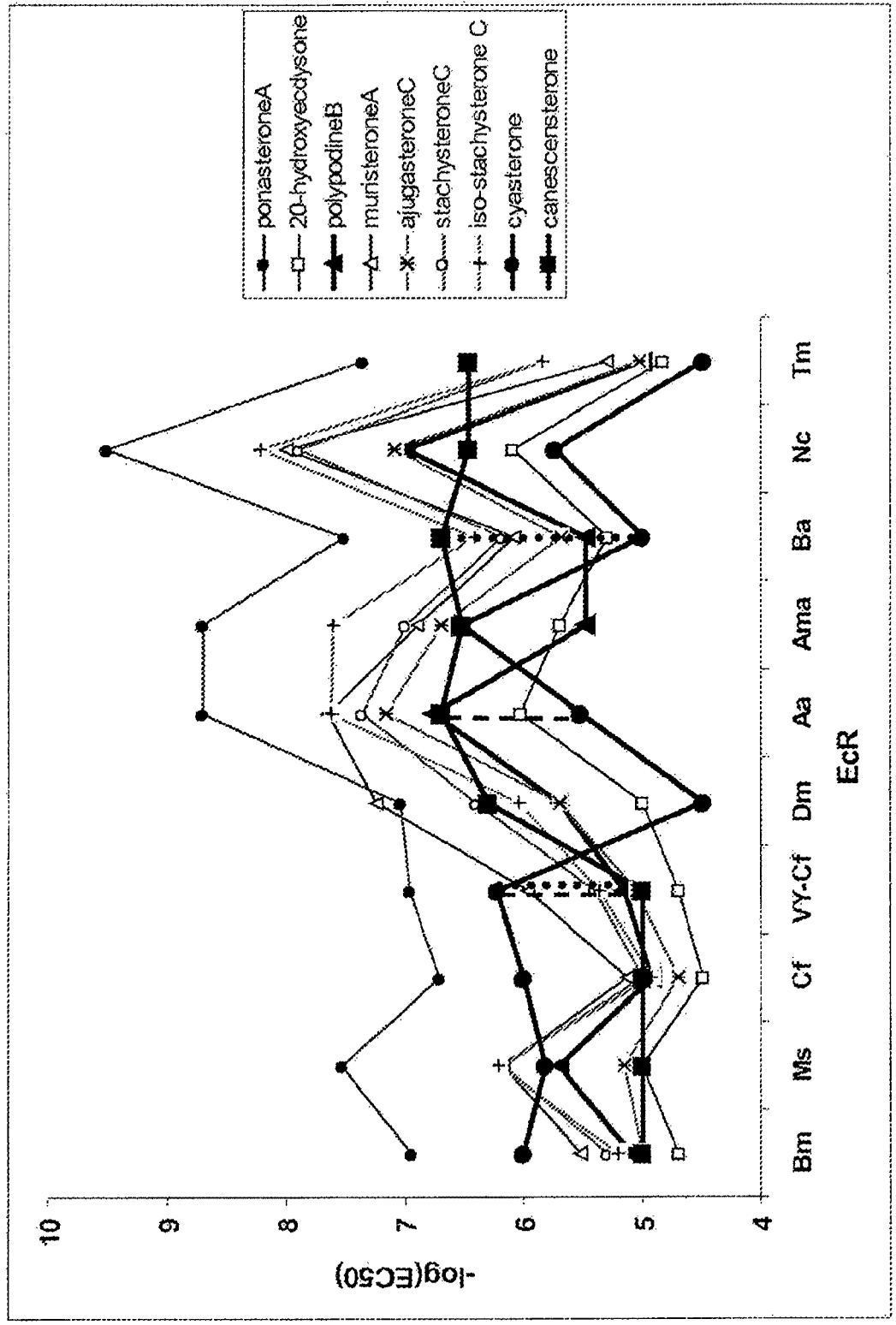

FIG. 17 shows potency level of selected steroids (–log $EC_{50}$) as a function of EcR, arranged in phylogenic order. Lepidopteran EcRs appear on the left; non-lepidoptemas on the right. Each horizontal line represents a different ligand. Cross-overs indicate an inversion of potency, i.e., an orthogonality with respect to the two ligands and EcRs on either side of the cross-over. Dotted lines indicate cyasterone/E274V/V390I/Y410E mutant-CfEcR//canescensterone/BaEcR and cyasterone/E274V/V390I/Y410E mutant-CfEcR//polypodine B/AaEcR orthogonalities.

Figure 18A:
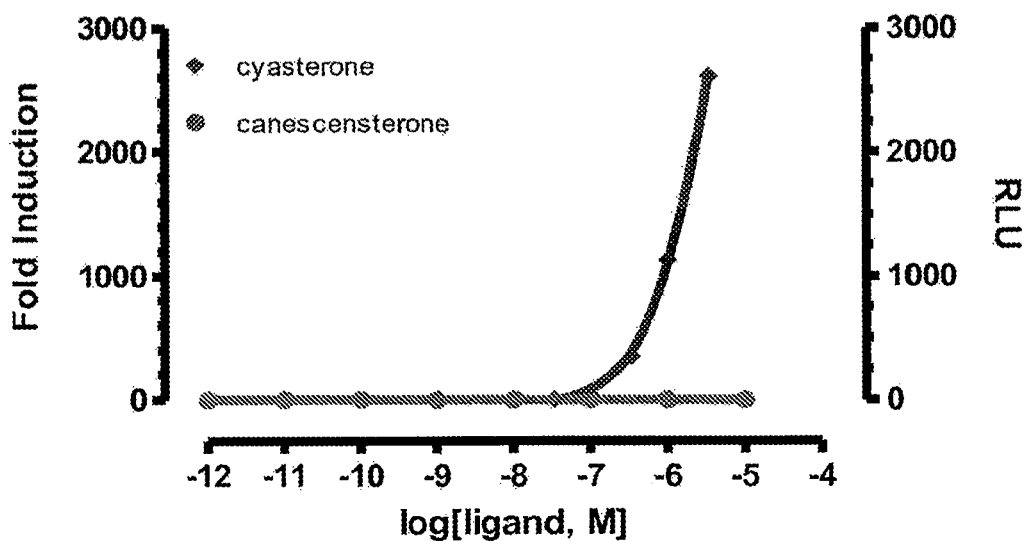
Figure 18B:
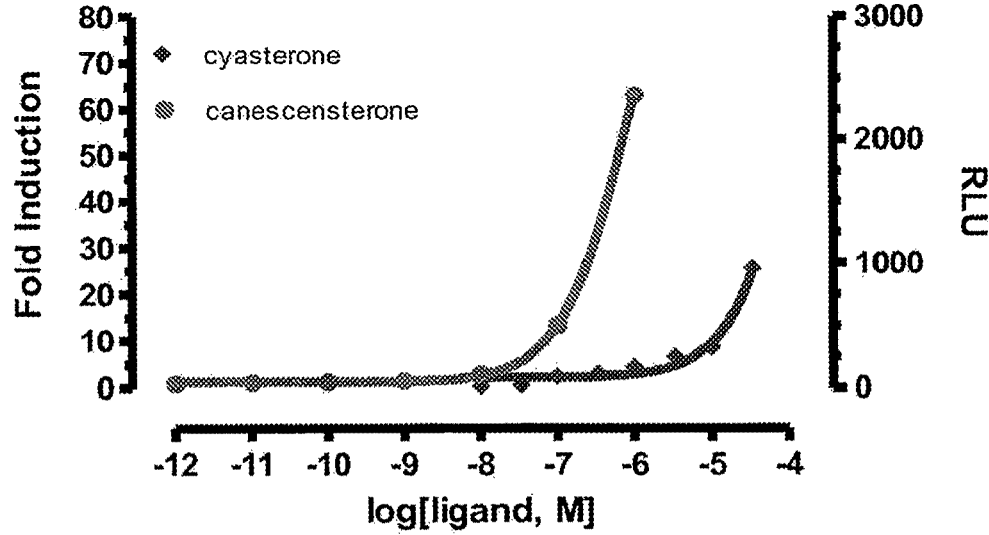

FIGS. 18A and 18B shows dose-response of cyasterone (closed circle) and canescensterone (open circle) with (a) E274V/V390I/Y410E mutant-EcR and (b) BaEcR. Fold induction (ratio of test dose RLU to background RLU) is indicated on the left vertical axis; Approximate RLU measurement is indicated on the right axis. Some points at higher doses are omitted.

Figure 19A:
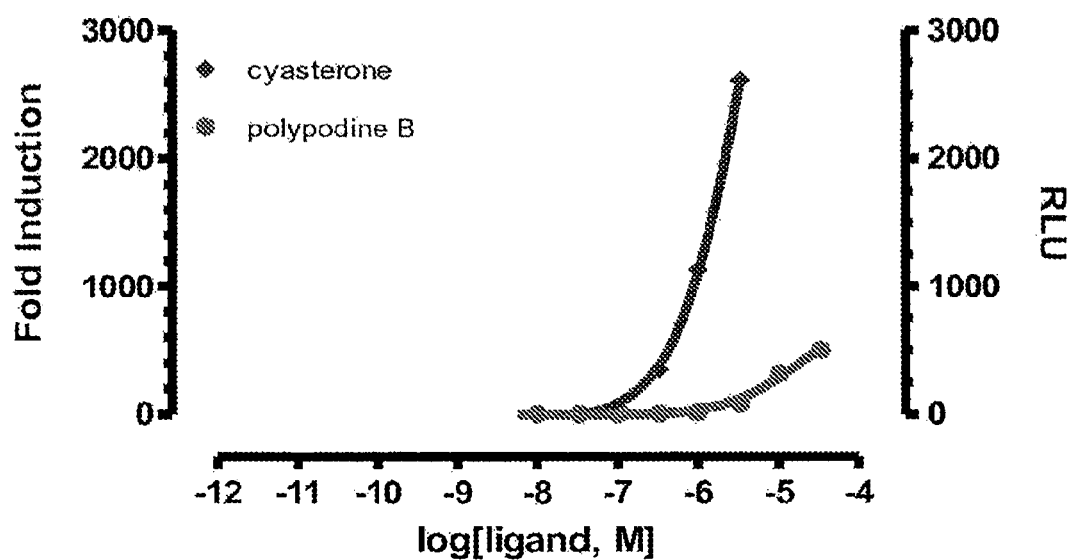
Figure 19B:
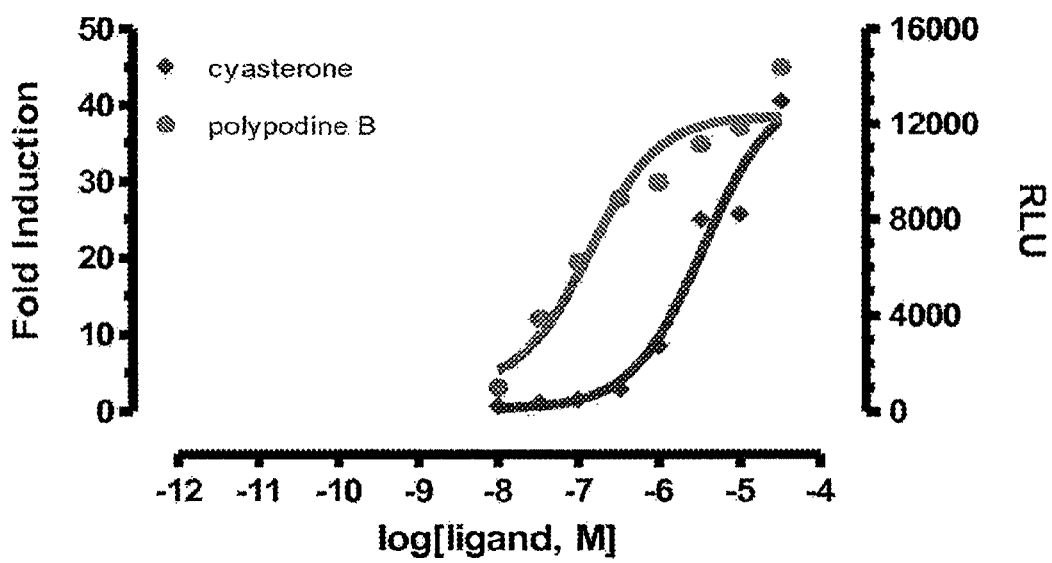

FIGS. 19A and 19B shows dose-response of cyasterone (closed circle) and polypodine B (open triangle) with (a) E274V/V390I/Y410E mutant-EcR and (b) AaEcR. Fold induction (ratio of test dose RLU to background RLU) is indicated on the left vertical axis; Approximate RLU measurement is indicated on the right axis. Some points at higher doses are omitted.

Figure 20:
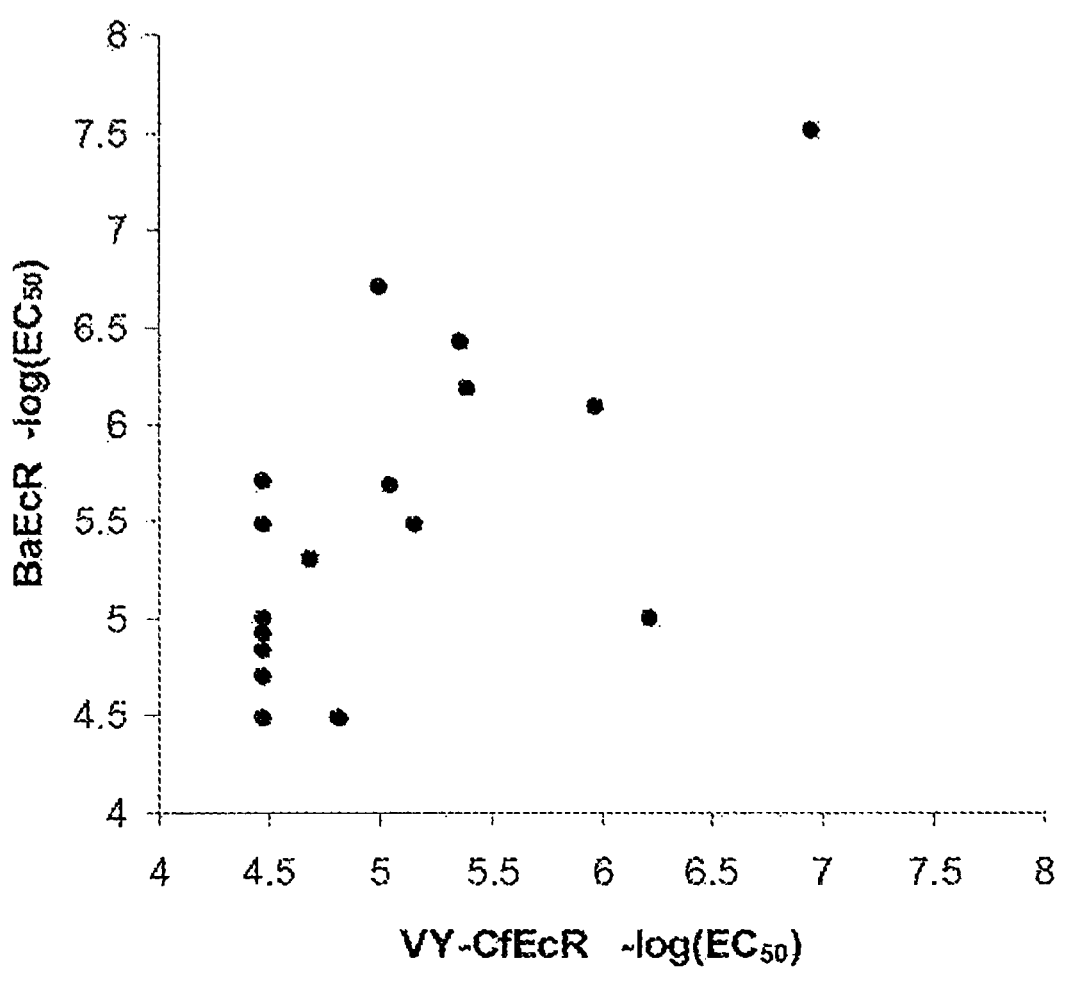

FIG. 20 shows a plot of steroid potency (–log($EC_{50}$)/–log($EC_{50}$)) of E274V/V390I/Y410E mutant-CfEcR vs. BaEcR.

SUMMARY OF THE INVENTION

The present invention relates to steroidal ligands for use with a gene switch such as a nuclear receptor-based inducible gene expression modulation system and methods of modulating the expression of a gene of interest within a host cell using these ligands in combination with a gene switch.

An embodiment of the invention relates to methods of modulating gene expression in a host cell using a gene expression modulation system with a ligand of the present invention. An aspect of the invention provides a method of modulating the expression of a gene of interest in a host cell comprising the steps of: a) introducing into the host cell a gene expression modulation system according to the invention; b) introducing into the host cell a gene expression cassette comprising i) a response element comprising a domain to which the DNA binding domain from the first hybrid polypeptide of the gene expression modulation system binds; ii) a promoter that is activated by the transactivation domain of the second hybrid polypeptide of the gene expression modulation system; and iii) a gene of interest whose expression is to be modulated; and c) introducing into the host cell a ligand; whereby upon introduction of the ligand into the host cell, expression of the gene of interest is modulated.

Another aspect of the invention includes orthogonal gene switches for independently controlling the expression of a plurality of genes of interest. Orthogonal gene switches of the invention include those based on nuclear receptors, such as steroid receptors, which include ecdysone receptors. Furthermore, orthogonal gene switches include individual switches based on wild type sequences or mutant sequences, or combinations thereof.

Another aspect of the invention includes gene switches comprising a Group H nuclear receptor ligand binding domain, an ecdysone receptor ligand binding domain, a substitution mutant of an ecdysone receptor ligand binding domain, a *Choristoneura fumiferana* ecdysone receptor ligand binding domain, a V390I/Y410E mutant of the *Choristoneura fumiferana* ecdysone receptor ligand binding domain, or a E274V/V390I/Y410E mutant of the *Choristoneura fumiferana* ecdysone receptor ligand binding domain.

Another aspect of the invention is a recombinant gene switch system comprising at least one gene switch; and at least one activating ligand, wherein the activating ligand is any one or more of the compounds disclosed herein or a non-steroidal compound, or a diacylhydrazine, an amidoketone, or an oxadiazoline.

Another aspect of the invention is a system comprising a plurality of gene switches, wherein the plurality of gene switches are encoded by one or more nucleic acids present in the same vector polynucleotide.

Another aspect of the invention is a recombinant gene switch system wherein each individually operable gene switch controls a different gene of interest; wherein the gene of interest is a therapeutic gene of interest, a cytokine, and/or a toxin.

Another aspect of the invention is a method of activating a recombinant gene switch system by administering an effective amount of a compound disclosed herein, wherein the recombinant gene switch system is responsive to said compound.

Another aspect of the invention relates to compositions and therapeutic compositions containing one or more steroidal ligands. Additional aspects of the invention include compositions comprising gene switch ligands of steroidal and/or non-steroidal structures. Such compositions encompass therapeutic mixtures.

DETAILED DESCRIPTION OF THE INVENTION

An embodiment of the invention provides ligands for use with steroid receptor-based inducible gene expression systems useful for modulating expression of a gene of interest in a host cell. In one embodiment, the invention provides a gene switch system that has a reduced level of background gene expression and responds to sub-micromolar concentrations of steroidal ligand. This invention overcomes limitations of currently available inducible expression systems and provides an effective way to control gene expression.

The invention is useful for applications such as gene therapy, large scale production of proteins and antibodies, cell-based high throughput screening assays, functional genomics, proteomics, metabolomics, and regulation of traits in transgenic organisms, where control of gene expression levels is desirable. An advantage of the invention is that expression levels can be tailored to suit the user's requirements.

The present invention pertains to compounds of the formula:

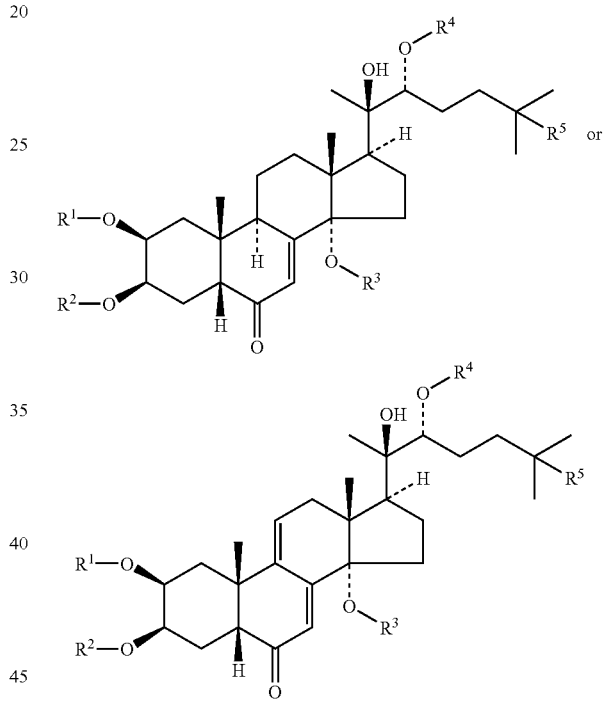

wherein $R^1$, $R^2$, $R^3$, and $R^4$ are:

a) H, $(C_1$-$C_6)$alkyl; $(C_1$-$C_6)$haloalkyl; $(C_1$-$C_6)$cyanoalkyl; $(C_1$-$C_6)$hydroxyalkyl; $(C_1$-$C_4)$alkoxy$(C_1$-$C_6)$alkyl; $(C_2$-$C_6)$alkenyl optionally substituted with halo, cyano, hydroxyl, or $(C_1$-$C_4)$alkyl; $(C_2$-$C_6)$alkynyl optionally substituted with halo, cyano, hydroxyl, or $(C_1$-$C_4)$alkyl; $(C_3$-$C_5)$cycloalkyl optionally substituted with halo, cyano, hydroxyl, or $(C_1$-$C_4)$alkyl; oxiranyl optionally substituted with halo, cyano, or $(C_1$-$C_4)$alkyl; or b) unsubstituted or substituted benzyl wherein the substituents are independently 1 to 5H, halo, nitro, cyano, hydroxyl, $(C_1$-$C_6)$alkyl, or $(C_1$-$C_6)$alkoxy; and $R^5$ is H; OH; F; Cl; or $(C_1$-$C_6)$alkoxy.

In one embodiment, when $R^1$, $R^2$, $R^3$, and $R^4$ are H, then $R^5$ is not H or hydroxy.

In one embodiment, at least one of $R^1$, $R^2$, $R^3$, and $R^4$ is not H. In another embodiment, at least two of $R^1$, $R^2$, $R^3$, and $R^4$ are not H. In another embodiment, at least three R, $R^1$, $R^3$, and $R^4$ are not H. In another embodiment, each of $R^1$, $R^2$, $R^3$, and $R^4$ are not H.

In one embodiment, when $R^1$, $R^2$, $R^3$, and $R^4$ are H, then $R^5$ is not methoxy, when $R^1$, $R^2$, $R^3$, and $R^4$ are isopropyl, then $R^5$ is not hydroxy, and when $R^1$, $R^2$, and $R^3$ are H and $R^5$ is hydroxy, then $R^4$ is not methyl or ethyl.

In specific embodiments, $R^1$, $R^2$, $R^3$, and $R^4$ are:

a) H, $(C_1$-$C_6)$alkyl; $(C_1$-$C_6)$haloalkyl; $(C_1$-$C_6)$cyanoalkyl; $(C_1$-$C_6)$hydroxyalkyl; $(C_1$-$C_4)$alkoxy$(C_1$-$C_6)$alkyl; $(C_2$-$C_6)$alkenyl; $(C_2$-$C_6)$alkynyl; oxiranyl optionally substituted with halo, cyano, or $(C_1$-$C_4)$alkyl; or b) unsubstituted or substituted benzyl wherein the substituents are independently 1 to 5H, halo, cyano, or $(C_1$-$C_6)$alkyl; and $R^5$ is H, OH, F, Cl, or $(C_1$-$C_6)$alkoxy.

In other specific embodiments, $R^1$, $R^2$, $R^3$, and $R^4$ are H, $(C_1$-$C_6)$alkyl; $(C_2$-$C_6)$alkenyl; $(C_2$-$C_6)$alkynyl; 2'-ethyloxiranyl, or benzyl; and $R^5$ is H; OH; or F.

In specific embodiments, when $R^1$, $R^2$, $R^3$, and $R^4$ are isopropyl, then $R^5$ is not hydroxyl;

when $R^5$ is H, hydroxyl, methoxy, or fluoro, then at least one of $R^1$, $R^2$, $R^3$, and $R^4$ is not H;

when only one of $R^1$, $R^2$, $R^3$, and $R^4$ is methyl, and $R^5$ is H or hydroxyl, then the remainder of $R^1$, $R^2$, $R^3$, and $R^4$ are not H;

when both $R^4$ and one of $R^1$, $R^2$, and $R^3$ are methyl, then $R^5$ is neither H nor hydroxyl;

when $R^1$, $R^2$, $R^3$, and $R^4$ are all methyl, then $R^5$ is not hydroxyl; and when $R^1$, $R^2$, and $R^3$ are all H and $R^5$ is hydroxyl, then $R^4$ is not ethyl, n-propyl, n-butyl, allyl, or benzyl Embodiments of the invention also relate to methods of modulating expression of a gene of interest comprising contacting a nuclear receptor complex comprising:

a) a DNA binding domain;
b) a ligand binding domain;
c) a transactivation domain; and
d) a ligand;

with a DNA construct comprising:

a gene of interest; and
a response element;

wherein the gene of interest is under the control of the response element; and binding of the DNA binding domain to the response element in the presence of the ligand results in activation or suppression of the gene of interest.

In one embodiment, the ligand is a compound of the formula:

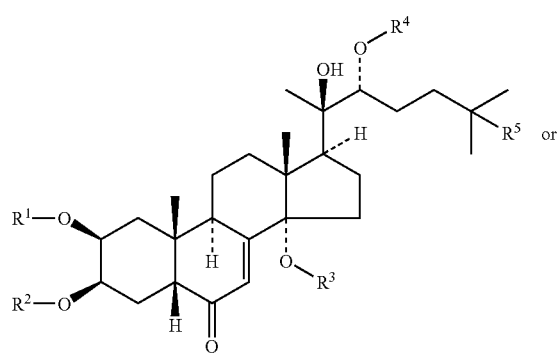 or

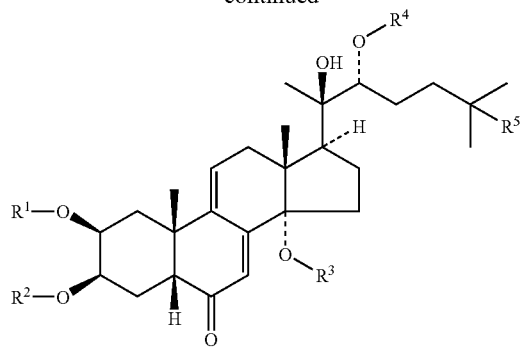

wherein $R^1$, $R^2$, $R^3$, $R^4$, and $R^5$ have the meanings as described above.

Specific embodiments of the invention include the use of the following steroidal gene switch ligands: 20-hydroxyecdysone, 2-methyl ether; 20-hydroxyecdysone, 3-methyl ether; 20-hydroxyecdysone, 14-methyl ether; 20-hydroxyecdysone, 2,22-dimethyl ether; 20-hydroxyecdysone, 3,22-dimethyl ether; 20-hydroxyecdysone, 14,22-dimethyl ether; 20-hydroxyecdysone, 22,25-dimethyl ether; 20-hydroxyecdysone, 2,3,14,22-tetramethyl ether; 20-hydroxyecdysone, 22-n-propyl ether; 20-hydroxyecdysone, 22-n-butyl ether; 20-hydroxyecdysone, 22-allyl ether; 20-hydroxyecdysone, 22-benzyl ether; 20-hydroxyecdysone, 22-(28R,S)-2'-ethyloxiranyl ether; ponasterone A, 2-methyl ether; ponasterone A, 14-methyl ether; ponasterone A, 22-methyl ether; ponasterone A, 2,22-dimethyl ether; ponasterone A, 3,22-dimethyl ether; ponasterone A, 14,22-dimethyl ether; dacryhainansterone, 22-methyl ether.

Additional embodiments of the invention include the use of the following steroidal gene switch ligands: 25,26-didehydroponasterone A, (iso-stachysterone C (Δ25(26))), shidasterone (stachysterone D), stachysterone C, 22-deoxy-20-hydroxyecdysone (taxisterone), ponasterone A, polyporusterone B, 22-dehydro-20-hydroxyecdysone, ponasterone A 22-methyl ether, 20-hydroxyecdysone, pterosterone, (25R)-inokosterone, (25S)-inokosterone, pinnatasterone, 25-fluoroponasterone A, 24(28)-dehydromakisterone A, 24-epi-makisterone A, makisterone A, 20-hydroxyecdysone-22-methyl ether, 20-hydroxyecdysone-25-methyl ether, abutasterone, 22,23-di-epi-geradiasterone, 20,26-dihydroxyecdysone (podecdysone C), 24-epi-abutasterone, geradiasterone, 29-norcyasterone, ajugasterone B, 24(28)[Z]-dehydroamarasterone B, amarasterone A, makisterone C, rapisterone C, 20-hydroxyecdysone-22,25-dimethyl ether, 20-hydroxyecdysone-22-ethyl ether, carthamosterone, 24(25)-dehydroprecyasterone, leuzeasterone, cyasterone, 20-hydroxyecdysone-22-allyl ether, 24(28)[Z]-dehydro-29-hydroxymakisterone C, 20-hydroxyecdysone-22-acetate, viticosterone E (20-hydroxyecdysone 25-acetate), 20-hydroxyecdysone-22-n-propyl ether, 24-hydroxycyasterone, 20-hydroxyecdysone-22-n-butyl ether, ponasterone A 22-hemisuccinate, 22-acetoacetyl-20-hydroxyecdysone, 20-hydroxyecdysone-22-benzyl ether, canescensterone, 20-hydroxyecdysone-22-hemisuccinate, inokosterone-26-hemisuccinate, 20-hydroxyecdysone-22-benzoate, 20-hydroxyecdysone-22-β-D-glucopyranoside, 20-hydroxyecdysone-25-β-D-glucopyranoside, sileneoside A (20-hydroxyecdysone-22α-galactoside), 3-deoxy-1β,20-dihydroxyecdysone (3-deoxyintegristerone A), 2-deoxyintegristerone A, 1-epi-integristerone A, integristerone A, sileneoside C (integristerone A 22α-galactoside), 2,22-dideoxy-20-hydroxyecdysone, 2-deoxy-20-hydroxyecdysone, 2-deoxy-20-hydroxyecdysone-3-acetate, 2-deoxy-20,26-dihydroxyecdysone, 2-deoxy-20-hydroxyecdysone-22-acetate, 2-deoxy-20-hydroxyecdysone-3,22-diacetate, 2-deoxy-20-hydroxyecdysone-22-benzoate, ponasterone A 2-hemisuccinate, 20-hydroxyecdysone-2-methyl ether, 20-hydroxyecdysone-2-acetate, 20-hydroxyecdysone-2-hemisuccinate, 20-hydroxyecdysone-2-β-D-glucopyranoside, 2-dansyl-20-hydroxyecdysone, 20-hydroxyecdysone-2,22-dimethyl ether, ponasterone A 3β-D-xylopyranoside (limnantheoside B), 20-hydroxyecdysone-3-methyl ether, 20-hydroxyecdysone-3-acetate, 20-hydroxyecdysone-3β-D-xylopyranoside (limnantheoside A), 20-hydroxyecdysone-3-β-D-glucopyranoside, sileneoside D (20-hydroxyecdysone-3α-galactoside), 20-hydroxyecdysone 3β-D-glucopyranosyl-[1-3]-β-D-xylopyranoside (limnantheoside C), 20-hydroxyecdysone-3,22-dimethyl ether, cyasterone-3-acetate, 2-dehydro-3-epi-20-hydroxyecdysone, 3-epi-20-hydroxyecdysone (coronatasterone), rapisterone D, 3-dehydro-20-hydroxyecdysone, 5β-hydroxy-25,26-didehydroponasterone A, 5β-hydroxystachysterone C, 25-deoxypolypodine B, polypodine B, 25-fluoropolypodine B, 5β-hydroxyabutasterone, 26-hydroxypolypodine B, 29-norsengosterone, sengosterone, 6β-hydroxy-20-hydroxyecdysone, 6α-hydroxy-20-hydroxyecdysone, 20-hydroxyecdysone-6-oxime, ponasterone A 6-carboxymethyloxime, 20-hydroxyecdysone-6-carboxymethyloxime, ajugasterone C, rapisterone B, muristerone A, atrotosterone B, atrotosterone A, turkesterone-2-acetate, punisterone (rhapontisterone), turkesterone, atrotosterone C, 25-hydroxyatrotosterone B, 25-hydroxyatrotosterone A, paxillosterone, turkesterone-2,22-diacetate, turkesterone-22-acetate, turkesterone-11α-acetate, turkesterone-2,11α-diacetate, turkesterone-11α-propionate, turkesterone-11α-butanoate, turkesterone-11α-hexanoate, turkesterone-11α-decanoate, turkesterone-11α-laurate, turkesterone-11α-myristate, turkesterone-11α-arachidate, 22-dehydro-12β-hydroxynorsengosterone, 22-dehydro-12β-hydroxycyasterone, 22-dehydro-12β-hydroxysengosterone, 14-deoxy(14α-H)-20-hydroxyecdysone, 20-hydroxyecdysone-14-methyl ether, 14α-perhydroxy-20-hydroxyecdysone, 20-hydroxyecdysone 14,22-dimethyl ether, 20-hydroxyecdysone-2,3,14,22-tetramethyl ether, (20S)-22-deoxy-20,21-dihydroxyecdysone, 22,25-dideoxyecdysone, (22S)-20-(2,2'-dimethylfuranyl)ecdysone, (22R)-20-(2,2'-dimethylfuranyl)ecdysone, 22-deoxyecdysone, 25-deoxyecdysone, 22-dehydroecdysone, ecdysone, 22-epi-ecdysone, 24-methylecdysone (20-deoxymakisterone A), ecdysone-22-hemisuccinate, 25-deoxyecdysone-22-β-D-glucopyranoside, ecdysone-22-myristate, 22-dehydro-20-iso-ecdysone, 20-iso-ecdysone, 20-iso-22-epi-ecdysone, 2-deoxyecdysone, sileneoside E (2-deoxyecdysone 3β-glucoside; blechnoside A), 2-deoxyecdysone-22-acetate, 2-deoxyecdysone-3,22-diacetate, 2-deoxyecdysone-22-β-D-glucopyranoside, 2-deoxyecdysone 25-β-D-glucopyranoside, 2-deoxy-21-hydroxyecdysone, 3-epi-22-iso-ecdysone, 3-dehydro-2-deoxyecdysone (silenosterone), 3-dehydroecdysone, 3-dehydro-2-deoxyecdysone-22-acetate, ecdysone-6-carboxymethyloxime, ecdysone-2,3-acetonide, 14-epi-20-hydroxyecdysone-2,3-acetonide, 20-hydroxyecdysone-2,3-acetonide, 20-hydroxyecdysone-20,22-acetonide, 14-epi-20-hydroxyecdysone-2,3,20,22-diacetonide, paxillosterone-20,22-p-hydroxybenzylidene acetal, poststerone, (20R)-dihydropoststerone, (20S)dihydropoststerone, poststerone-20-dansylhydrazine, (20S)-dihydropoststerone-2,3,20-tribenzoate, (20R)-dihydropoststerone-2,3,20-tribenzoate, (20R)dihydropoststerone-2,3-acetonide, (20S)dihydropoststerone-2,3-acetonide, (5α-H)-dihydrorubrosterone, 2,14,22,25-tetradeoxy-5α-ecdysone, 5α-ketodiol, bombycosterol, 2α,3α,22S,25-tetrahydroxy-5α-cholestan-6-one, (5α-H)-2-deoxy-21-hydroxyecdysone, castasterone, 24-epi-castasterone, (5α-H)-2-deoxyintegristerone A, (5α-H)-22-deoxyintegristerone A, (5α-H)-20-hydroxyecdysone, 24,25-didehydrodacryhaninansterone, 25,26-didehydrodacryhainansterone, 5-deoxykaladasterone (dacryhainansterone), (14α-H)-14-deoxy-25-hydroxydacryhainansterone, 25-hydroxydacryhainansterone, rubrosterone, (5β-H)-dihydrorubrosterone, dihydrorubrosterone-17β-acetate, sidisterone, 20-hydroxyecdysone-2,3,22-triacetate, 14-deoxy(14β-H)-20-hydroxyecdysone, 14-epi-20-hydroxyecdysone, 9α,20-dihydroxyecdysone, malacosterone, 2-deoxypolypodine B-3-β-D-glucopyranoside, ajugalactone, cheilanthone B, 2β,3β,6α-trihydroxy-5β-cholestane, 2β,3β,6β-trihydroxy-5β-cholestane, 14-dehydroshidasterone, stachysterone B, 2β,3β,9α,20R,22R,25-hexahydroxy-5β-cholest-7,14-dien-6-one, kaladasterone, (14β-H)-14-deoxy-25-hydroxydacryhainansterone, 4-dehydro-20-hydroxyecdysone, 14-methyl-12-en-shidasterone, 14-methyl-12-en-15,20-dihydroxyecdysone, podecdysone B, 2β,3β,20R,22R-tetrahydroxy-25-fluoro-5β-cholest-8,14-dien-6-one (25-fluoropodecdysone B), calonysterone, 14-deoxy-14,18-cyclo-20-hydroxyecdysone, 9α,14α-epoxy-20-hydroxyecdysone, 9β,14β-epoxy-20-hydroxyecdysone, 9α,14α-epoxy-20-hydroxyecdysone 2,3,20,22-diacetonide, 28-homobrassinolide, iso-homobrassinolide.

An aspect of the invention encompasses utilization of the steroidal molecules described herein to control expression of a gene of interest in combination with a gene switch. A gene switch capable of controlling expression of a gene of interest according to the invention may comprise at least a fragment of an ecdysone receptor. A gene switch capable of controlling expression of a gene of interest according to the invention may alternatively comprise at least a fragment of another nuclear receptor to which the steroid molecule binds.

When an $R^x$ group is specified, wherein x represents a number 1-4, and the same $R^x$ group is also specified with an alkyl group chain length such as "$(C_1-C_3)$", it is understood that the specified chain length refers only to the cases where $R^x$ may be alkyl, and does not pertain to cases where $R^x$ may be a non-alkyl group, such as H or aryl.

The term "alkyl" includes both branched and straight chain alkyl groups. Typical alkyl groups include, for example, methyl, ethyl, n-propyl, isopropyl, n-butyl, sec-butyl, isobutyl, tert-butyl, n-pentyl, isopentyl, n-hexyl, n-heptyl, isooctyl, nonyl, and decyl.

The term "halo" refers to fluoro, chloro, bromo or iodo.

The term "haloalkyl" refers to an alkyl group substituted with one or more halo groups such as, for example, chloromethyl, 2-bromoethyl, 3-iodopropyl, trifluoromethyl, and perfluoropropyl.

The term "cycloalkyl" refers to a cyclic aliphatic ring structure, optionally substituted with alkyl, hydroxy, or halo, such as cyclopropyl, methylcyclopropyl, cyclobutyl, 2-hydroxycyclopentyl, cyclohexyl, and 4-chlorocyclohexyl.

The term "hydroxyalkyl" refers to an alkyl group substituted with one or more hydroxy groups such as, for example, hydroxymethyl and 2,3-dihydroxybutyl.

The term "alkylsulfonyl" refers to a sulfonyl moiety substituted with an alkyl group such as, for example, mesyl, and n-propylsulfonyl.

The term "alkenyl" refers to an ethylenically unsaturated hydrocarbon group, straight or branched chain, having 1 or 2 ethylenic bonds such as, for example, vinyl, allyl, 1-butenyl, 2-butenyl, isopropenyl, and 2-pentenyl.

The term "haloalkenyl" refers to an alkenyl group substituted with one or more halo groups.

The term "alkynyl" refers to an unsaturated hydrocarbon group, straight or branched, having 1 or 2 acetylenic bonds such as, for example, ethynyl and propargyl.

The term "alkylcarbonyl" refers to an alkylketo functionality, for example acetyl, n-butyryl and the like.

The term "heterocyclyl" or "heterocycle" refers to an unsubstituted or substituted; saturated, partially unsaturated, or unsaturated 5 or 6-membered ring containing one, two or three heteroatoms, for example, one or two heteroatoms independently selected from the group consisting of oxygen, nitrogen and sulfur. Examples of heterocyclyls include, for example, pyridyl, thienyl, furyl, pyrimidinyl, pyrazinyl, quinolinyl, isoquinolinyl, pyrrolyl, indolyl, tetrahydrofuryl, pyrrolidinyl, piperidinyl, tetrahydropyranyl, morpholinyl, piperazinyl, dioxolanyl, and dioxanyl.

The term "alkoxy" includes both branched and straight chain alkyl groups attached to a terminal oxygen atom. Typical alkoxy groups include, for example, methoxy, ethoxy, n-propoxy, isopropoxy, and tert-butoxy.

The term "haloalkoxy" refers to an alkoxy group substituted with one or more halo groups such as, for example chloromethoxy, trifluoromethoxy, difluoromethoxy, and perfluoroisobutoxy.

The term "alkoxyalkyl" refers to an alkyl group substituted with an alkoxy group such as, for example, isopropoxymethyl.

The term "non-steroidial compound" or "non-steroidal ligand" refers to a compound that is not derived from a 1,2-cyclopentanoperhydrophenanthrene skeleton:

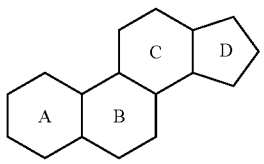

that activates a gene switches. See, for example, Akhrem, A. A. and Yu. A. Titov. *Total Steroid Synthesis*. New York: Plenum Press, 1970.

The term "diacylhydrazine" refers to a compound having a N'-substituted-N,N'-diacylhydrazine nucleus. Such a compound is disclosed, for example, in U.S. Pat. Nos. 4,985,461, 5,225,443, 5,354,762, 5,117,057, 6,013,836, 5,424,333, 5,344,958, 5,530,028, 5,482,962, 7,456,315 and 7,304,161, and WO 2008/153801. In one embodiment, the term "diacylhydrazine" refers to a compound having the formula:

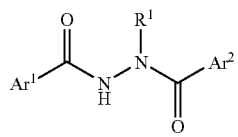

wherein $R^1$ is alkyl, and $Ar^1$ and $Ar^2$ are independently phenyl having 1-3 substituents selected from the group consisting of halogen, alkyl, and alkoxy. In one embodiment $R^1$ is a branched $C_4$-$C_8$ alkyl, e.g., —C(CH$_3$)$_3$, —C(CH$_3$)C(CH$_3$)$_3$, —C(CH$_2$CH$_3$)C(CH$_3$)$_3$, or —C(CH$_2$CH$_2$CH$_3$)C(CH$_3$)$_3$. In one embodiment, the phenyl substituents are independently $C_1$-$C_4$ alkyl or alkoxy, e.g., $Ar^1$ is 2-ethyl-3-methoxy phenyl and $Ar^2$ is 3,5-dimethyl phenyl. Representative diacylhydrazines according to this embodiment are disclosed, for example, in U.S. Pat. No. 7,456,315 and WO 2008/153801.

The term "amidoketone" refers to a compound having the formula:

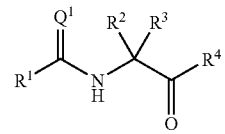

as disclosed in U.S. Pat. No. 7,365,093.

The term "oxadiazoline" refers to a compound having the formula:

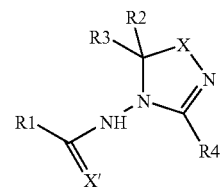

as disclosed in U.S. Pat. No. 7,304,162.

The term "carrier" encompasses any of the standard carriers known in the art. In one embodiment, the carrier is a pharmaceutically acceptable carrier. The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences, Mack Publishing Co., Easton, Pa., 19th ed. 1995. Preferred pharmaceutical carriers depend upon the intended mode of administration of the active agent "Silica gel chromatography" refers to a purification method wherein a chemical substance of interest is applied as a concentrated sample to the top of a vertical column of silica gel or chemically-modified silica gel contained in a glass, plastic, or metal cylinder, and elution from such column with a solvent or mixture of solvents.

"Flash chromatography" refers to silica gel chromatography performed under air, argon, or nitrogen pressure typically in the range of 10 to 50 psi.

"Gradient chromatography" refers to silica gel chromatography in which the chemical substance is eluted from a column with a progressively changing composition of a solvent mixture.

Terms used herein are intended to have their ordinary meanings as used in the art.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, for example, 2 or 3 or 4 or 5 orders of magnitude.

A "nucleic acid" or "nucleic acid molecule" or "polynucleotide" is a polymer comprising covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmid DNA, synthetic DNA, and semi-synthetic DNA. DNA may be linear, circular, or supercoiled. Nucleic acids may refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. This term includes restriction fragments, plasmids, and chromosomes. DNA or RNA sequences may be described according to the normal convention of giving the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "nucleic acid fragment" will be understood to mean a nucleotide sequence of reduced length relative to the reference nucleic acid and comprising, over a common portion, a nucleotide sequence identical to the reference nucleic acid. Such a nucleic acid fragment according to the invention may be, where appropriate, included in a larger polynucleotide. Fragments may range in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide or encode a bioactive RNA molecule. The term "gene" includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer.

A "transgene" is a gene that has been introduced into the genome by a transformation procedure.

"Heterologous" DNA refers to DNA not naturally located in the cell, or in a chromosomal site of the cell. In one embodiment, heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences. In a specific embodiment of the invention, polynucleotides are detected by employing hybridization conditions comprising a hybridization step at $T_m$ of 55° C., and utilizing conditions as set forth above. In one example, the $T_m$ is 60° C.; in another embodiment, the $T_m$ is 63° C.; in another embodiment, the $T_m$ is 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA: RNA, DNA: RNA, DNA: DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at least 63 degrees Celsius. In one embodiment, the hybridization conditions comprise less than 200 mM salt and at least 37 degrees Celsius for the hybridization step. In another embodiment, the hybridization conditions comprise 2×SSPE and 63 degrees Celsius for both the hybridization and washing steps.

In one embodiment, the length for a hybridizable nucleic acid is at least about 10 nucleotides. An example minimum length for a hybridizable nucleic acid is at least about 15 nucleotides; another length is at least about 20 nucleotides; and yet another length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, for instance on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and/or translated into a polypeptide in a cell in vitro or in vivo when placed under the control of appropriate regulatory sequences. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, siRNA, microRNA, shRNA, or other bioactive RNA, cDNA from mRNA, genomic DNA sequences, and even synthetic DNA sequences. If the coding sequence is for a protein intended for expression in a eukaryotic cell, a polyadenylation signal and transcription termination sequence will usually be located 3' to the coding sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (← →) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that cuts a specific nucleotide sequence within double stranded DNA.

"Homologous recombination" refers to the insertion of a foreign DNA sequence into another DNA molecule, e.g., insertion of a vector in a chromosome. For example, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, such as DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. Synthetic cationic lipids designed to limit the difficulties and dangers encountered with liposome-mediated transfection can be used to prepare liposomes for in vivo transfection of a gene encoding a marker (Felgner et al., 1987, PNAS 84:7413; Mackey, et al., 1988. Proc. Natl. Acad. Sci. U.S.A. 85:8027-8031; and Ulmer et al., 1993, Science 259:1745-1748). Useful lipid compounds and compositions for transfer of nucleic acids are described in WO95/18863, WO96/17823 and U.S. Pat. No. 5,459,127. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of RNA or DNA by a cell. A cell has been "transfected" by RNA or DNA when such RNA or DNA has been introduced inside the cell. A cell has been "transformed" by RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, calorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), red fluorescent protein (RFP), Cyan fluorescent protein (CFP), yellow fluorescent protein (YFP), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. Usually, but not always, a coding sequence is located 3' to a promoter sequence. Promoters may be derived from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have similar promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of" or "operably linked to" transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer promoter responsiveness through interaction with a DNA-binding domain. Response elements may be palindromic (perfect or imperfect) or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain binds to the DNA sequence of a response element to initiate or suppress transcription of downstream gene(s) under the regulation of this response element. Examples of DNA sequences for response elements of the natural ecdysteroid receptor include: RRGG/TTCANTGAC/ACYY (SEQ ID NO: 28) (see Cherbas L., et. al., (1991), Genes Dev. 5, 120-131); AGGTCAN$_{(n)}$AGGTCA, where N$_{(n)}$ can be one or more spacer nucleotides (SEQ ID NO: 29) (see D'Avino P P., et. al., (1995), *Mol. Cell. Endocrinol*, 113, 1-9); and GGGTTGAATGAATTT (SEQ ID NO: 30) (see Antoniewski C., et. al., (1994). Mol. Cell. Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to a nuclear receptor-based system, including but not limited to an EcR based system, which in the presence of one or more ligands, modulates the expression of at least one gene of interest, wherein the gene of interest is operably linked to a predetermined response element and promoter. A gene switch can contain polypeptides that form a homodimer or polypeptides that form a heterodimer.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell, are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoters (useful for expression in *Pichia*); β-lactamase, lac, ara, tet, trp, lPL, lPR, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassaya vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the hosts. Optionally, a termination site may be unnecessary. In one embodiment of the invention, the termination control region may comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" or "bioactive RNA" refers to antisense RNA, ribozyme RNA, or other RNA that is not translated yet has an effect on cellular processes.

A "polypeptide" is a polymeric compound comprised of covalently linked amino acid residues.

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The terms "protein," "polypeptide" and "peptide" are used interchangeably herein.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide.

When the substitution mutant polypeptide comprises a substitution of two or more wild-type or naturally occurring amino acids, this substitution may comprise either an equivalent number of wild-type or naturally occurring amino acids deleted for the substitution, i.e., two wild-type or naturally occurring amino acids replaced with two non-wild-type or non-naturally occurring amino acids, or a non-equivalent number of wild-type amino acids deleted for the substitution, i.e., two wild-type amino acids replaced with one non-wild-type amino acid (a substitution+deletion mutation), or two wild-type amino acids replaced with three non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson, C., et al., 1978, J. Biol. Chem. 253: 6551; Zoller and Smith, 1984, DNA 3: 479-488; Oliphant et al., 1986, Gene 44: 177; Hutchinson et al., 1986, Proc. Natl. Acad. Sci. U.S.A. 83: 710), use of TAB® linkers (Pharmacia), restriction endonuclease digestion/fragment deletion and substitution, PCR-mediated/oligonucleotide-directed mutagenesis, and the like. PCR-based techniques are useful for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

"Fragment of a polypeptide" according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50: 667).

In a specific embodiment, two DNA sequences are "substantially homologous" or "substantially similar" when at least about 50% (for instance, at least about 75%, 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that does not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Substantially similar nucleic acid fragments of the instant invention include those nucleic acid fragments whose DNA sequences are at least 80% identical to the DNA sequence of the nucleic acid fragments reported herein. Additional substantially similar nucleic acid fragments include at least 90% identical to the DNA sequence of the nucleic acid fragments reported herein. Additional substantially similar nucleic acid fragments include those that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). In one embodiment, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pair-wise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St., Madison, Wis. 53715 USA). Within the context of this application it will be understood that where sequence analysis software is used for analysis, the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be orthogonal when; a) modulation of each of the given systems by its respective ligand, at a chosen concentration, results in a measurable change in the magnitude of expression of the gene of interest of that system, and b) the change is statistically significantly different than the change in expression of all other systems simultaneously operable in the cell, tissue, or organism, regardless of the simultaneity or sequentially of the actual modulation. For example, modulation of each individually operable gene regulation system effects a change in gene expression at least 2-fold, 5-fold, 10-fold, 100-fold, or 500-fold greater than all other operable systems in the cell, tissue, or organism. Fully orthogonal gene switch systems are capable of independent modulation of each switch component by a respective ligand. Measurable change in the magnitude of expression of a gene of interest of one switch in the system does not affect measurable change in expression of genes of interest in other systems operable in the cell, tissue, or organism. The present invention is useful to search for orthogonal ligands and orthogonal receptor-based gene expression systems.

The term "modulate" means the ability of a given ligand/receptor complex to induce or suppress the expression of a gene or genes of interest.

The term "exogenous gene" means a gene foreign to the subject, that is, a gene which is introduced into the subject through a transformation process, an unmutated version of an endogenous mutated gene or a mutated version of an endogenous unmutated gene. Exogenous genes can be either natural or synthetic genes and therapeutic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject. The term "therapeutic gene" means a gene which imparts a beneficial function to the host cell in which such gene is expressed. A therapeutic gene may be a gene encoding a toxin or other product that contributes to the killing of a cell. Such genes of interest are useful in cancer therapies, for example.

The term "receptor complex" generally refers to a protein complex containing nuclear receptor components, including ecdysteroid receptor (EcR) and/or ultraspiracle (USP) proteins (see Yao, et. al. (1993) Nature 366, 476-479; Yao, et. al., (1992) Cell 71, 63-72). A functional receptor complex may also include additional protein(s) such as immunophilins. Members of the steroid receptor family of proteins, known as transcriptional factors (such as DHR38, betaFTZ-1 or other insect homologs), may also be ligand dependent or independent partners for EcR and/or USP. The receptor complex can also be a heterodimer of ecdysteroid receptor protein and the vertebrate homolog of ultraspiracle protein, retinoic acid-X-receptor ("RXR") protein. Receptor complexes also include EcR-EcR homodimers or USP-USP homodimers or RXR-RXR homodimers.

A receptor complex can be activated by an active steroid or non-steroidal ligand bound to one of the proteins of the complex, inclusive of EcR, but not excluding other proteins of the complex.

A nuclear receptor complex includes proteins which are members of the steroid receptor superfamily wherein members are characterized by the presence of an amino-terminal transactivation domain, a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for response elements. These domains may be either native, modified, or chimeras of different domains of heterologous receptor proteins.

The DNA sequences making up a gene of interest, the response element, and a receptor complex may be incorporated into archaebacteria, prokaryotic cells such as *Escherichia coli, Bacillus subtilis*, or other enterobacteria, or eukaryotic cells such as plant or animal cells. The cells may be in the form of single cells or multicellular organisms. The nucleotide sequences for the gene of interest, the response element, and the receptor complex can also be incorporated as RNA molecules, for example, in the form of functional viral RNAs such as tobacco mosaic virus. Vertebrate cells are advantageous because they naturally lack the molecules which confer responses to the ligands of this invention. As a result, they are insensitive to the ligands of this invention. Therefore, cells can grow and express the desired product, substantially unaffected by the presence of the ligand itself.

The term "subject" means an intact plant or animal or a cell from a plant or animal. It is also anticipated that the ligands will work equally well when the subject is a fungus or yeast. When the subject is an intact animal, the animal includes a vertebrate or a mammal.

The ligands of the present invention, when used with the receptor complex which in turn is bound to the response element linked to a gene of interest, provide for external temporal regulation of expression of a gene of interest. The order in which the various components bind to each other, that is, ligand to receptor complex and receptor complex to response element, is not critical. Typically, modulation of expression of the gene of interest is in response to the binding of the receptor complex to a specific control, or regulatory, DNA element. The ecdysteroid receptor protein, like other members of the steroid receptor family, possesses at least three domains, a transactivation domain, a DNA binding domain, and a ligand binding domain. This receptor, like a subset of the steroid receptor family, also possesses less well-defined regions responsible for heterodimerization properties. Ligand may bind homodimer complexes (e.g. EcR-EcR or USP-USP). One or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et. al. (1988) Nature, 335, 563-564) or LexA protein from *E. coli* (see Brent and Ptashne (1985), Cell, 43, 729-736). Another advantage of chimeric systems is that they allow choice of a promoter used to drive the gene of interest according to a desired end result. Such double control can be particularly important in areas of gene therapy, especially when cytotoxic proteins are produced, because both the timing of expression as well as the cells wherein expression occurs can be controlled. The sequence is the site at which transcription can be specifically initiated under proper conditions. When endogenous or exogenous genes of interest, operatively linked to a suitable promoter, are introduced into the cells of the subject, expression of the genes is controlled by the presence of the ligands of this invention. Promoters may be constitutively or inducibly regulated or may be tissue-specific (that is, expressed only in a particular type of cell) or specific to certain developmental stages of the organism.

Another aspect of this invention is a method to modulate the expression of one or more genes of interest in a subject, comprising administering to the subject an effective amount of a ligand comprising a compound of the present invention and wherein the cells of the subject contain:

a) a receptor complex comprising:
a DNA binding domain;
a ligand binding domain; and
a transactivation domain; and
b) a DNA construct comprising:
a gene of interest; and
a response element;

wherein the gene of interest is under the control of the response element; and binding of the DNA binding domain to the response element in the presence of the ligand results in activation or suppression of the gene of interest.

A related aspect of this invention is a method for regulating endogenous or heterologous gene expression in a transgenic subject comprising contacting a ligand of the present invention with an ecdysteroid receptor within the cells of the subject wherein the cells contain a DNA binding sequence for the ecdysteroid receptor and wherein formation of an ecdysteroid receptor-ligand-DNA binding sequence complex induces expression of the gene.

As well as the advantage of temporally controlling polypeptide production by the cell, this aspect of the invention provides a further advantage, in those cases when accumulation of such a polypeptide can damage the cell, in that expression of the polypeptide may be limited to short periods. Such control is particularly important when the exogenous gene is a therapeutic gene. Therapeutic genes may be called upon to produce polypeptides which control needed functions, such as the production of insulin in diabetic patients. They may also be used to produce damaging or even lethal proteins, such as those lethal to cancer cells.

Numerous genomic and cDNA nucleic acid sequences coding for a variety of polypeptides are well known in the art. Exogenous genetic material or other genes of interest useful with the ligands of this invention include genes that encode biologically active proteins of interest, such as, for example, secretory proteins; enzymes, including enzymes that can metabolize a substrate from a toxic substance to a non-toxic substance, or from an inactive substance to an active substance; regulatory proteins; cell surface receptors; among others. Useful genes also include genes that encode blood clotting factors, hormones such as peptide hormones, insulin, parathyroid hormone, luteinizing hormone releasing factor, alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor, colony stimulating factor-1, tumor necrosis factor, and erythropoietin; genes encoding inhibitor substances such as $alpha_1$-antitrypsin, genes encoding substances that function as drugs such as diphtheria and cholera toxins; among others. Useful genes also include those useful for cancer therapies and to treat genetic disorders. Those skilled in the art have access to nucleic acid sequence information for virtually all known genes and can either obtain the nucleic acid molecule directly from a public depository, the institution that published the sequence, or employ routine methods to prepare the molecule.

For gene therapy use, the ligands described herein may be taken up in pharmaceutically acceptable carriers, such as, for example, solutions, suspensions, tablets, capsules, ointments, elixirs, and injectable compositions. Pharmaceutical preparations may contain from 0.01% to 99% by weight of the ligand. Preparations may be either in single or multiple dose forms. The amount of ligand in any particular pharmaceutical preparation will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that a preferred route of administration will depend upon the condition being treated and may vary with factors such as the condition of the recipient.

The ligands described herein may also be administered in conjunction with other pharmaceutically active compounds. It will be understood by those skilled in the art that pharmaceutically active compounds to be used in combination with the ligands described herein will be selected in order to avoid adverse effects on the recipient or undesirable interactions between the compounds. Examples of other pharmaceutically active compounds which may be used in combination with the ligands include, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflamatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications, nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications, psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases the ligands may be useful as an adjunct to drug therapy, for example, to "turn off" a gene that produces an enzyme that metabolizes a particular drug.

For agricultural applications, in addition to the applications described above, the ligands of this invention may also be used to control the expression of pesticidal proteins such as *Bacillus thuringiensis* (Bt) toxin. Such expression may be tissue or plant specific. In addition, particularly when control of plant pests is also needed, one or more pesticides may be combined with the ligands described herein, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with the ligands described herein include fungicides, herbicides, insecticides, miticides, and microbicides.

The ligands described herein can be applied to plant foliage as aqueous sprays by methods commonly employed, such as conventional high-liter hydraulic sprays, low-liter sprays, air-blast, and aerial sprays.

Host Cells and Non-Human Organisms of the Invention

Ligands for modulating gene expression system of the invention may be used to modulate gene expression in a host cell. Expression in transgenic host cells may be useful for the expression of various genes of interest. The present invention provides ligands for modulation of gene expression in prokaryotic and eukaryotic host cells. Expression in host cells is useful for the expression of various polypeptides of interest including but not limited to antigens produced in plants as vaccines, enzymes, including enzymes like alpha-amylase, phytase, glucanes, and xylanse, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; cell based assays; functional genomics assays, biotherapeutic protein production, proteomics assays, among others.

The host cell may be a bacterial cell, a fungal cell, a nematode cell, an insect cell, a fish cell, a plant cell, an avian cell, an animal cell, a mammalian cell or a human cell. In still another embodiment, the invention relates to ligands for modulating gene expression in a host cell, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated host cell is an invertebrate host cell or a vertebrate host cell. Such host cells may be selected from a bacterial cell, a fungal cell, a yeast cell, a nematode cell, an insect cell, a fish cell, a plant cell, an avian cell, an animal cell, and a mammalian cell. More specifically, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; animal; and mammalian host cells.

In a specific embodiment, the host cell is a *Caenorhabditis elegans* nematode cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art. Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification of proteins. Appropriate cell lines or host systems can be chosen to ensure the desired modification and processing of the foreign protein expressed. For example, expression in a bacterial system can be used to produce a non-glycosylated core protein product. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent. The present invention also relates to a non-human organism comprising an isolated host cell according to the invention.

In a specific embodiment, the non-human organism is a prokaryotic organism or a eukaryotic organism. In another specific embodiment, the non-human organism is an invertebrate organism or a vertebrate organism. In a specific embodiment, the non-human organism is a non-human mammal.

For example, the non-human organism is selected from the group consisting of a bacterium, a fungus, yeast, a nematode, an insect, a fish, a plant, a bird, an animal, and a mammal. More specifically, the non-human organism is yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee. In another specific embodiment, the non-human organism is a *Mus musculus* mouse.

Gene Expression Modulation System of the Invention

The present invention relates to a group of ligands that are useful in a nuclear receptor-based inducible gene expression system. In particular, the present invention relates to ligands having the ability to transactivate a gene expression modulation system comprising at least one gene expression cassette that is capable of being expressed in a host cell comprising a polynucleotide that encodes a polypeptide comprising a nuclear receptor ligand binding domain, such as a Group H nuclear receptor. The Group H nuclear receptor ligand binding is from a steroid receptor, an ecdysteroid receptor, a mutant ecdysone receptor, a ubiquitous receptor, an orphan receptor 1, a NER-1, a steroid hormone nuclear receptor 1, a retinoid X receptor interacting protein-15, a liver X receptor β a steroid hormone receptor like protein, a liver X receptor, a liver X receptor α, a farnesoid X receptor, a receptor interacting protein 14, and a farnesol receptor. In one embodiment, the Group H nuclear receptor ligand binding domain is from an ecdysteroid receptor.

In a specific embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene of interest whose expression is to be modulated.

In another specific embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene of interest whose expression is to be modulated.

In another specific embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is a Group H nuclear receptor ligand binding domain comprising a substitution mutation. In one embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene of interest whose expression is to be modulated.

When only one nuclear receptor ligand binding domain is a Group H ligand binding domain comprising a substitution mutation, the other nuclear receptor ligand binding domain may be from any other nuclear receptor that forms a dimer with the Group H ligand binding domain comprising the substitution mutation. For example, when the Group H nuclear receptor ligand binding domain comprising a substitution mutation is an ecdysteroid receptor ligand binding domain comprising a substitution mutation, the other nuclear receptor ligand binding domain ("partner") may be from a steroid receptor, an ecdysteroid receptor, a vertebrate retinoid X receptor (RXR), an invertebrate RXR, an ultraspiracle protein, or a chimeric nuclear receptor comprising at least two different nuclear receptor ligand binding domain polypeptide fragments selected from vertebrate RXR, an invertebrate RXR, and a USP (see PCT/US01/09050, PCT/US02/05235, and PCT/US02/05706). The "partner" nuclear receptor ligand binding domain may further comprise a truncation mutation, a deletion mutation, a substitution mutation, or another modification, or a combination thereof.

In one embodiment, the vertebrate RXR ligand binding domain is from a human, mouse, rat, chicken, pig, frog, zebrafish *Danio rerio*, tunicate, or jellyfish *Tripedalia cysophora* RXR.

For example, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

The chimeric RXR ligand binding domain may comprise at least two polypeptide fragments selected from a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

In a specific embodiment, the gene of interest is an endogenous gene with respect to the host cell. In another specific embodiment, the gene of interest is an exogenous gene with respect to the host cell.

In a specific example, binding of the ligand to the ligand binding domain of a Group H nuclear receptor and its nuclear receptor ligand binding domain partner enables expression or suppression of the gene. In a specific embodiment, one or more of the receptor domains is varied producing a hybrid (chimeric) gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast or LexA protein from *Escherichia coli*, or synthetic response elements specific for targeted interactions with proteins designed, modified, and selected for such specific interactions (see, for example, Kim, et al. (1997), *Proc. Natl. Acad. Sci., USA*, 94: 3616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cell) or specific to certain developmental stages of the organism.

The ecdysteroid receptor is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). Other members of this nuclear receptor subfamily 1, group H include: ubiquitous receptor (UR), orphan receptor 1 (OR-1), steroid hormone nuclear receptor 1 (NER-1), retinoid X receptor interacting protein-15 (RIP-15), liver X receptor β (LXRβ), steroid hormone receptor like protein (RLD-1), liver X receptor (LXR), liver X receptor α (LXRα), farnesoid X receptor (FXR), receptor interacting protein 14 (RIP-14), and farnesol receptor (HRR-1).

In particular, described herein are novel ligands useful in a gene expression modulation system comprising a Group H nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides.

An ecdysteroid receptor-based gene expression modulation system of the present invention may be either heterodimeric or homodimeric. A functional EcR complex generally refers to a heterodimeric protein complex of two members of the nuclear receptor family, an ecdysteroid receptor protein and an ultraspiracle protein or the vertebrate homolog of USP, retinoid X receptor protein. However, the complex may also be a homodimer. Additional members of the steroid receptor family of proteins, known as transcriptional factors (such as DHR38 or betaFTZ-1), may also be ligand dependent or independent partners for EcR, USP, and/or RXR.

The ecdysteroid receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a response element. Members of the nuclear receptor superfamily are also characterized by the presence of four or five domains: A/B, C, D, E, and in some members F (see U.S. Pat. No. 4,981,784 and Evans, Science 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysteroid response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Method of Modulating Gene Expression of the Invention

The present invention provides a method of modulating the expression of a gene of interest in a host cell comprising the steps of: a) introducing into the host cell a gene expression modulation system according to the invention; and b) introducing into the host cell a ligand; wherein the gene of interest is a component of a gene expression cassette comprising: i) a response element comprising a domain recognized by the DNA binding domain of the gene expression system; ii) a promoter that is activated by the transactivation domain of the gene expression system; and iii) a gene of interest whose expression is to be modulated, whereby upon introduction of the ligand into the host cell, expression of the gene of interest is modulated.

The invention also provides a method of modulating the expression of a gene in a host cell comprising the steps of: a) introducing into the host cell a gene expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene of interest whose expression is to be modulated; and c) introducing into the host cell a ligand; whereby upon introduction of the ligand into the host cell, expression of the gene of interest is modulated.

Genes of interest for expression in a host cell using methods disclosed herein may be endogenous genes or exogenous genes. Nucleic acid or amino acid sequence information for a desired gene or protein can be located in one of many public databases, for example, GENBANK, EMBL, Swiss-Prot, and PIR, or in many journals. Such information can then be used to construct the desired constructs for the insertion of the gene of interest within the gene expression cassettes used in the methods described herein.

Examples of genes of interest include, but are not limited to: antigens produced in plants as vaccines, enzymes like alpha-amylase, phytase, glucanes, and xylanse, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, proteins, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erythropoietin, toxins, clotting factors, other blood factors or components, viral vectors for gene therapy, viruses for vaccines, targets for drug discovery, functional genomics, and proteomics analyses and applications, among others.

Measuring Gene Expression/Transcription

One useful measurement of the methods of the invention is that of the transcriptional state of the cell including the identities and abundances of RNA, such as mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. DNA microarrays are arrays of DNA samples, typically PCR products that are robotically printed onto a microscope slide. Each gene is analyzed by a full or partial-length target DNA sequence.

Another useful measurement of the methods of the invention is that of determining the translation state of the cell by measuring the abundances of the constituent protein species present in the cell using processes known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using the present invention.

Other methods to detect the products of gene expression are well known in the art and include Southern blots (DNA detection), dot or slot blots (DNA, RNA), northern blots (RNA), RT-PCR(RNA), western blots (polypeptide detection), and ELISA (polypeptide) analyses. Labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with a pair of oligonucleotide primers.

GENERAL METHODS

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and Methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.).

The meaning of abbreviations is as follows: "h" means hour(s), "min" means minute(s), "sec" means second(s), "d" means day(s), "µL" means microliter(s), "mL" means milliliter(s), "L" means liter(s), "µM" means micromolar, "mM" means millimolar, "M" means molar, "mol" means moles, "mmol" means millimoles, "µg" means microgram(s), "mg" means milligram(s), "A" means adenine or adenosine, "T" means thymine or thymidine, "G" means guanine or guanosine, "C" means cytidine or cytosine, "xg" means times gravity, "nt" means nucleotide(s), "aa" means amino acid(s), "bp" means base pair(s), "kb" means kilobase(s), "k" means kilo, "µ" means micro, "° C." means degrees Celsius, "C" in the context of a chemical equation means Celsius, "THF" means tetrahydrofuran, "DME" means dimethoxyethane, "DMF" means dimethylformamide, "NMR" means nuclear magnetic resonance, "psi" refers to pounds per square inch, "TLC" means thin layer chromatography, "approx." means approximately, "calc." means calculated, "cm" means centimeters, "$EC_{50}$" means effective concentration giving 50% response, "eq" means equivalents, "g" means grams, "i.d." means internal diameter, "[M]" means molecular mass, "µmol" means micromoles, "N" means normal concentration, "nm" means nanometers, "NMR" means nuclear magnetic resonance spectroscopy, "nOe" means nuclear Overhauser effect, "NP" means normal phase, "ppm" means parts per million, "Rf" means retention factor, "RP" means reverse-phase, "r.t." means room temperature, "R.t." means retention time, "UV" means ultra-violet, "v/v" or "v/v/v" means volume/volume ratio, "w/v" means weight/volume ratio, and "λ" means wavelength.

PREPARATION OF COMPOUNDS

Chemicals and Reagents

Silver oxide ($Ag_2O$), iodomethane ($CH_3I$), iodoethane ($CH_3CH_2I$), 1-iodopropane ($CH_3CH_2CH_2I$), 1-iodobutane ($CH_3CH_2CH_2CH_2I$), allyl bromide ($CH_2\!\!=\!\!CHCH_2Br$), benzyl bromide ($C_6H_5CH_2Br$), 1-bromo-2-butanone ($CH_3CH_2COCH_2Br$), anhydrous N,N-dimethylformamide (DMF), 2,2-dimethoxypropane (DMP), phenylboronic acid (PBA), monohydrated para-toluenesulphonic acid (p-TsOH), tetrahydrofuran (THF), 1,4-dioxane, methyl triflate ($CF_3SO_2OCH_3$), 2,6-di-tert-butyl-4-methylpyridine ($C_{14}H_{23}N$) and p-anisaldehyde were purchased from Aldrich. Celite® was purchased from BDH. Minisart® filters were purchased from Sartorius. Hydrogen peroxide ($H_2O_2$) 100 volumes, sulphuric acid ($H_2SO_4$), hydrochloric acid (HCl), acetic acid (AcOH), sodium hydroxide (NaOH), acetone, ethyl acetate (AcOEt) and HPLC-grade methanol (MeOH), ethanol (EtOH), chloroform ($CHCl_3$) and dichloromethane ($CH_2Cl_2$) were purchased from Fisher Scientific. Methanol-$d_4$ was purchased from Goss Scientific Instruments Ltd. 20-Hydroxyecdysone (20E) was supplied by Dr. V. Volodin, Institute of Biology, Russian Academy of Sciences, Syktyvkar, Russia. Ponasterone A (PoA) was supplied by Dr. René Lafont, Université Pierre et Marie Curie. Dry acetone was obtained by distillation following by storage of the solvent on 4 Å molecular sieves.

General Reaction Conditions

Anhydrous reaction conditions were obtained by flame-drying Schlenk reaction tubes under vacuum and introducing a nitrogen or an argon atmosphere before introducing the reagents, by using anhydrous solvents and a cannula to transfer liquids and by freeze-drying the steroids employed as starting materials. Reactions involving $Ag_2O$ were protected from light by wrapping the Schlenk tube in aluminum foil. Reactions were monitored by either thin-layer chromatography (TLC) and/or high-performance liquid chromatography (HPLC). TLC was performed using Merck HPTLC aluminum sheets 20×20 cm silica gel 60 $F_{254}$. Plates were visualized under UV light, following by dipping into a 5% p-anisaldehyde/5% $H_2SO_4$ in EtOH solution and heating. Mobility of compounds is expressed as $R_f$ values ($R_f$=distance moved by compound/distance moved by solvent front). Reaction-monitoring by HPLC required equal volumes of the reaction mixture to be taken out of the reaction pot at regular intervals of time, the samples quenched with MeOH, centrifuged and the supernatants filtered through a Minisart® 0.20 µm filter. The filtrates were concentrated under reduced pressure, made up with 30% MeOH in $H_2O$ (v/v) and injected on to an analytical $C_{18}$-HPLC with DAD (see column details below) running a linear gradient from 30% to 100% MeOH in $H_2O$ in 25 min, following by 10 min at isocratic 100% MeOH, at a flow-rate of 1 mL/min and monitoring at both λ=242 and λ=300 nm, to identify the different products on the basis of the characteristic retention times (R.t.) shown, as well as by inspection of the full UV spectrum of specific peaks.

Isolation, Purification and Quantification

Waters Sep-Pak® Vac 35 cc $C_{18}$-10 g cartridges were used for the pre-purification of crude reaction mixtures. The sample was applied as solution 5% MeOH in $H_2O$, then washed using a step-gradient of increasing solvent strength (typically, 30%, 80% and 100% MeOH in $H_2O$) to selectively elute the compounds of interest. Isolation and purification were conducted by either RP- or NP-HPLC, where the effluent was monitored at 242 nm for the presence of the steroid chromophore, either with a Gilson 170 Diode Array Detector (DAD) or a Gilson single wavelength Holochrome/115 UV detector. Analytical HPLC was performed with either a $C_{18}$ column (Phenomenex Sphereclone ODS2, 5 μm, 150×4.60 mm or Phenomenex Prodigy ODS2, 5 μm, 250×4.60 mm,) or a $C_6$ column (Phenomenex Sphereclone, 5 μm, 150×4.60 mm) or a diol column (Jones Apex 11 Diol, 5 μm, 150×4.60 mm or GRACE Apex II Diol, 5 μm, 150×4.60 mm) or a silica column (Zorbax Sil, 5 μm, 250×4.60 mm), all at a flow-rates of 1 mL/min. Semi-preparative HPLC was performed with either a $C_{18}$ column (Phenomenex Sphereclone ODS2, 5 μm, 250×10 mm) or a silica column (Zorbax Sil, 5 μm, 250×9.40 mm), or a diol column (GRACE Apex II, 5 μm, 150×8.00 mm), all at a flow-rate of 2 mL/min. Preparative HPLC was performed with a $C_{18}$ column (Phenomenex Sphereclone ODS2, 5 μm, 250×21.20 mm) at a flow-rate of 5 mL/min. Quantification was carried out by ultra-violet spectrometry on a Shimadzu UV-2401PC for compounds containing either the 14α-hydroxy-7-en-6-one moiety ϵ (extinction coefficient) at 242 nm: 12400 Lmol$^{-1}$ cm$^{-1}$) and the dacryhainansterone-like conjugated system (ϵ at 299 nm: 14190 Lmol$^{-1}$ cm$^{-1}$). Concentrations were calculated according to the Lambert-Beer equation.

Spectroscopic Techniques and Bioassays

Nuclear magnetic resonance (NMR) spectra were recorded either on a Bruker Avance/DRX 400 NMR spectrometer, operating at a proton frequency of 400 MHz and a carbon frequency of 100 MHz, or on a Bruker ACF 300 NMR spectrometer, operating at a proton frequency of 300 MHz and a carbon frequency of 75 MHz. Samples were dissolved in deuterated methanol with tetramethylsilane as an internal standard. Chemical shifts are expressed in parts per million (ppm). High-resolution mass spectroscopy was performed in either the chemical ionisation mode (CIMS) or the positive-ion Fast Atom Bombardment Mass Spectroscopy (FABMS) mode. CIMS was recorderd either on a Micromass GCT spectrometer equipped with a direct inlet probe, or on a Jeol MS700 spectrometer equipped with a directinlet probe, using in both cases methane as the reagent gas and methanol as the solvent. FABMS was recorded on a Jeol MS700 spectrometer, using xenon as reagent gas and "Magic Bullet" (a 4:1 mixture of 1,4-dithio-L-threitol and 1,4-dithioerythreitol) as the matrix or VG Quattro mass spectrometer, using a glycerol matrix and methanol as the solvent.

Preparation of 20E 2,3-acetonide

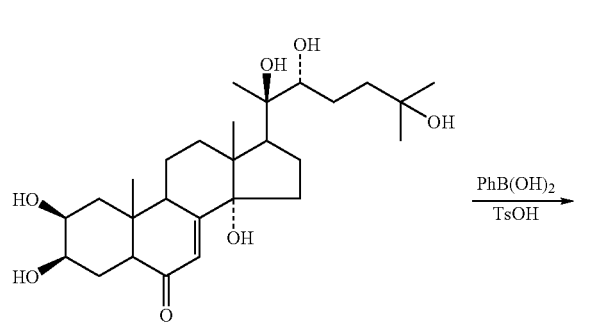

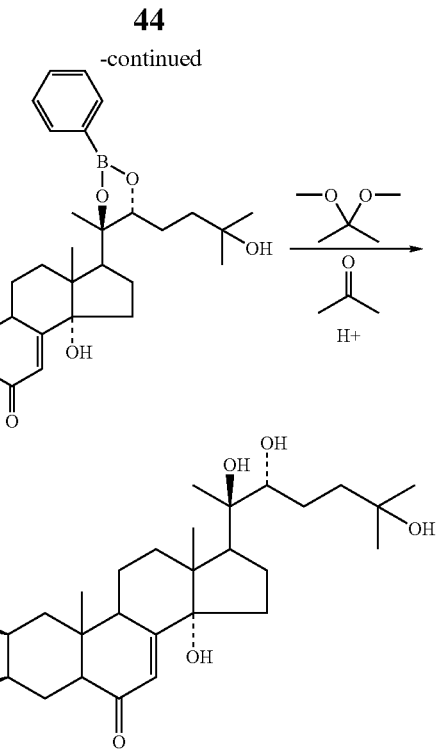

20E (197.7 mg, 411.9 μmol) and PBA (58.6 mg, 480 μmol) were dissolved in anhydrous DMF (4.5 mL) and the mixture stirred at room temperature under anhydrous conditions for 1 h. Fused p-TsOH (39.3 mg, 0.5 eq, prepared from monohydrate p-TsOH by removal of $H_2O$ of crystallization by gently heating in a Bunsen flame under nitrogen atmosphere until reaching a molten state) and DMP (2.3 mL) in dry acetone (4.6 mL) were then added and the mixture was stirred for 3 h. Acetone and DMP were then removed under reduced pressure and the mixture diluted with AcOEt (20 mL), washed with brine (3×10 mL) and the organic solvent removed under reduced pressure. 15 mL of THF/$H_2O_2$ 9:1 v/v ($H_2O_2$ 100 volumes, pre-neutralized with NaOH 0.1 N) was added to the residue and the mixture stirred at room temperature for 2.5 h maintaining a neutral pH (the pH spontaneously lowers, causing re-conversion of 20E 2,3-acetonide to 20E). THF was removed by rotary evaporation and the mixture re-suspended in a 25% MeOH/$H_2O$ solution and cooled to 0° C. The precipitate was collected by filtration of the suspension through cotton wool and the residue recovered by dissolution in MeOH followed by rotary evaporation to yield pure 20E 2,3-acetonide (138.5 mg, yield=65%).

Preparation of 20E 22-methyl ether

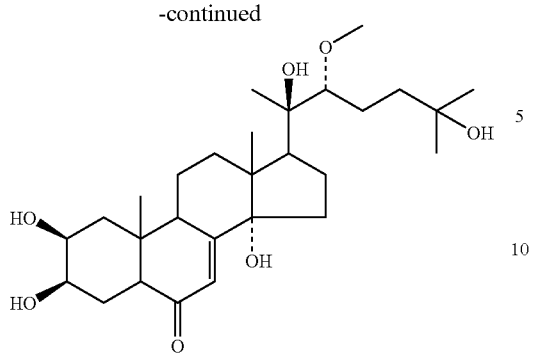

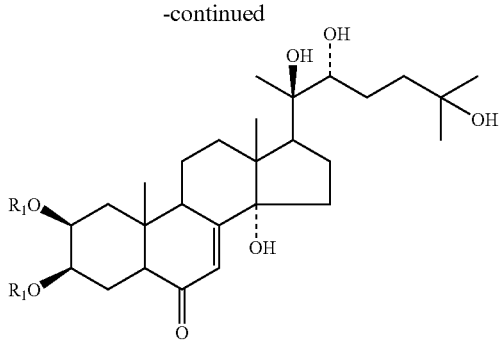

$R_1, R_2 = H, CH_3$

Ag$_2$O (207.0 mg, 10 eq) and CH$_3$I (90 µL, 15 eq) were added to a solution of 20E 2,3-acetonide (48.0 mg, 92.3 µmol) in 1.3 mL anhydrous DMF and the mixture was stirred at room temperature under anhydrous conditions. After 2.5 h of reaction, the mixture was worked up as follows: AcOEt (25 mL) was added and the mixture was filtered through a Celite® pad, the pad washed with AcOEt (150 mL) and the solvent rotary evaporated. The crude reaction mixture was then pre-purified using a C$_{18}$ Sep-Pak® and the product purified by semi-preparative C$_{18}$-HPLC system with isocratic 70% MeOH/H$_2$O, which yielded 24.1 mg (49%) 22-methyl ether 20E 2,3-acetonide (R.t.=23 min). Removal of the 2,3-isopropylidene group was carried out as follows: aqueous HCl (0.1 M, 1.0 mL) was added drop wise to a solution of the product in 1,4-dioxane (1.0 mL) and the mixture was stirred at room temperature. After 2.5 h of reaction, the mixture was diluted to a 5% 1,4-dioxane/H$_2$O solution and pre-purified by C$_{18}$ Sep-Pak®. The desired product was then purified by semi-preparative C$_{18}$-HPLC (58% MeOH/H$_2$O), which yielded 22 mg (48%) 20E 22-methyl ether (R.t.=17 min). Full characterization was obtained by 400 MHz NMR analysis (Table 3a-3e) and CIMS (Calc. [M+H]$^+$=495.3322. Found [M+H]$^+$=495.3348).

Preparation of 20E 2-methyl ether and 20E 3-methyl ether

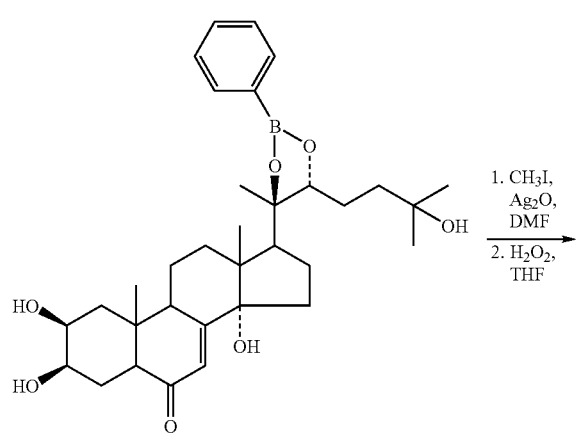

Ag$_2$O (116.0 mg, 10 eq) was added to a solution of freshly prepared 20E 20,22-phenylboronate (30 mg, 53 µmol) in DMF (2 mL). CH$_3$I (258 µL, 44.7 eq) was added in four portions during the course of the reaction and the mixture was stirred at room temperature under anhydrous conditions. After 4 h, further Ag$_2$O (10 eq) was added and the mixture left stirring for a total of 7.5 h. The reaction was worked up and the phenylboronate group was removed as described for the preparation of 20E 2,3-acetonide. The putative products were purified using a semi-preparative C$_{18}$-HPLC system with isocratic 50% MeOH/H$_2$O, where 20E 3-methyl ether eluted after 20 min (6 mg, 25%) and 20E 2-methyl ether after 23 min (13 mg, 50%). Full characterization was obtained by 400 MHz NMR analysis (Table 3a-3e) and CIMS (20E 2-methyl ether: Calc. [M+H]$^+$=495.3322. Found [M+H]$^+$=495.3337. 20E 3-methyl ether: Calc. [M+H]$^+$=495.3322. Found [M+H]$^+$=495.3344).

Preparation of 20E-2,3;20,22-diacetonide

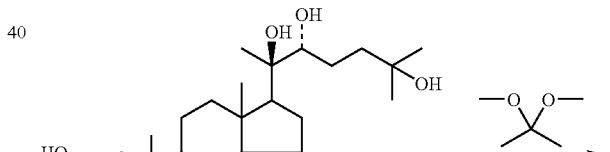

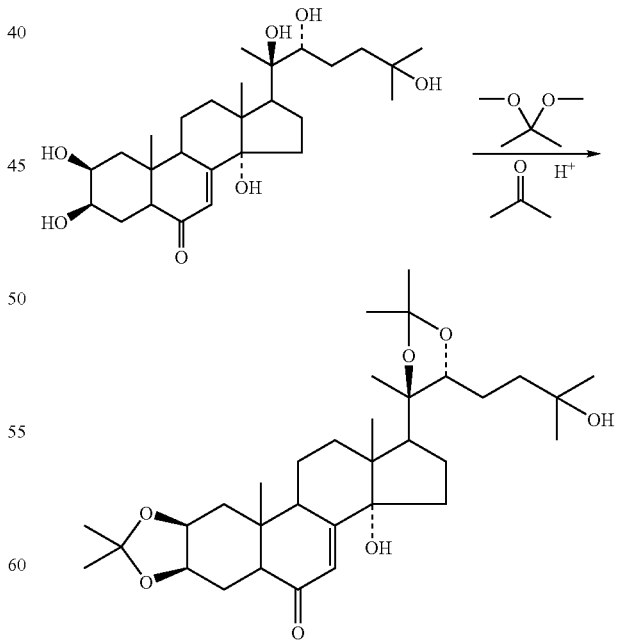

20E (236 mg; 492 µmol) was dissolved in dry acetone (10 mL) under anhydrous conditions. Anhydrous DMF (0.5 mL) was also added to help dissolution. Fused p-TsOH (51 mg, 0.2 eq; prepared as described above) and DMP (0.2 mL) were transferred into the reaction pot and the mixture stirred at room temperature under a nitrogen flow for 6 h. The solvents were then partially removed under reduced pressure, and the remaining solution was added to AcOEt (100 mL) and washed with $H_2O$ (50 mL) and then with a saturated NaCl solution (3×50 mL). The organic phase, analyzed by TLC ($CHCl_3$/MeOH; 15:1, v/v; $R_{f\ 20E\ 2,3,20,22\text{-}diacetonide}$=0.35; $R_{f\ 20E\ 20,22\text{-}monoacetonide}$=0.13) and analytical $C_{18}$-HPLC, resulted composed by both 20E 2,3,20,22-diacetonide (R.t.=23.2) and 20E 20,22-monoacetonide (R.t.=19.5 min). Isolation of the two products was carried out by a silica gel (Merck, Kieselgel 60) open-column (2.5 i.d.×25 cm) chromatography, eluting 79.7 mg (29%) the former compound with $CH_2Cl_2$/MeOH (17:1, v/v), and 142.4 mg (52%) the latter compound with $CH_2Cl_2$/MeOH (13:1, v/v). Characterization was obtained by NMR and CIMS analysis and the data were found in accordance with the literature values (ecdybase.org.)

Preparation of 20E 14-methyl ether

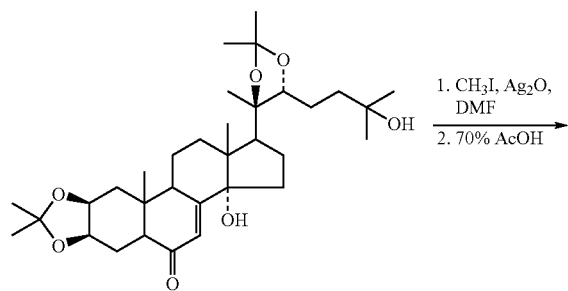

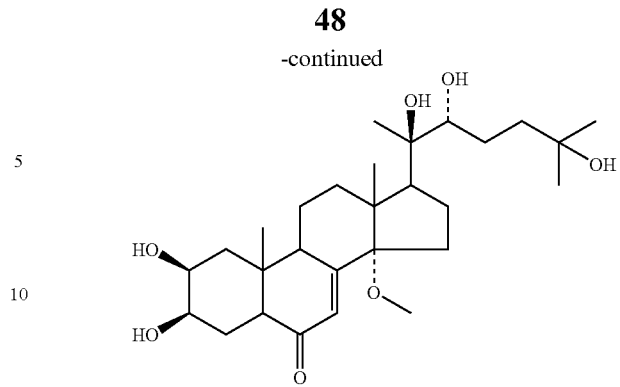

$Ag_2O$ (324.4 mg, 20 eq) and $CH_3I$ (260 μL, 60 eq) were added to a solution of 2,3,20,22-diacetonide (39.3 mg, 70.2 μmol) and the mixture was stirred at 60° C. under anhydrous conditions. After 3 h, the reaction mixture was worked up as described for 20E 22-methyl ether. Removal of the acetonide groups was carried out dissolving the crude reaction mixture in 1,4-dioxane (1 mL), adding 70% aqueous AcOH (10 mL) and refluxing at 80° C. for 8 h, when the heat was turned off and the mixture left stirring overnight. The reaction mixture was then diluted with $H_2O$ (50 mL; previously saturated with 1-butanol) and washed with 1-butanol (4×50 mL; previously saturated with $H_2O$). The combined organic phase was evaporated under reduced pressure and the residue purified by $C_{18}$-HPLC (50% MeOH/$H_2O$), which yielded 4.5 mg (13%) 20E 14-methyl ether (R.t.=21 min). Full characterization was obtained by 400 MHz NMR analysis (Table 3a-3e) and CIMS (Calc. [M+H]$^+$=495.3322. Found [M+H]$^+$=495.3317).

Preparation of 20E 25-methyl ether and 20E 22,25-dimethyl ether

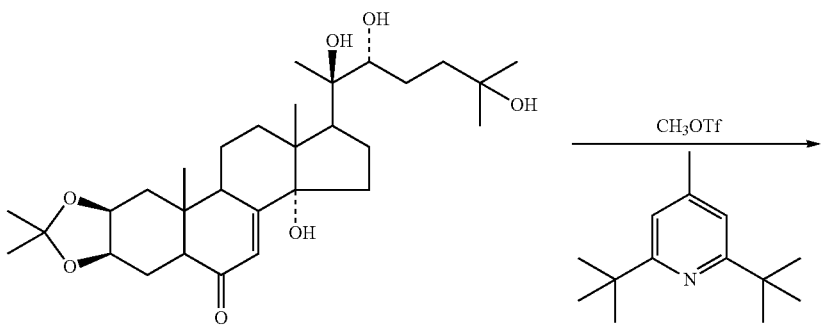

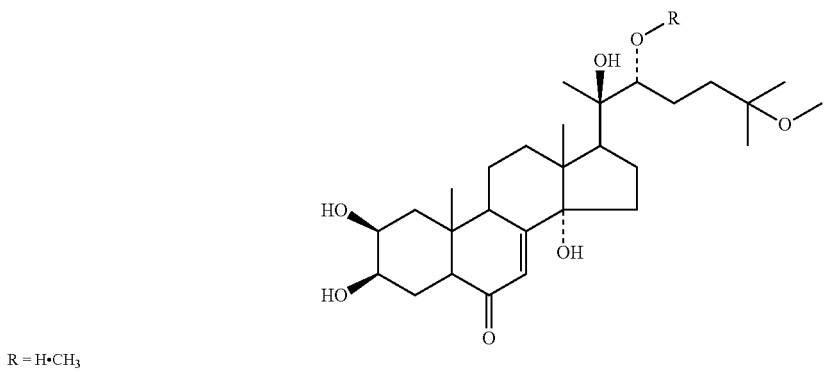

R = H•CH$_3$

Di-tert-butyl-4-methyl-pyridine (88.8 mg, 6 eq) and methyl triflate (47 µL, 6 eq) were added to a solution of 20E 2,3-acetonide (37.5 mg, 72.1 µmol) in dry CH$_2$Cl$_2$ (3 mL) and the mixture was stirred at room temperature under anhydrous conditions. After 55 h, methyl triflate was removed under vacuum and the residue was treated with HCl (0.1 M): 1,4-dioxane 1:1 (v/v) for neutralization and removal of the 2,3-acetonide group. Purification of the desired products was carried out by a preparative C$_{18}$-HPLC system with isocratic 60% MeOH/H$_2$O, which allowed the collection of 11.15 mg (31%) 20E 25-methyl ether (R.t.=20.1 min) and 5.63 mg (15%) 20E 22,25-dimethyl ether (R.t.=42.0 min). Characterization of the two compounds was obtained by 300 MHz NMR analysis (Table 3a-3e) and FAB-MS (20E 25-methyl ether: Calc. [M+H]$^+$=495.6690. Found [M+H]$^+$=495.4. 20E 22,25-dimethyl ether: Calc. [M+H]$^+$=509.6960. Found [M+H]$^+$=509.4).

Preparation of 20E 22-ethyl ether

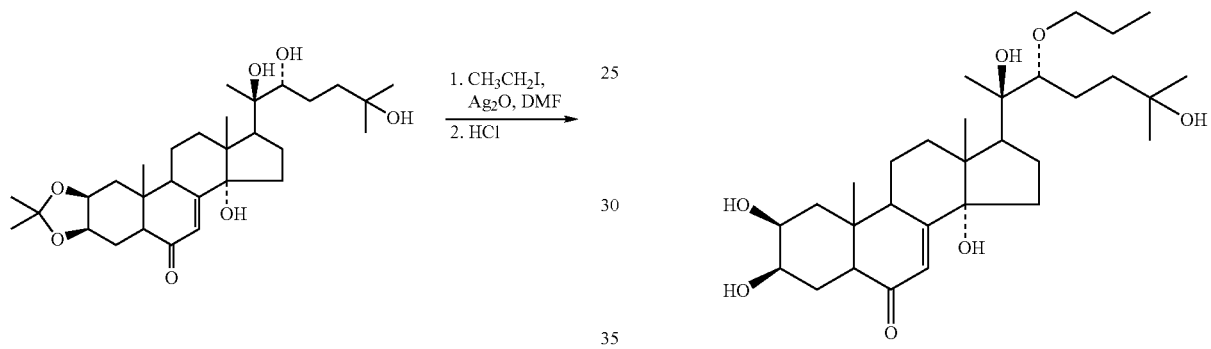

Ag$_2$O (534 mg, 40 eq) and CH$_3$CH$_2$I (92 µL, 20 eq) were added to a solution of 20E 2,3-acetonide (30 mg, 57.7 µmol) in anhydrous DMF (2 mL) and the reaction stirred at room temperature under anhydrous conditions. After 28 h, the reaction was worked up and the 2,3-acetonide group removed as described for 20E 22-methyl ether. Purification of the putative product was carried out by a semi-preparative C$_{18}$-HPLC with isocratic 70% MeOH/H$_2$O, where it eluted at R.t.=12 min, following by a semi-preparative silica column with isocratic CH$_2$Cl$_2$/isopropanol/H$_2$O (125/30/2, v/v/v) where it eluted at R.t.=19.6 min, and yielded 5.5 mg (19%) 20E 22-ethyl ether. Full characterization was obtained by 400 MHz NMR analysis (Table 3a-3e) and CIMS (Calc. [M+H]$^+$= 509.3478. Found [M+H]$^+$=509.3503).

Preparation of 20E 22-n-propyl ether

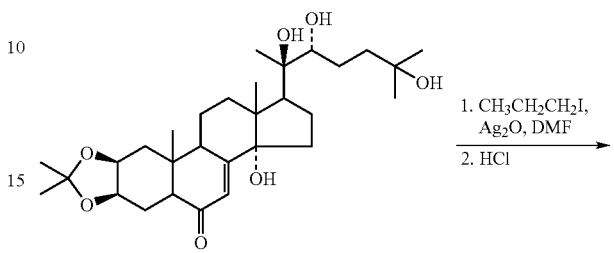

Ag$_2$O (208 mg, 10 eq) and CH$_3$(CH$_2$)$_2$I (187 µL, 20 eq) were added to a solution of 20E 2,3-acetonide (50 mg, 96.1 µmol) in anhydrous DMF (2 mL) and the reaction stirred at room temperature under anhydrous conditions. After 8 h, further CH$_3$CH$_2$CH$_2$I (20 eq) was added. After 24 h, the reaction was worked up and the 2,3-acetonide group removed as described for 20E 22-methyl ether. Purification of the putative product was carried out by a semi-preparative C$_{18}$-HPLC with isocratic 70% MeOH/H$_2$O, where it eluted at R.t.=18 min and yielded 11.6 mg (23%) 20E 22-n-propyl ether. Full characterization was obtained by 400 MHz NMR analysis (Table 3a-3e) and CIMS (Calc. [M+H]$^+$=523.3635. Found [M+H]$^+$=523.3613).

Preparation of 20E 22-n-butyl ether

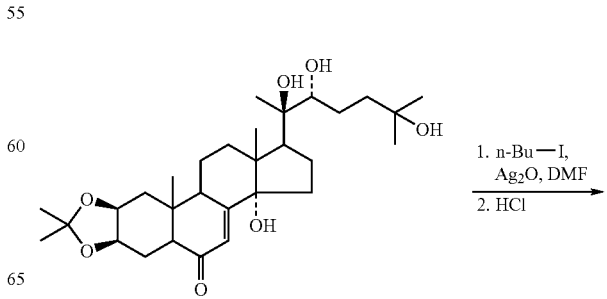

-continued

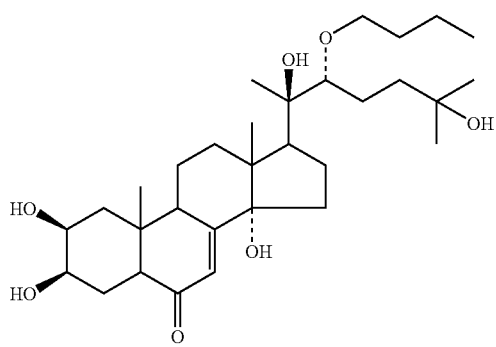

Ag$_2$O (649.7 mg, 40 eq) and CH$_3$(CH$_2$)$_3$I (239 μL, 30 eq) were added to a solution of 20E 2,3-acetonide (36.4 mg, 70.1 μmol) in anhydrous DMF (3 mL) and the reaction stirred at room temperature under anhydrous conditions. After 8 h, further CH$_3$CH$_2$CH$_2$I (20 eq) was added. After 45 h, the reaction was worked up and the 2,3-acetonide group removed as described for 20E 22-methyl ether. Purification of the putative product was carried out by preparative C$_{18}$-HPLC with isocratic 75% MeOH/H$_2$O, where it eluted at R.t.=33 min, and yielded 11.1 mg (30%) 20E 22-n-butyl ether. Full characterization was obtained by 300 MHz NMR analysis (Table 3a-3e) and FAB-MS (Calc. [M+H]$^+$=537.7500. Found [M+H]$^+$=537.7).

Preparation of 20E 22-(28R,S)-2'-ethyloxiranyl ether

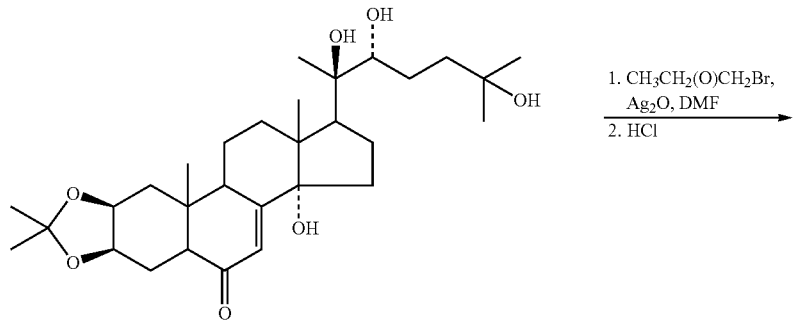

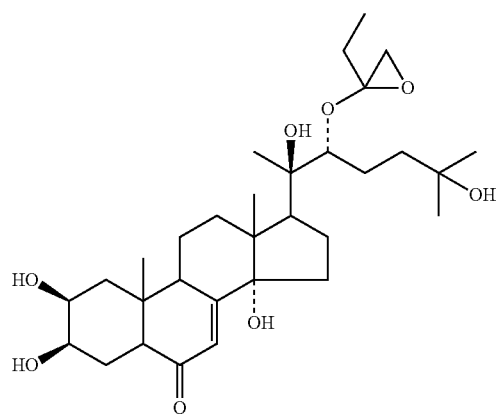

Ag$_2$O (790.0 mg, 40 eq) and CH$_3$CH$_2$COCH$_2$Br (391 µL, 45 eq) were added to a solution of 20E 2,3-acetonide (44.3 mg, 85.2 µmol) in anhydrous DMF (4 mL) and the reaction stirred at room temperature under anhydrous conditions. After 72 h, the reaction was worked up and the 2,3-acetonide group removed as described for 20E 22-methyl ether. Purification of the putative product was carried out by preparative C$_{18}$-HPLC using first an isocratic 75% MeOH/H$_2$O system, where it eluted at R.t.=21 min, and subsequently an isocratic 70% MeOH/H$_2$O system, where it eluted at R.t.=30 min, and yielded 5.0 mg (11%) 20E 22-(28R,S)-2'-ethyloxiranyl ether. Full characterization was obtained by 300 MHz NMR analysis (Table 3a-3e) and FAB-MS (Calc. [M+H]$^+$=571.7330. Found [M+H]$^+$=551.3).

Preparation of 20E 22-allyl ether

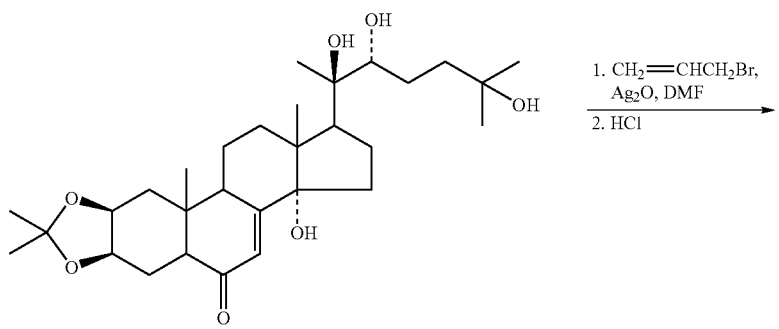

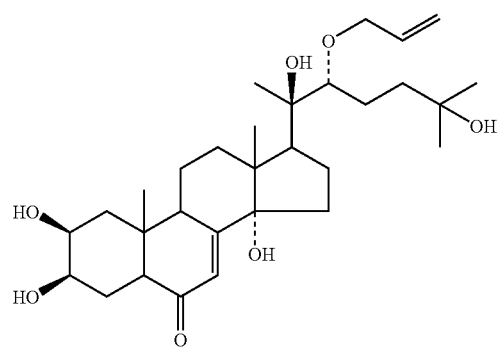

Ag$_2$O (137.7 mg, 10 eq) and CH$_2$=CHCH$_2$Br (75 μL, 15 eq) were added to a solution of 20E 2,3-acetonide (30.9 mg, 59.4 lμmol) in anhydrous DMF (2 mL) and the reaction stirred at room temperature under anhydrous conditions and monitored by TLC(CHCl$_3$/MeOH; 10:1, v/v; R$_{f\,20E\,2,3\text{-}acetonide}$=0.16; R$_{f\,22\text{-}allyl\,20E\,2,3\text{-}acetonide}$=0.33). After 26 h, the reaction was worked up and the 2,3-acetonide group removed as described for 20E 22-methyl ether. Purification of the putative product was carried out by preparative C$_{18}$-HPLC with isocratic 70% MeOH/H$_2$O system, where it eluted at R.t.=26 min, and yielded 11.6 mg (38%) 20E 22-allyl ether. Full characterization was obtained by 300 MHz NMR analysis (Table 3a-3e) and FAB-MS (Calc. [M+H]$^+$=521.7070. Found [M+H]$^+$=521.4).

Preparation of 20E 22-benzyl ether

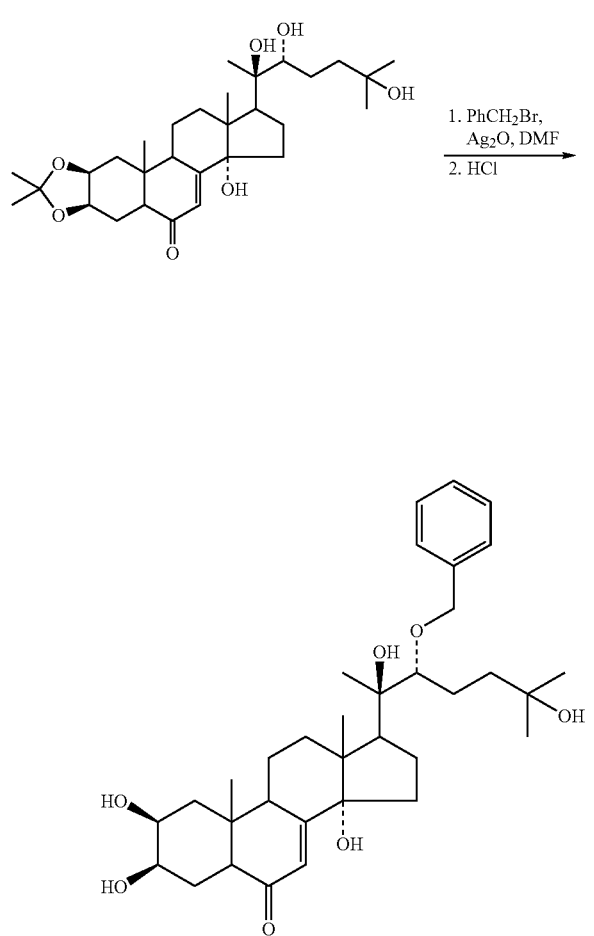

Ag$_2$O (139.5 mg, 10 eq) and C$_6$H$_5$CH$_2$Br (107 μL, 15 eq) were added to a solution of 20E 2,3-acetonide (31.3 mg, 60.2 μmol) in anhydrous DMF (2 mL) and the reaction stirred at room temperature under anhydrous conditions and monitored by TLC(CHCl$_3$/MeOH; 10:1, v/v; R$_f$ 22-benzyl 20E 2,3-acetonide=0.36). After 72 h, the reaction was worked up and the 2,3-acetonide group removed as described for 20E 22-methyl ether. Purification of the putative product was carried out by preparative C$_{18}$-HPLC with isocratic 70% MeOH/H$_2$O system, where it eluted at R.t.=48 min, and yielded 3.0 mg (9%) 20E 22-benzyl ether. Full characterization was obtained by 400 MHz NMR analysis (Table 3a-3e) and FAB-MS (Calc. [M+H]$^+$=571.7670. Found [M+H]$^+$=571.2).

Preparation of 20E 2,22-dimethyl ether and 20E 3,22-dimethyl ether

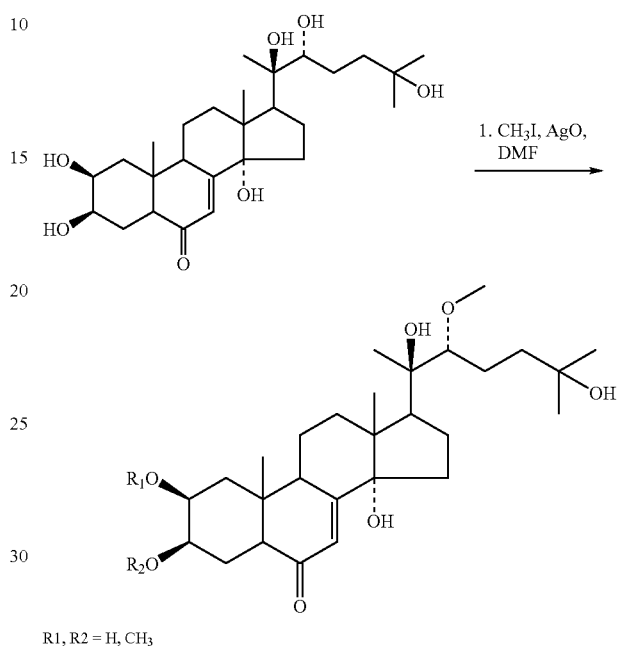

R1, R2 = H, CH$_3$

Ag$_2$O (538 mg, 10 eq) and CH$_3$I (210 μL, 15 eq) were added to a solution of 20E (108 mg, 225 μmol) in anhydrous DMF (3 mL) and the reaction was stirred at room temperature under anhydrous conditions. After 1.5 h, a further 10 eq Ag$_2$O and 15 eq CH$_3$I were added and after 5 h the mixture was worked up as described for 20E 22-methyl ether. Purification of the putative compounds was obtained by semi-preparative C$_{18}$-HPLC with isocratic 60% MeOH/H$_2$O, where 20E 3,22-dimethyl ether eluted after 21 min (28.4 mg, 25%) and 20E 2,22-dimethyl ether eluted after 24 min (45.8 mg, 40%). Full characterization was obtained by 400 MHz NMR analysis (Table 3a-3e) and CIMS (20E 2,22-dimethyl ether: Calc. [M+H]$^+$=509.3478. Found [M+H]$^+$=509.3481. 20E 3,22-dimethyl ether: Calc. [M+H]$^+$=509.3478. Found [M+H]$^+$=509.3486).

Preparation of 20E 14,22-dimethyl ether

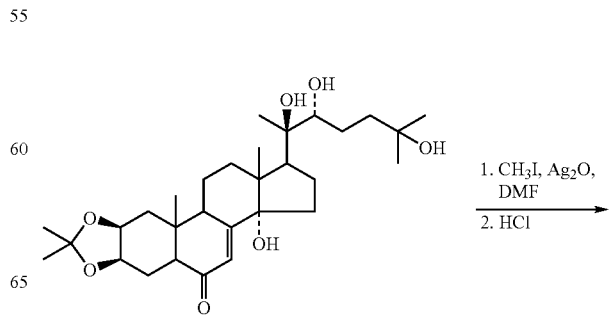

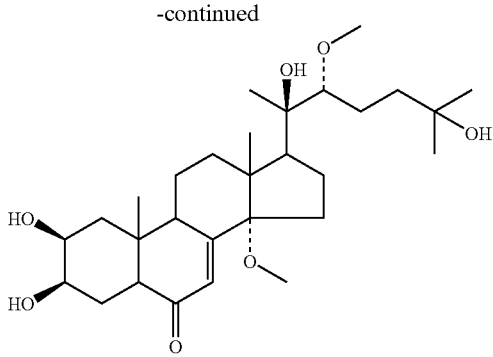

Ag₂O (84.7 mg, 10 eq) and CH₃I (48 μL, 20 eq) were added to a solution of 20E 2,3-acetonide (19.0 mg, 36.5 μmol) in anhydrous DMF (1.5 mL) and the reaction was stirred at room temperature under anhydrous conditions. After 21 h of reaction, further Ag₂O (3×10 eq) and CH₃I (3×20 eq) were added at intervals of 10 h. After 51 h, the reaction was worked up and the 2,3-acetonide group removed as described for 20E 22-methyl ether. Purification was carried out first by semi-preparative $C_{18}$-HPLC with isocratic 60% MeOH/H₂O, where 1.9 mg of a main peak with R.t.=18 min was collected; subsequently, by a semi-preparative silica column with isocratic CH₂Cl₂/isopropanol/H₂O (160:30:1.5, v/v/v), where 20E 14,22-dimethyl ether was eluted after 16.3 min and yielded 1.0 mg (6%). Full characterization was obtained by 400 MHz NMR analysis (Table 3a-3e) and CIMS (Calc. $[M+H]^+$=509.3478. Found $[M+H]^+$=509.3441).

Preparation of 20E 2,3,14,22-tetramethyl ether

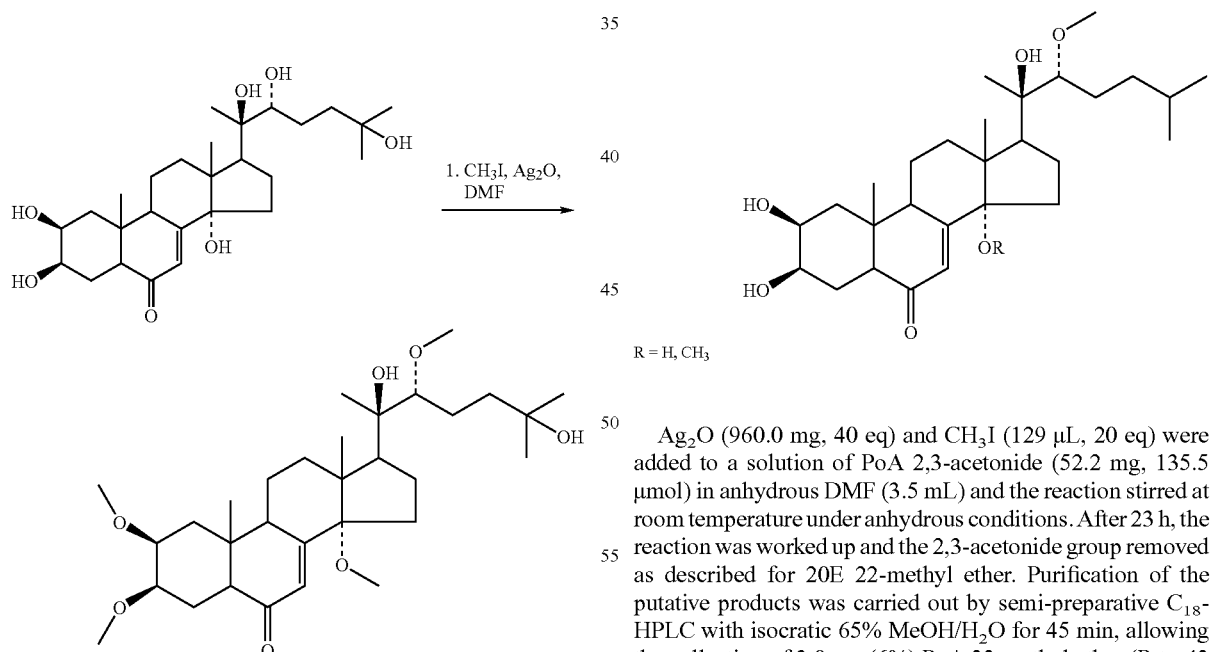

R = H, CH₃

Ag₂O (1.745 g, 23 eq) and CH₃I (1.175 mL, 60 eq) were added to a solution of 20E (155 mg, 324 μmol) in anhydrous DMF (4.0 mL) and the reaction was stirred at room temperature under anhydrous conditions. After 12 h, a further 19 eq Ag₂O and 60 eq CH₃I were added, following by further 60 eq CH₃I after 20 h of reaction. After a total time of 36 h the reaction was worked up as described for 20E 22-methyl ether. Purification was carried out by semi-preparative $C_{18}$-HPLC with isocratic 70% MeOH/H₂O, where 20E 2,3,14,22-tetramethyl ether eluted after 19 min and yielded 51 mg (30%). Characterization was carried out by 400 MHz NMR (Table 3a-3e) and CIMS (Calc. $[M+H]^+$=537.3791. Found $[M+H]^+$=537.3823). A One experiment confirmed the stereochemistry at C-14 as in 20E (irradiation at H-9 produced a 2.2% enhancement of the 14-OMe signal).

Preparation of PoA 22-methyl ether and PoA 14,22-dimethyl ether

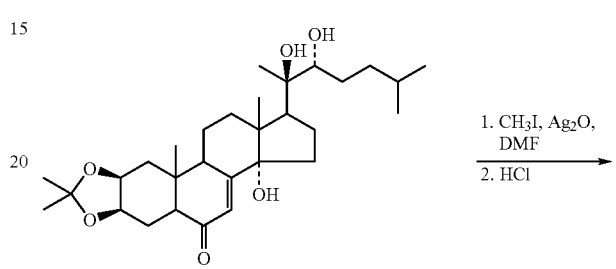

Ag₂O (960.0 mg, 40 eq) and CH₃I (129 μL, 20 eq) were added to a solution of PoA 2,3-acetonide (52.2 mg, 135.5 μmol) in anhydrous DMF (3.5 mL) and the reaction stirred at room temperature under anhydrous conditions. After 23 h, the reaction was worked up and the 2,3-acetonide group removed as described for 20E 22-methyl ether. Purification of the putative products was carried out by semi-preparative $C_{18}$-HPLC with isocratic 65% MeOH/H₂O for 45 min, allowing the collection of 3.0 mg (6%) PoA 22-methyl ether (R.t.=42 min), following by multiple injections of 5 mL MeOH, allowing the elution of the dimethylated compound, which was then purified by preparative $C_{18}$-HPLC with isocratic 75% MeOH/H₂O (3.8 mg, 8%). Full characterization was obtained by 300 MHz NMR analysis (Table 3a-3e) and CIMS (PoA 22-methyl ether: Calc. $[M+H]^+$=479.3373. Found $[M+H]^+$=479.3369. PoA 14,22-dimethyl ether: Calc. $[M+H]^+$=493.3529. Found $[M+H]^+$=493.3526).

Preparation of dacryhainansterone 22-methyl ether

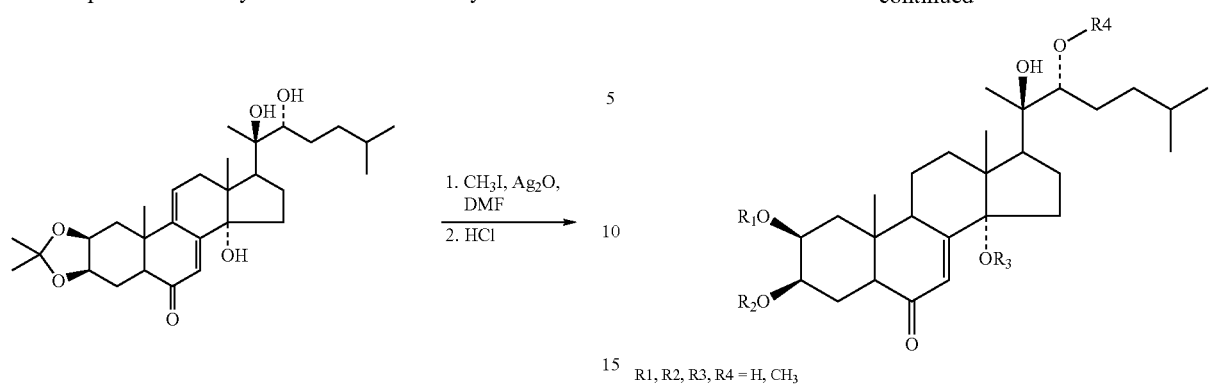

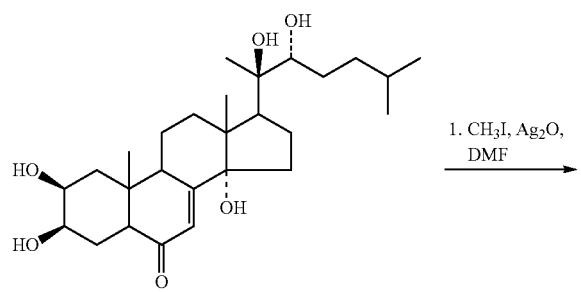

Dacryhainansterone 22-methyl ether was obtained as side-product of a reaction of methylation of PoA 2,3-acetonide (61.0 mg, 121.0 μmol) with Ag$_2$O (278.0 mg, 10 eq) and CH$_3$I (121 μL, 15 eq) in anhydrous DMF (1.7 mL) for 46 h. The dacryhainansterone-like conjugated system ($\lambda_{max}$=299 nm) was detected by HPLC with DAD monitoring at k=300 nm. The product was purified by preparative C$_{18}$-HPLC with isocratic 75% MeOH/H$_2$O(R.t.=24.7 min), followed by semi-preparative C$_{18}$-HPLC with isocratic 65% MeOH/H$_2$O (R.t.=26.9 min), which yielded 1.7 mg dacryhainansterone 22-methyl ether (3%). Full characterization was obtained by 300 MHz NMR analysis (Table 3a-3e) and CIMS (dacryhainansterone 22-methyl ether: Calc. [M+H]$^+$=477.3216. Found [M+H]$^+$=477.3224).

Preparation of PoA 2-methyl ether, PoA 14-methyl ether PoA 2,22-dimethyl ether and PoA 3,22-dimethyl ether

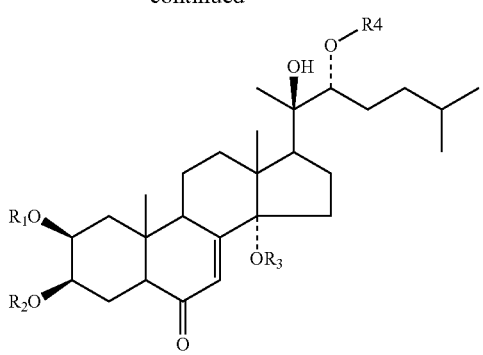

R1, R2, R3, R4 = H, CH$_3$

Ag$_2$O (590.0 mg, 10 eq) and CH$_3$I (238 μL, 15 eq) were added to a solution of PoA (118.1 mg, 254.6 μmol) in anhydrous DMF (3.3 mL) and the reaction stirred at room temperature under anhydrous conditions. The reaction was stopped after 18 h, to obtain PoA 2,22-methyl ether, or else after 46 h, to obtain all the other products. In all cases the work-up was carried out as described for 20E 22-methyl ether. Purification of the putative products was performed by preparative C$_{18}$-HPLC with isocratic 75% MeOH/H$_2$O, which allowed the collection of 6% PoA 2-methyl ether (R.t.=20.2 min), 2% PoA 14-methyl ether (R.t.=24.7 min), 16.0% PoA 2,22-methyl ether (R.t.=39.7 min) and 7% PoA 3,22-methyl ether (R.t.=32.9 min). Full characterization was obtained by 300 MHz NMR analysis (Table 3a-3e) and CIMS (PoA 2-methyl ether: Calc. [M+H]$^+$=479.3373. Found [M+H]$^+$=479.3388. PoA 14-methyl ether: Calc. [M+H]$^+$=479.3373. Found [M+H]$^+$=479.3363. PoA 3,22-dimethyl ether: Calc. [M+H]$^+$=493.3529. Found [M+H]$^+$=493.3528. PoA 2,22-dimethyl ether: Calc. [M+H]$^+$=493.3529. Found [M+H]$^+$=493.3525.

The HPLC retention times for the various ether derivatives of 20E at different HPLC solvent systems is shown in Table 1 and 2. The NMR data obtained for each compound synthesized are summarized in Tables 3a-3e.

TABLE 1

RP- and NP-HPLC retention times for 20E alkyl ether derivatives.[a]

| | RP-HPLC | | NP-HPLC | |
|---|---|---|---|---|
| | method A | method B | method C | method D |
| 20-hydroxyecdysone (20E) | 9.1 | 7.2 | — | 6.6 |
| 20E 2-methyl ether | 11.1 | 8.7 | — | 4.4 |
| 20E 3-methyl ether | 10.6 | 8.4 | — | 4.3 |
| 20E 14-methyl ether | 11.2 | 9.6 | — | 4.1 |
| 20E 22-methyl ether | 12.3 | 9.4 | — | 6.3 |
| 20E 25-methyl ether | 11.4 | 9.8 | — | 4.4 |
| 20E 2,22-dimethyl ether | 14.1 | 11.3 | 5.5 | — |
| 20E 3,22-dimethyl ether | 13.5 | 10.8 | 5.1 | — |
| 20E 14,22-dimethyl ether | 14.3 | 11.5 | 5.2 | — |
| 20E 22,25-dimethyl ether | 14.7 | 12.3 | 6.6 | — |
| 20E 2,3,14,22-tetramethyl ether | 17.9 | 15.1 | 2.1 | — |
| 20E 22-ethyl ether | 14.6 | 11.3 | — | 5.1 |
| 20E 22-propyl ether | 17.5 | 14.2 | — | 4.9 |
| 20E 22-buthyl ether | 19.2 | 15.7 | 9.9 | — |
| 20E 22-allyl ether | 15.9 | 12.6 | 10.0 | — |

TABLE 1-continued

RP- and NP-HPLC retention times for 20E alkyl ether derivatives.[a]

| | RP-HPLC | | NP-HPLC | |
|---|---|---|---|---|
| | method A | method B | method C | method D |
| 20E 22-benzyl ether | 18.5 | 15.3 | 9.8 | — |
| 20E 22-(2'R,S)-2'-ethyloxiranyl ether | 17.1 | 14.1 | 11.2 | — |

[a]Retention times expressed in minutes
Method A: $C_{18}$-RP-HPLC (150 × 4.6 mm, 5 mm particle size, gradient from 30% to 100% methanol/water in 25 min, flow-rate = 1 mL/min, λ = 242 nm)
Method B: $C_6$-RP-HPLC (150 × 4.6 mm, 5 mm particle size, gradient from 30% to 100% methanol/water in 25 min, flow-rate = 1 mL/min, λ = 242 nm)
Method C: diol NP-HPLC (150 × 4.6 mm, 5 mm particle size, gradient from 2% to 10% methanol/dichloromethane in 20 min, flow-rate = 1 mL/min, λ = 242 nm)
Method D: diol NP-HPLC (150 × 4.6 mm, 5 mm particle size, gradient from 4% to 10% methanol/dichloromethane in 20 min, flow-rate = 1 mL/min, λ = 242 nm)

TABLE 2

RP- and NP-HPLC retention times for PoA alkyl ether derivatives.[a]

| | RP-HPLC | | NP-HPLC |
|---|---|---|---|
| | method A | method B | method C |
| ponasterone A (PoA) | 14.7 | 12.0 | 11.1 |
| PoA 2-methyl ether | 16.5 | 14.5 | 3.6 |
| PoA 14-methyl ether | 17.7 | 15.3 | 4.9 |
| PoA 22-methyl ether | 18.0 | 14.8 | 5.7 |
| dacryhainansterone 22-methyl ether | 17.2 | 14.3 | 6.6 |
| PoA 2,22-dimethyl ether | 19.8 | 16.6 | 2.7 |
| PoA 3,22-dimethyl ether | 18.9 | 16.1 | 2.7 |
| PoA 14,22-dimethyl ether | 20.7 | 17.7 | 3.5 |

[a]Retention times expressed in minutes
Method A: $C_{18}$-RP-HPLC (150 × 4.6 mm, 5 mm particle size, gradient from 30% to 100% methanol/water in 25 min, flow-rate = 1 mL/min, λ = 242 nm and 300 nm)
Method B: $C_6$-RP-HPLC (150 × 4.6 mm, 5 mm particle size, gradient from 30% to 100% methanol/water in 25 min, flow-rate = 1 mL/min, λ = 242 nm and 300 nm)
Method C: Apex II diol NP-HPLC (150 × 4.6 mm, 5 mm particle size, isocratic 2% methanol in dichloromethane, flow-rate = 1 mL/min, λ = 242 nm and 300 nm)

TABLE 3a

NMR data of monomethyl 20E derivatives.

| Position | 20E 2-methyl ether[a] $^{13}$C | 20E 2-methyl ether[a] $^1$H | 20E 3-methyl ether[a] $^{13}$C | 20E 3-methyl ether[a] $^1$H | 20E 14-methyl ether[a] $^{13}$C | 20E 14-methyl ether[a] $^1$H | 20E 22-methyl ether[a] $^{13}$C | 20E 22-methyl ether[a] $^1$H | 20E 25-methyl ether[b] $^{13}$C | 20E 25-methyl ether[b] $^1$H |
|---|---|---|---|---|---|---|---|---|---|---|
| 1 | 34.76 | ax 1.43 eq 1.87 | 38.28 | ax 1.41 eq 1.80 | 37.22 | ax 1.45 eq 1.78 | 37.32 | ax 1.43 eq 1.78 | 37.32 | ax 1.43* eq 1.80* |
| 2 | 78.28 | 3.47 | 68.77 | 3.85 | 68.64 | 3.81 | 68.68 | 3.83 | 68.68 | 3.83 |
| 3 | 64.73 | 4.19 | 78.57 | 3.52 | 68.38 | 3.95 | 68.49 | 3.94 | 68.50 | 3.93 |
| 4 | 32.49 | eq 1.75 | 28.58 | ax 1.90 eq 1.59 | 33.03 | ax 1.71 eq 1.65 | 32.83 | ax 1.70 eq 1.75 | 32.84 | ax 1.71* eq 1.77* |
| 5 | 51.97 | 2.41 | 52.05 | 2.21 | 51.68 | 2.42 | 51.77 | 2.39 | 51.78 | 2.39 |
| 6 | | | 206.38 | | 205.40 | | 206.47 | | 206.45 | |
| 7 | 122.14 | 5.81 | 122.10 | 5.82 | 125.97 | 5.77 | 122.10 | 5.81 | 122.10 | 5.80 |
| 8 | | | 168.29 | | 163.48 | | 168.02 | | 168.03 | |
| 9 | 35.09 | 3.14 | 35.11 | 3.15 | 35.42 | 2.78 | 35.06 | 3.15 | 35.00 | 3.15 |
| 10 | 39.16 | | 39.13 | | 39.30 | | 39.25 | | 38.29 | |
| 11 | 21.48 | ax 1.65* eq 1.78* | 21.55 | ax 1.65* eq 1.78* | 21.51 | ax 1.80* eq 1.63* | 21.49 | ax 1.65* eq 1.78* | 21.50 | ax 1.70* eq 1.80* |
| 12 | 32.49 | ax 2.13 eq 1.87 | 32.48 | ax 2.13 eq 1.87 | 31.90 | ax 2.22 eq 1.84 | 32.53 | ax 2.13 eq 1.87 | 32.49 | ax 2.13 eq 1.85* |
| 13 | u.s.s. | | u.s.s. | | u.s.s. | | u.s.s. | | u.s.s. | |
| 14 | 85.23 | | 85.22 | | 90.93 | | 85.23 | | 85.17 | |
| 15 | 31.76 | a 1.96* b 1.55* | 31.77 | a 1.96* b 1.55* | 24.35 | a 1.92* b 1.63* | 31.76 | a 1.96* b 1.55* | 31.73 | a 1.98* b 1.60* |
| 16 | 21.48 | a 1.98* b 1.75* | 21.47 | a 1.98* b 1.75* | 21.51 | a 1.98* b 1.73* | 21.49 | a 1.98* b 1.75* | 21.50 | a 1.95* b 1.75* |
| 17 | 50.52 | 2.38 | 50.50 | 2.39 | 50.49 | 2.38 | 50.70 | 2.31 | 50.51 | 2.35 |
| 18-Me | 18.05 | 0.88 | 18.04 | 0.89 | 18.59 | 0.94 | 18.16 | 0.89 | 18.03 | 0.88 |
| 19-Me | 24.39 | 0.97 | 24.40 | 0.95 | 24.60 | 0.98 | 24.39 | 0.96 | 24.39 | 0.96 |
| 20 | 77.91 | | 77.90 | | 77.80 | | 79.12 | | 77.87 | |
| 21-Me | 21.04 | 1.20 | 21.02 | 1.20 | 21.51 | 1.18 | 21.66 | 1.22 | 21.01 | 1.18 |
| 22 | 78.42 | 3.33 | 78.41 | 3.33 | 78.42 | 3.33 | 89.86 | 2.95 | 78.31 | 3.33 |
| 23 | 27.32 | a 1.32* b 1.67* | 27.31 | a 1.29* b 1.66* | 27.31 | a 1.29* b 1.66* | 27.52 | a 1.33* b 1.65* | 26.85 | a 1.30* b 1.65* |
| 24 | 42.38 | a 1.75* b 1.45* | 42.38 | a 1.79* b 1.43* | 42.33 | a 1.79* b 1.43* | 42.31 | a 1.75* b 1.45* | 39.23 | a 1.78* b 1.46* |
| 25 | 71.3 | | 71.30 | | 71.23 | | 71.29 | | 76.16 | |
| 26-Me | 28.93 | 1.19* | 28.90 | 1.19* | 28.76 | 1.19* | 28.83 | 1.18* | 25.52 | 1.16* |
| 27-Me | 29.72 | 1.20* | 29.71 | 1.20* | 29.90 | 1.20* | 29.58 | 1.19* | 25.27 | 1.17* |
| 2-OMe | 56.08 | 3.39 | — | — | — | — | — | — | — | — |
| 3-OMe | — | — | 57.32 | 3.40 | — | — | — | — | — | — |
| 14-OMe | — | — | — | — | 49.90 | 2.97 | — | — | — | — |
| 22-OMe | — | — | — | — | — | — | 61.92 | 3.50 | — | — |
| 25-OMe | — | — | — | — | — | — | — | — | 49.36 | 3.19 |

Samples were dissolved in methanol-$d_4$. Chemical shifts are expressed in parts per million (ppm).
u.s.s.: under solvent signal.
[a]$^1$H-NMR collected at 400 MHz, $^{13}$C-NMR at 100 MHz.
[b]$^1$H-NMR collected at 300 MHz, $^{13}$C-NMR at 75 MHz.
*assigned comparing to literature data for 20E (www.ecdybase.org)

TABLE 3b

NMR data of multi-methyl derivatives of 20E.

| Position | 20E 2,22-dimethyl ether[a] | | 20E 3,22-dimethyl ether[a] | | 20E 14,22-dimethyl ether[a] | | 20E 22,25-dimethyl ether[b] | | 20E 2,3,14,22-tetramethyl ether[a] | |
|---|---|---|---|---|---|---|---|---|---|---|
| | $^{13}$C | $^{1}$H | $^{13}$C | $^{1}$H | $^{13}$C | $^{1}$H | $^{13}$C | $^{1}$H | $^{13}$C | $^{1}$H |
| 1 | 34.76 | ax 1.40 eq 1.85 | 38.28 | ax 1.43 eq 1.84 | 37.21 | ax 1.43 eq 1.79 | 37.34 | ax 1.43* eq 1.80* | 35.33 | ax 1.43 eq 1.88 |
| 2 | 78.29 | 3.48 | 68.76 | 3.83 | 68.66 | 3.80 | 68.91 | 3.83 | 78.98 | 3.53 |
| 3 | 64.75 | 4.18 | 78.56 | 3.51 | 68.40 | 3.96 | 68.50 | 3.94 | 74.74 | 3.78 |
| 4 | 32.53 | ax 1.70 eq 1.74 | 32.52 | ax 1.90 eq 1.60 | 32.08 | ax 1.67 eq 1.73 | 32.87 | ax 1.71* eq 1.77* | 28.64 | ax 1.45 eq 1.95 |
| 5 | 51.97 | 2.40 | 52.05 | 2.20 | 51.69 | 2.41 | 51.79 | 2.36 | 52.14 | 2.27 |
| 6 | 206.21 | | 206.38 | | 205.54 | | 206.44 | | 205.01 | |
| 7 | 122.12 | 5.81 | 122.08 | 5.82 | 125.95 | 5.78 | 122.07 | 5.80 | 126.00 | 5.79 |
| 8 | 167.94 | | 168.31 | | 163.60 | | 168.10 | | 163.73 | |
| 9 | 35.07 | 3.14 | 35.10 | 3.14 | 36.00 | 2.76 | 35.00 | 3.15 | 35.47 | 2.78 |
| 10 | 39.15 | | 39.13 | | 39.32 | | 38.14 | | 39.16 | |
| 11 | 21.50 | ax 1.65* eq 1.78* | 21.50 | ax 1.65* eq 1.78* | 21.54 | ax 1.73* eq 1.82* | 21.54 | ax 1.70* eq 1.80* | 21.52 | ax 1.65* eq 1.78* |
| 12 | 32.53 | ax 2.12 eq 1.89 | 31.76 | ax 2.13 eq 1.85 | 31.97 | ax 2.19 eq 1.82* | 32.55 | ax 2.10 eq 1.85* | 31.91 | ax 2.21 eq 1.81 |
| 13 | u.s.s. | | u.s.s. | | u.s.s. | | u.s.s. | | u.s.s. | |
| 14 | 85.23 | | 85.23 | | 90.98 | | 85.17 | | 90.94 | |
| 15 | 31.75 | a 1.98* b 1.61* | 28.57 | a 2.00* b 1.55* | 24.36 | a 1.94* b 1.63* | 31.75 | a 1.98* b 1.60* | 24.37 | a 1.92* b 1.65* |
| 16 | 21.50 | a 2.00* b 1.75* | 21.55 | a 1.95* b 1.75* | 21.54 | a 2.00* b 1.75* | 21.54 | a 1.95* b 1.75* | 21.52 | a 2.03* b 1.75* |
| 17 | 50.72 | 2.32 | 50.70 | 2.30 | 50.71 | 2.31 | 50.72 | 2.32 | 50.69 | 2.31 |
| 18-Me | | 0.90 | 18.15 | 0.89 | 18.72 | 0.94 | 18.17 | 0.89 | 18.05 | 0.94 |
| 19-Me | 24.36 | 0.97 | 24.40 | 0.95 | 24.61 | 0.98 | 24.40 | 0.96 | 24.39 | 0.98 |
| 20 | 79.10 | | 79.11 | | 79.07 | | 79.12 | | 77.91 | |
| 21-Me | 21.67 | 1.22 | 21.65 | 1.21 | 21.70 | 1.20 | 21.64 | 1.21 | 21.69 | 1.20 |
| 22 | 89.86 | 2.95 | 89.85 | | 89.89 | 2.93 | 90.15 | 2.95 | 89.84 | 2.93 |
| 23 | 27.51 | a 1.32* b 1.68* | 27.51 | a 1.38* b 1.65* | 27.52 | a 1.67* b 1.36* | 27.00 | a 1.67* b 1.36* | 27.50 | a 1.34* b 1.60* |
| 24 | 42.33 | a 1.75* b 1.47* | 42.31 | a 1.75* b 1.45* | 42.31 | a 1.75* b 1.46* | 39.26 | a 1.30* b 1.65* | 42.32 | a 1.74* b 1.45* |
| 25 | 71.27 | | 71.29 | | 71.31 | | 76.10 | | 71.30 | |
| 26-Me | 28.83 | 1.18* | 28.82 | 1.18* | 28.77 | 1.18* | 25.53 | 1.16 | 28.75 | 1.18* |
| 27-Me | 29.58 | 1.20* | 29.58 | 1.20* | 29.70 | 1.19* | 25.26 | 1.16 | 29.69 | 1.20* |
| 2-OMe | 56.06 | 3.39 | — | — | — | — | — | — | 56.24 | 3.39 |
| 3-OMe | — | — | 57.32 | 3.40 | — | — | — | — | 57.11 | 3.40 |
| 14-OMe | — | — | — | — | u.s.s. | 2.97 | — | — | 49.79 | 3.39 |
| 22-OMe | 61.89 | 3.51 | 61.91 | 3.51 | 61.87 | 3.50 | 61.93 | 3.51 | 61.80 | 3.50 |
| 25-OMe | — | — | — | — | — | — | 49.38 | 3.18 | — | — |

Samples were dissolved in methanol-$d_4$. Chemical shifts are expressed in parts per million (ppm).
u.s.s.: under solvent signal.
[a]$^{1}$H-NMR collected at 400 MHz, $^{13}$C-NMR at 100 MHz.
[b]$^{1}$H-NMR collected at 300 MHz, $^{13}$C-NMR at 75 MHz.
*assigned comparing to literature data for 20E (www.ecdybase.org)

TABLE 3c

NMR data of 22-alkylated derivatives of 20E.

| Position | 20E 22-ethyl ether[a] | | 20E 22-n-propyl ether[a] | | 20E 22-n-butyl ether[b] | |
|---|---|---|---|---|---|---|
| | $^{13}$C | $^{1}$H | $^{13}$C | $^{1}$H | $^{13}$C | $^{1}$H |
| 1 | 37.36 | ax 1.43 eq 1.78 | 38.74 | ax 1.43 eq 1.80 | 37.34 | ax 1.43 eq 1.80 |
| 2 | 68.68 | 3.83 | 70.09 | 3.82 | 68.68 | 3.83 |
| 3 | 68.50 | 3.94 | 69.90 | 3.94 | 68.50 | 3.94 |
| 4 | 32.53 | ax 1.77 eq 1.72 | 34.27 | ax 1.71 eq 1.77 | 32.86 | ax 1.71* eq 1.77* |
| 5 | 51.77 | 2.37 | 53.19 | 2.37 | 51.78 | 2.37 |
| 6 | 206.43 | | 207.85 | | 206.43 | |
| 7 | 122.10 | 5.80 | 123.51 | 5.80 | 122.11 | 5.80 |
| 8 | 168.00 | | 169.42 | | 168.01 | |
| 9 | 35.07 | 3.14 | 36.48 | 3.14 | 35.07 | 3.14 |

TABLE 3c-continued

NMR data of 22-alkylated derivatives of 20E.

| Position | 20E 22-ethyl ether[a] $^{13}$C | 20E 22-ethyl ether[a] $^{1}$H | 20E 22-n-propyl ether[a] $^{13}$C | 20E 22-n-propyl ether[a] $^{1}$H | 20E 22-n-butyl ether[b] $^{13}$C | 20E 22-n-butyl ether[b] $^{1}$H |
|---|---|---|---|---|---|---|
| 10 | 39.26 | | 40.66 | | 39.26 | |
| 11 | 21.52 | ax 1.78* eq 1.70* | 22.94 | ax 1.73* eq 1.82* | 21.53 | ax 1.73* eq 1.82* |
| 12 | 31.76 | ax 2.12 eq 1.88 | 33.93 | ax 2.12 eq 1.89 | 32.52 | ax 2.11 eq 1.80 |
| 13 | u.s.s. | | u.s.s. | | 48.63 | |
| 14 | 91.24 | | 86.64 | | 85.22 | |
| 15 | 30.75 | a 1.99* b 1.62* | 33.17 | a 1.98* b 1.61* | 31.78 | a 1.98* b 1.61* |
| 16 | 21.52 | a 1.98* b 1.75* | 22.94 | a 2.10* b 1.90* | 21.53 | a 2.10* b 1.90* |
| 17 | 50.73 | 2.33 | 52.14 | 2.35 | 50.73 | 2.33 |
| 18-Me | 18.16 | 0.90 | 19.58 | 0.89 | 18.18 | 0.89 |
| 19-Me | 24.40 | 0.96 | 25.80 | 0.96 | 24.40 | 0.96 |
| 20 | 78.95 | | 80.57 | | 79.15 | |
| 21-Me | 21.86 | 1.23 | 23.30 | 1.24 | 21.90 | 1.23 |
| 22 | 88.05 | 3.07 | 89.37 | 3.05 | 87.98 | 3.03 |
| 23 | 27.55 | a 1.35* b 1.65* | 29.02 | a 1.67* b 1.36* | 27.60 | a 1.67* b 1.36* |
| 24 | 42.40 | a 1.76* b 1.48* | 43.83 | a 1.78* b 1.46* | 42.43 | a 1.78* b 1.39 |
| 25 | 71.31 | | 72.74 | | 71.33 | |
| 26-Me | 28.87 | 1.18* | 30.23 | 1.18 | 28.84 | 1.17 |
| 27-Me | 29.58 | 1.19* | 31.00 | 1.19 | 29.60 | 1.19 |
| 28-(22OCH$_2$CH$_3$) | 58.31 | 3.60 | — | — | — | — |
| 29-(22OCH$_2$CH$_3$) | 18.36 | 1.18 | — | — | — | — |
| 28-(22OCH$_2$CH$_2$CH$_3$) | — | — | 77.93 | a 3.66 b 3.51 | — | — |
| 29-(22OCH$_2$CH$_2$CH$_3$) | — | — | 24.63 | 1.62 | — | — |
| 30-(22OCH$_2$CH$_2$CH$_3$) | — | — | 11.10 | 0.94 | — | — |
| 28(22-OCH$_2$CH$_2$CH$_2$CH$_3$) | — | — | — | — | 74.57 | a 3.70 b 3.54 |
| 29(22-OCH$_2$CH$_2$CH$_2$CH$_3$) | — | — | — | — | 33.70 | a 1.56 b 1.59 |
| 30(22-OCH$_2$CH$_2$CH$_2$CH$_3$) | — | — | — | — | 20.53 | a 1.41 b 1.27 |
| 31(22-OCH$_2$CH$_2$CH$_2$CH$_3$) | — | — | — | — | 14.41 | 0.94 |

Samples were dissolved in methanol-d$_4$. Chemical shifts are expressed in parts per million (ppm).
u.s.s.: under solvent signal.
[a]$^{1}$H-NMR collected at 400 MHz, $^{13}$C-NMR at 100 MHz.
[b]$^{1}$H-NMR collected at 300 MHz, $^{13}$C-NMR at 75 MHz.
*assigned comparing to literature data for 20E (www.ecdybase.org)

TABLE 3d

NMR data of other 22-substituted derivatives of 20E.

| Position | 20E 22-allyl ether[b] $^{13}$C | 20E 22-allyl ether[b] $^{1}$H | 20E 22-benzyl ether[a] $^{13}$C | 20E 22-benzyl ether[a] $^{1}$H | 20E 22-(2'-ethyl)-oxiranyl ether[b] $^{13}$C | 20E 22-(2'-ethyl)-oxiranyl ether[b] $^{1}$H |
|---|---|---|---|---|---|---|
| 1 | 37.33 | ax 1.44 eq 1.78* | 37.38 | ax 1.44* eq 1.78* | 37.33 | ax 1.42* eq 1.78* |
| 2 | 68.68 | 3.83 | 69.68 | 3.83 | 68.71 | 3.82 |
| 3 | 68.49 | 3.94 | 68.50 | 3.95 | 68.50 | 3.94 |
| 4 | 32.85 | ax 1.65* eq 1.72* | 32.85 | ax 1.65* eq 1.72* | 32.89 | ax 1.65* eq 1.72* |
| 5 | 51.78 | 2.38 | 51.79 | 2.38 | 51.79 | 2.38 |
| 6 | 206.42 | | 206.44 | | 206.46 | |
| 7 | 122.11 | 5.80 | 122.14 | 5.81 | 122.13 | 5.80 |
| 8 | 168.00 | | 168.00 | | 167.65 | |
| 9 | 35.10 | 3.15 | 36.58 | 3.15 | 35.12 | 3.14 |
| 10 | 39.26 | | 39.29 | | 39.22 | |
| 11 | 21.51 | ax 1.65* eq 1.71* | 21.54 | ax 1.65* eq 1.71* | 21.53 | ax 1.73* eq 1.82* |

TABLE 3d-continued

NMR data of other 22-substituted derivatives of 20E.

| Position | 20E 22-allyl ether[b] $^{13}$C | 20E 22-allyl ether[b] $^{1}$H | 20E 22-benzyl ether[a] $^{13}$C | 20E 22-benzyl ether[a] $^{1}$H | 20E 22-(2'-ethyl)-oxiranyl ether[b] $^{13}$C | 20E 22-(2'-ethyl)-oxiranyl ether[b] $^{1}$H |
|---|---|---|---|---|---|---|
| 12 | 32.53 | ax 2.12 eq 1.69 | 32.55 | ax 2.12* eq 1.69* | 32.36 | ax 2.11 eq 1.80 |
| 13 | u.s.s. | | u.s.s. | | 48.63 | |
| 14 | 85.21 | | 85.22 | | 85.30 | |
| 15 | 31.78 | a 2.00 b 1.55* | 31.80 | a 2.00* b 1.55* | 31.69 | a 1.98* b 1.61* |
| 16 | 21.51 | a 1.95* b 1.71 | 21.54 | a 1.95* b 1.71* | 22.16 | a 2.10* b 1.90* |
| 17 | 50.78 | 2.33 | 50.88 | 2.35 | 50.82 | 2.33 |
| 18-Me | 18.16 | 0.89 | 18.17 | 0.91 | 17.63 | 0.84 |
| 19-Me | 24.40 | 0.96 | 24.40 | 0.96 | 24.45 | 0.96 |
| 20 | 79.17 | | 79.46 | | 85.24 | |
| 21-Me | 21.82 | 1.25 | 21.85 | 1.29 | 23.11 | 1.20 |
| 22 | 87.93 | 3.12 | 87.90 | 3.26 | 83.34 | 3.73 |
| 23 | 27.54 | a 1.65* b 1.27 | 27.58 | a 1.65* b 1.27* | 30.47 | a 1.52* b 1.36* |
| 24 | 42.36 | a 1.75* b 1.39 | 42.31 | a 1.75* b 1.39* | 42.03 | a 1.78* b 1.39 |
| 25 | 71.32 | | 71.30 | | 71.15 | |
| 26-Me | 28.83 | 1.17 | 28.81 | 1.14 | 28.95 | 1.19 |
| 27-Me | 29.61 | 1.19 | 29.61 | 1.15 | 29.52 | 1.19 |
| 28(22-OCH$_2$CH=CH$_2$) | 75.75 | a 4.26 b 4.09 | — | — | — | — |
| 29(22-OCH$_2$CH=CH$_2$) | 137.03 | 5.97 | — | — | — | — |
| 30(22-OCH$_2$CH=CH$_2$) | 116.37 | a 5.26 b 5.11 | — | — | — | — |
| 22OCH$_2$-Ph | — | — | 76.64 | a 4.82 b 4.59 | — | — |
| Ph-1'-C | — | — | 140.55 | | — | — |
| Ph-m (2H) | — | — | 129.28 | 7.28 | — | — |
| Ph-o (2H) | — | — | 128.51 | 7.33 | — | — |
| Ph-p (2H) | — | — | 129.07 | 7.40 | — | — |
| 22OC(CH$_2$O)CH$_2$CH$_3$ | — | — | — | — | 110.25 | |
| 22OC(CH$_2$O)CH$_2$CH$_3$ | — | — | — | — | 63.54 | a 3.49 b 3.39 |
| 22OC(CH$_2$O)CH$_2$CH$_3$ | — | — | — | — | 24.84 | a 1.58 b 1.87 |
| 22OC(CH$_2$O)CH$_2$CH$_3$ | — | — | — | — | 9.03 | 0.93 |

Samples were dissolved in methanol-d$_4$. Chemical shifts are expressed in parts per million (ppm).
u.s.s.: under solvent signal.
[a]$^{1}$H-NMR collected at 400 MHz, $^{13}$C-NMR at 100 MHz.
[b]$^{1}$H-NMR collected at 300 MHz, $^{13}$C-NMR at 75 MHz.
*assigned comparing to literature data for 20E (www.ecdybase.org)

TABLE 3e

NMR data of methylated derivatives of PoA.

| Position | dacryhainansterone 22-methyl ether $^{1}$H | PoA 2-methyl ether $^{1}$H | PoA 14-methyl ether $^{1}$H | PoA 22-methyl ether $^{13}$C | PoA 22-methyl ether $^{1}$H | PoA 2,22-dimethyl ether $^{1}$H | PoA 3,22-dimethyl ether $^{1}$H | PoA 14,22-dimethy $^{1}$H |
|---|---|---|---|---|---|---|---|---|
| 1 | | | | 37.35 | ax 1.43* eq 1.79* | | | |
| 2 | 3.70 | 3.47 | 3.79 | 68.69 | 3.83 | 3.46 | 3.84 | 3.80 |
| 3 | 3.83 | 4.18 | 3.94 | 68.50 | 3.94 | 4.17 | u.s.s. | 3.95 |
| 4 | | | | 32.85 | ax 1.70* eq 1.74* | | | |
| 5 | 2.39 | 2.38 | 2.40 | 51.78 | 2.39 | 2.40 | 2.21 | 2.40 |
| 6 | | | | 206.53 | | | | |
| 7 | 5.74 | 5.80 | 5.78 | 122.10 | 5.80 | 5.81 | 5.81 | 5.78 |
| 8 | | | | 168.00 | | | | |
| 9 | | 3.14 | 2.76 | 35.05 | 3.14 | 3.14 | 3.15 | 2.76 |
| 10 | | | | 39.25 | | | | |
| 11 | 6.27 | | | 21.60 | ax 1.81* eq 1.70* | | | |

TABLE 3e-continued

NMR data of methylated derivatives of PoA.

| Position | dacryhainansterone 22-methyl ether $^1H$ | PoA 2-methyl ether $^1H$ | PoA 14-methyl ether $^1H$ | PoA 22-methyl ether $^{13}C$ | PoA 22-methyl ether $^1H$ | PoA 2,22-dimethyl ether $^1H$ | PoA 3,22-dimethyl ether $^1H$ | PoA 14,22-dimethy $^1H$ |
|---|---|---|---|---|---|---|---|---|
| 12 | ax 2.68 | ax 2.12 | ax 2.20 | 32.55 | ax 2.09 eq 1.88* | ax 2.11 | ax 2.12 | ax 2.19 |
| 13 | | | | u.s.s. | | | | |
| 14 | | | | 85.23 | | | | |
| 15 | | | | 31.75 | a 1.96* b 1.59* | | | |
| 16 | | | | 21.60 | a 1.99* b 1.70* | | | |
| 17 | 2.43 | 2.38 | 2.35 | 50.66 | 2.30 | 2.30 | 2.30 | 2.28 |
| 18-Me | 0.89 | 0.89 | 0.89 | 18.15 | 0.89 | 0.88 | 0.88 | 0.90 |
| 19-Me | 0.10 | 0.97 | 0.97 | 24.39 | 0.96 | 0.97 | 0.94 | 0.98 |
| 20 | | | | 79.02 | | | | |
| 21-Me | 1.19 | 1.17 | 1.15 | 21.51 | 1.19 | 1.19 | 1.19 | 1.18 |
| 22 | 2.96 | u.s.s. | u.s.s. | 89.60 | 2.95 | 2.95 | 2.95 | 2.93 |
| 23 | | | | 37.82 | a 1.47* b 1.62* | | | |
| 24 | | | | 30.76 | a 1.46* b 1.21* | | | |
| 25 | | | | 29.49 | 1.56* | | | |
| 26-Me | 0.90** | 0.93* | 0.92* | 22.78 | 0.92* | 0.93* | 0.92* | 0.93* |
| 27-Me | 0.92** | 0.91* | 0.90* | 23.34 | 0.90* | 0.91* | 0.91* | 0.91* |
| 2-OCH$_3$ | — | 3.39 | — | — | — | 3.39 | 3.40 | — |
| 3-OCH$_3$ | — | — | — | — | — | — | — | — |
| 14-OCH$_3$ | — | — | 2.98 | — | — | — | — | 2.98 |
| 22-OCH$_3$ | 3.50 | — | — | 61.93 | 3.50 | 3.50 | 3.50 | 3.50 |

$^1$H-NMR collected at 300 MHz, $^{13}$C-NMR at 75 MHz. Samples were dissolved in methanol-d$_4$. Chemical shifts are expressed in parts per million (ppm).
u.s.s.: under solvent signal
*assigned comparing to literature data for PoA (www.ecdybase.org)
**assigned comparing to literature data for dacryhainansterone (www.ecdybase.org)

BII BIOASSAY

All compounds synthesized and purified were tested in a B$_{II}$ bioassay to assess their affinity for the ecdysteroid receptor. The steroid-responsive in vitro bioassays were performed using the *D. melanogaster* B$_{II}$ cell line. The assay is known to be largely free of metabolism and transport ambiguities. It is based on the l(2)mbn tumorous blood cell line from *Drosophila melanogaster* which expresses the ecdysteroid receptor complex and gives a characteristic response to ecdysteroids, which is measured turbidometrically. Under normal conditions, cells undergo mitosis and form an even covering of small cells. On exposure to a steroid agonist, cells are enlarged and undergo phagocytosis appearing as dense clumps of cells; absorbance then decreases. An antagonist prevents this response, leading to an increase in cell density; absorbance will then increase, relative to 20E-treated controls. To perform the bioassay, the compound to be tested is added to the wells of a 96-well microtiter plate (Nalge Nunc, Hereford, UK) in aliquots of 20 mL at several concentrations from $10^{-3}$ M to $10^{-10}$ M. Aliquots of 20 µL of 20E at $5\times10^{-8}$ M concentration were added to the wells to test for antagonist activity. The plates were incubated at 25° C. for 6-7 days and the response measured quantitatively using a plate reader (Anthos htl1, Anthos Labtec, Salzburg, Austria), which measured the absorbance at 405 nm. Results of the assays are shown in Table 4.

TABLE 4

B$_{II}$ bioassay results.

| Compound | EC$_{50}$ (M) |
|---|---|
| 20E | $7.6 \times 10^{-9}$ |
| 20E 2-methyl ether | $1.1 \times 10^{-6}$ |
| 20E 3-methyl ether | $6.0 \times 10^{-7}$ |
| 20E 14-methyl ether | $3.2 \times 10^{-6}$ |
| 20E 22-methyl ether | $6.3 \times 10^{-9}$ |
| 20E 25-methyl ether | $6.0 \times 10^{-8}$ |
| 20E 2,22-dimethyl ether | $9.3 \times 10^{-7}$ |
| 20E 3,22-dimethyl ether | $2.2 \times 10^{-7}$ |
| 20E 14,22-dimethyl ether | $2.5 \times 10^{-6}$ |
| 20E 22,25-dimethyl ether | $1.2 \times 10^{-7}$ |
| 20E 2,3,14,22-tetramethyl ether | $9.0 \times 10^{-5}$ |
| 20E 22-ethyl ether | $2.2 \times 10^{-8}$ |
| 20E 22-n-propyl ether | $8.3 \times 10^{-7}$ |
| 20E 22-n-butyl ether | $1.0 \times 10^{-7}$ |
| 20E 22-allyl ether | $1.6 \times 10^{-7}$ |
| 20E 22-benzyl ether | $2.2 \times 10^{-8}$ |
| 20E 22-(28R,S)-2'-ethyloxiranyl ether | $2.2 \times 10^{-5}$ |
| PoA | $2.6 \times 10^{-10}$ |
| PoA 2-methyl ether | $4.3 \times 10^{-8}$ |
| PoA 14-methyl ether | $6.0 \times 10^{-8}$ |
| PoA 22-methyl ether | $2.2 \times 10^{-8}$ |
| PoA 2,22-dimethyl ether | $3.0 \times 10^{-8}$ |
| PoA 3,22-dimethyl ether | $1.2 \times 10^{-8}$ |
| PoA 14,22-dimethyl ether | $1.7 \times 10^{-7}$ |
| dacryhainansterone 22-methyl ether | $1 \times 10^{-7}$ |

PREPARATION OF GENE EXPRESSION CASSETTES

This Example describes the construction of a gene expression cassette comprising a Group H nuclear receptor polynucleotide and polypeptide for use in a nuclear receptor-based inducible gene expression system. Applicants constructed a gene expression cassette based on the spruce budworm *Choristoneura fumiferana* EcR (CfEcR). The prepared receptor construct comprises a ligand binding domain of an EcR or a chimera of *Homo sapiens* RXRβ-LmUSP or *Mus musculus* RXRβ; and a GAL4 DNA binding domain (DBD) or a VP16 transactivation domain (AD). The reporter construct includes the reporter gene luciferase operably linked to a synthetic promoter construct that comprises a GAL4 response element to which the Gal4 DBD binds.

3.1—GAL4CfEcR-DEF/VP16-βRXREF-LmUSPEF:

The wild-type D, E, and F domains from spruce budworm *Choristoneura fumiferana* EcR ("CfEcR-DEF"; SEQ ID NO: 1) were fused to a GAL4 DNA binding domain ("Gal4DNABD" or "Gal4 DBD"; SEQ ID NO: 2) and placed under the control of a CMV promoter (SEQ ID NO: 3). Helices 1 through 8 of the EF domains from *Homo sapiens* RXRβ ("HsRXRβ-EF"; nucleotides 1-465 of SEQ ID NO: 4) and helices 9 through 12 of the EF domains of *Locusta migratoria* Ultraspiracle Protein ("LmUSP-EF"; nucleotides 403-630 of SEQ ID NO: 5) were fused to the transactivation domain from VP16 ("VP16AD"; SEQ ID NO: 6) and placed under the control of an SV40e promoter (SEQ ID NO: 7). Five consensus GAL4 response element binding sites ("5XGAL4RE"; comprising 5 copies of a GAL4RE comprising SEQ ID NO: 8) were fused to a synthetic TATA minimal promoter (SEQ ID NO: 9) and placed upstream of the luciferase reporter gene (SEQ ID NO: 10).

3.2—GAL4/mutantCfEcR-DEF/VP16-βRXREF-LmUSPEF:

This construct was prepared in the same way as in switch 3.1 above except wild-type CfEcR-DEF was replaced with mutant CfEcR-DEF comprising a ligand binding domain comprising a substitution mutation selected from Table 5.

3.3—GAL4/AaEcR-DEF/VP16-βRXREF-LmUSPEF:

This construct was prepared in the same way as in switch 3.1 above, except wild-type CfEcR-DEF was replaced with the wild-type DEF domains of mosquito *Aedes aegypti* EcR ("AaECR-DEF"; SEQ ID NO: 11).

3.4—GAL4/AmaEcR-DEF/VP16-βRXREF-LmUSPEF:

This construct was prepared in the same way as in switch 3.1 above, except the wild-type CfEcR-DEF was replaced with the wild-type DEF domains of ixodid tick *Amblyomma americanum* EcR ("AmaEcR-DEF"; SEQ ID NO: 12).

3.5—GAL4/BaEcR-DEF/VP16-βRXREF-LmUSPEF:

This construct was prepared in the same way as in switch 3.1 above, except the wild-type CfEcR-DEF was replaced with the wild-type DEF domains of white fly *Bamecia argentifoli* EcR ("BaEcR-DEF"; SEQ ID NO: 13).

3.6—GAL4/DmEcR-DEF/VP16-βRXREF-LmUSPEF:

This construct was prepared in the same way as in switch 3.1 above, except the wild-type CfEcR-DEF was replaced with the wild-type DEF domains of fruit fly *Drosophila melanogaster* EcR ("DmEcR-DEF"; SEQ ID NO: 14).

3.7—GAL4/MsEcR-CDEF/VP16-βRXREF-LmUSPEF:

This construct was prepared in the same way as in switch 3.1 above, except the wild-type CfEcR-DEF was replaced with the wild-type CDEF domains of Tobacco hornworm *Manduca sexta* EcR ("MsEcR-DEF"; SEQ ID NO: 15).

3.8—GAL4/NcEcR-DEF/VP16-βRXREF:

This construct was prepared in the same way as in switch 3.1 above, except the wild-type CfEcR-DEF was replaced with the wild-type DEF domains of green leafhopper *Nephotetix cincticeps* EcR ("NcEcR-DEF"; SEQ ID NO: 16) and βRXREF-LmUSPEF was replaced with *Mus musculus* RXRβ (SEQ ID NO: 18).

3.9—GAL4/TmEcR-DEF/VP16-βRXREF:

This construct was prepared in the same way as in switch 3.1 above, except the wild-type CfEcR-DEF was replaced with the wild-type DEF domains of yellow meal worm *Tenebrio molitor* EcR ("TmEcR-DEF"; SEQ ID NO: 17) and βRXREF-LmUSPEF was replaced with *Mus musculus* RXRβ (SEQ ID NO: 18).

TABLE 5

Substitution Mutants of *Choristoneura fumiferana* Ecdysteroid Receptor ("CfEcR") Ligand Binding Domain (LBD).

| CfEcR-DEF LBD Mutation | Resulting "WT to Mutant" Amino Acid Substitution | Corresponding amino acid in full length CfEcR (SEQ ID NO: 19) |
|---|---|---|
| V96T | Valine (V) to Threonine (T) | 379 |
| V107I | Valine (V) to Isoleucine (I) | 390 |
| N119F | Asparagine (N) to Phenylalanine (F) | 402 |
| Y127E | Tyrosine (Y) to Glutamic Acid (E) | 410 |
| V96T and N119F double mutant | Valine (V) to Threonine (T) and Asparagine (N) to Phenylalanine (F), respectively | 379 and 402, respectively |
| V390I and Y410E] | Valine (V) to Isoleucine (I) and Tyrosine (Y) to Glutamic Acid (E), respectively | 390 and 410, respectively |
| triple mutant | Glutamic acid (E) to Valine (V), Valine (V) to Isoleucine (I) and Tyrosine (Y) to Glutamic Acid (E), respectively | 274, 390 and 410, respectively |

In an effort to modify EcR ligand binding, residues within the EcR ligand binding domains that were predicted to be important for ligand binding based upon a molecular modeling analysis were mutated in EcRs from different classes of organisms. Table 5 indicates the amino acid residues within the ligand binding domain of CfEcR (Lepidopteran EcR) that were mutated and examined for modification of steroid and non-steroid binding.

Each one of the amino acid substitution mutations listed in Table 5 was constructed in an EcR cDNA by PCR mediated site-directed mutagenesis. Amino acid V96 of CfEcR was mutated to threonine, amino acid V107 of CfEcR was mutated to isoleucine, amino acid N119 of CfEcR was mutated to phenylalanine and amino acid Y127 of CfEcR was mutated to glutamic acid. Point mutants of CfEcRs were also made: one comprising the V96T and N119F substitutions (V96T+N119F), and a second comprising the V107I and Y127E substitutions (V107I+Y127E).

PCR site-directed mutagenesis was performed using the Quikchange site-directed mutagenesis kit (Stratagene, La Jolla, Calif.) using the reaction conditions and cycling parameters as follows. PCR site-directed mutagenesis was performed using 1× reaction buffer (supplied by manufacturer), 50 ng of dsDNA template, 125 ng of forward primer (FP), 125 ng of reverse complementary primer (RCP), and 1 μL of dNTP mix (supplied by manufacturer) in a final reaction volume of 50 μL. The forward primer and reverse complementary primer used to produce each EcR mutant are presented in Table 6. The cycling parameters used consisted of one cycle of denaturing at 95° C. for 30 seconds, followed by 16 cycles of denaturating at 95° C. for 30 seconds, annealing at 55° C. for 1 minute, and extending at 68° C. for 22 minutes.

TABLE 6

PCR Primers for Substitution Mutant CfEcR Ligand Binding Domain Construction.

| MUTANT | PRIMER (SEQ ID NO:) | PRIMER NUCLEOTIDE SEQUENCE (5' TO 3') |
|---|---|---|
| N119n | RANDOM FP (SEQ ID NO: 20) | gcgtacactcgcgacnnntacc gcaaggctggcatgg |
| N119n | RANDOM RCP (SEQ ID NO: 21) | ccatgccagccttgcggtannn gtcgcgagtgtacgc |
| V96T | FP (SEQ ID NO: 22) | ggtaatgatgctccgaaccgcg cgacgatacg |
| V96T | RCP (SEQ ID NO: 23) | cgtatcgtcgcgcggttcggag catcattacc |
| V107I | FP (SEQ ID NO: 24) | gcggcctcagacagtattctgt tcgcgaac |
| V107I | RP (SEQ ID NO: 25) | gttcgcgaacagaatactgtct gaggccgc |
| Y127E | FP (SEQ ID NO: 26) | caaggctggcatggccgaggtc atcgagg |
| Y127E | RP (SEQ ID NO: 27) | cctcgatgacctcggccatgcc agcccttg |

The resulting PCR nucleic acid products encoding the mutant EcR ligand binding domains were then each fused to a GAL4 DNA binding domain as described in Example 3.2 above. The GAL4/mutant EcR receptor constructs were tested for activity by transfecting them into NIH3T3 cells along with VP16-heterodimer partner in the presence of various ligands of the invention.

BIOLOGICAL ASSAYS

To determine if any of the compounds of the present invention can act as inducers of reporter gene activity in mammalian transactivation assays, these compounds were tested in NIH3T3 cells transfected with pFRLUC reporter and gene expression cassettes, 3.1 to 3.9 described in Example 3. The transected cells were grown in the presence of 0.01-33 µM concentrations of compounds. At 48 hr after addition of ligand, the cells were harvested and reporter activity was assayed using Dual Luciferase assay kit (Promega Corporation). Total relative light units (RLU) are shown. Standard methods for culture and maintenance of the cells were followed.

The steroidal ligands 20-hydroxyecdysone (20E) and ponasterone A were purchased from Sigma Chemical Company and Invitrogen. All ligands were dissolved in DMSO.

DNAs were transfected into mouse NIH3T3 cells (ATCC) as follows. Standard methods for culture and maintenance of the cells were followed. Cells were harvested and plated into 96-well plates at 2,500 cells per well, in 50 µL of growth medium containing 10% fetal bovine serum (FBS). Twenty-four hours later, the cells were treated with 35 µL of serum-free growth medium containing either dimethylsulfoxide (DMSO; control) or a DMSO solution of ligand at eight doses from 0.01-33 µM. The cells were then transfected using Superfect™ (Qiagen Inc.) transfection reagent. For each well, 0.625 µL of Superfect™ was mixed with 14.2 µL of serum-free growth medium. 0.16 µg of reporter construct and 0.04 µg of each receptor construct were added to the transfection reagent mix. The contents of the transfection mix were mixed in a vortex mixer and let stand at room temperature for 30 minutes. At the end of incubation, 15 µL of transfection mix was added to the cells. The cells were maintained at 37° C. and 5% $CO_2$ for 48 hours in 5% FBS.

Reporter Assay.

Luciferase activity was measured 48 hours after treatment using Bright-Glo™ luciferase assay system from Promega Corporation following the manufacturer's instructions. Relative Max Fold Induction (Rel Max FI) was determined as the maximum fold induction of the tested ligand observed at any concentration relative to the maximum fold induction of ponasterone A (PoA) and 20-hydroxyecdysone (20E) observed at any concentration. $EC_{50}$ values were calculated from dose response data using a three-parameter logistic model. Results of the assays are shown in Table 7.

TABLE 7

Relative fold induction of reporter gene (rel. max FI) is expressed in reference to 20-hydroxyecdysone (20E), ponasterone A (PoA), or 3,5-dimethyl-benzoic acid N-tert-butyl-N'-(2-ethyl-3-methoxy-benzoyl)-hydrazide.

| | | AA | AMA | BA | CF | CF-N119F/ V96T | E274V/ V390I/Y410E | DM | MS | NC | TM |
|---|---|---|---|---|---|---|---|---|---|---|---|
| 20E-2-methyl ether | $EC_{50}$ (µM) | ~10 | ~10 | >33 | >33 | >33 | >33 | >33 | ~20 | ~8 | >33 |
| | rel max FI (20E) | 0.87 | 0.65 | 0.03 | 0.14 | 0.02 | 0.01 | 0.00 | 0.16 | 0.82 | 0.07 |
| | rel max FI (PoA) | 0.30 | 0.50 | 0.03 | 0.00 | 0.00 | 0.00 | 0.00 | 0.10 | 0.84 | 0.04 |
| 20E-3-methyl ether | $EC_{50}$ (µM) | ~10 | ~3.3 | ~15 | >33 | ~10 | ~20 | >33 | ~10 | 1.69 | ~10 |
| | rel max FI (20E) | 1.75 | 0.91 | 0.29 | 1.15 | 1.54 | 2.56 | 0.02 | 1.15 | 1.01 | 1.14 |
| | rel max FI (PoA) | 0.60 | 0.70 | 0.23 | 0.01 | 0.35 | 0.25 | 0.03 | 0.73 | 1.04 | 0.59 |

TABLE 7-continued

Relative fold induction of reporter gene (rel. max FI) is expressed in reference to 20-hydroxyecdysone (20E), ponasterone A (PoA), or 3,5-dimethyl-benzoic acid N-tert-butyl-N'-(2-ethyl-3-methoxy-benzoyl)-hydrazide.

| | | AA | AMA | BA | CF | CF-N119F/ V96T | E274V/ V390I/Y410E | DM | MS | NC | TM |
|---|---|---|---|---|---|---|---|---|---|---|---|
| 20E-22-methyl ether | $EC_{50}$ (μM) | 1.04 | ~1 | ~3 | >33 | ~12 | >33 | ~4 | ~10 | 2.59 | 7.08 |
| | rel max FI (20E) | 2.52 | 1.08 | 1.54 | 0.07 | 0.53 | 0.34 | 0.87 | 1.29 | 1.02 | 1.58 |
| | rel max FI (PoA) | 0.86 | 0.83 | 1.23 | 0.00 | 0.12 | 0.03 | 1.07 | 0.81 | 1.05 | 0.81 |
| 20E-2,22-dimethyl ether | $EC_{50}$ (μM) | ~8 | ~8 | ~10 | >33 | >33 | >33 | ~20 | ~20 | ~10 | ~10 |
| | rel max FI (20E) | 2.34 | 0.94 | 0.24 | 0.63 | 0.01 | 0.02 | 0.12 | 0.15 | 0.84 | 0.24 |
| | rel max FI (PoA) | 0.80 | 0.72 | 0.19 | 0.00 | 0.00 | 0.00 | 0.15 | 0.09 | 0.86 | 0.13 |
| 20E-3,22-dimethyl ether | $EC_{50}$ (μM) | 7.15 | ~2 | ~10 | >33 | >20 | >33 | ~20 | ~10 | ~8 | ~6 |
| | rel max FI (20E) | 2.32 | 1.04 | 0.38 | 0.46 | 0.27 | 0.06 | 0.07 | 0.82 | 1.03 | 1.37 |
| | rel max FI (PoA) | 0.79 | 0.80 | 0.30 | 0.00 | 0.06 | 0.01 | 0.09 | 0.52 | 1.06 | 0.71 |
| 20E-2,3,14,22-tetramethyl ether | $EC_{50}$ (μM) | >33 | >33 | >33 | >33 | >33 | >33 | >33 | >33 | >33 | >33 |
| | rel max FI (20E) | 0.07 | 0.34 | 0.02 | 0.46 | 0.00 | 0.01 | 0.01 | 0.00 | 0.01 | 0.05 |
| | rel max FI (PoA) | 0.02 | 0.26 | 0.01 | 0.00 | 0.00 | 0.00 | 0.02 | 0.00 | 0.01 | 0.02 |
| 20E-22-ethyl ether | $EC_{50}$ (μM) | | | | 4.85 | | 0.76 | | | | |
| | rel max FI (diacyl-hydrazine) | | | | 0.77 | | 1.1 | | | | |
| 20E-22-n-propyl ether | $EC_{50}$ (μM) | | | | >33 | | ~12 | | | | |
| | rel max FI (diacyl-hydrazine) | | | | 0.005 | | 0.49 | | | | |
| PoA-22-methyl ether | $EC_{50}$ (μM) | <0.01 | | | ~2 | | <1 | ~0.03 | | | |
| | rel max FI (diacyl-hydrazine) | ~0.8 | | | 0.3-0.65 | | ~0.6 | ~0.9 | | | |
| 20E-25-methyl ether | $EC_{50}$ (μM) | | | | >33 | | ~12 | | | | |
| | rel max FI (diacyl-hydrazine) | | | | 0.0013 | | 0.24 | | | | |

CF = *Choristoneura fumiferana* (Cf) EcR
AA = *Aedes aegypti* (Aa) EcR
AMA = *Amblyomma americanum* (Ama) EcR
BA = *Bamecia argentifoli* (Ba) EcR
DM = *Drosophila melanogaster* (Dm) EcR
MS = *Manduca sexta* (Ms) EcR
NC = *Nephotetix cincticeps* (Nc) EcR
TM = *Tenebrio molitor* (Tm) EcR

EXAMPLE ONE

Disclosed are semi-synthetic steroid modulators of gene-switches. Representative ecdysteroids 20-hydroxyecdysone (20E) and ponasterone A (PoA) were singly- and multiply-methylated at the 2-, 3-, 14-, 22- and 25-positions, or singly-alkylated at the 22 position. The semi-synthetic steroids were assayed in both a natural insect system (*Drosophila* $B_{II}$ cells) and engineered gene-switch systems in mammalian cells using *Drosophila melanogaster*, *Choristoneura fumiferana* and *Aedes aegypti* EcRs and/or mutants thereof. Gene-switch potency is maintained or enhanced for 20E and PoA methylated at the 22 position. The SAR of the alkylated steroids indicates that the 22-OH is an H-bond acceptor, 25-OH is likely an H-bond donor, and 2-OH and 3-OH are donors and/or acceptors with each other and with EcR. Overall, calculated ADME properties using the membrane-interaction (MI)-QSAR methodology indicate desirable trends toward lower solubility, higher permeability, and higher blood-brain barrier penetration without excessive modulation of log P or plasma protein binding. Alkylation demonstrates improved steroidal activators for gene therapy application of gene switch technology.

Ligand-inducible gene expression systems, such as EcR-based systems, are well-suited for gene therapy applications. Due to the ability to control protein expression level, the incorporation of gene switches into gene therapeutic regimens offers more effective indications in cancer, cardiovascular diseases, diabetes, neurodegenerative disorders, motor neuron diseases, muscular dystrophy, cystic fibrosis, neuropathic pain, rheumatoid arthritis and regenerative medicine in general. Additionally, gene switches have diagnostic, biopharmaceutical, and other applications in areas such as cell-based assays and animal models for developmental drug testing, as well as biotherapeutics and biomaterials production. The insect ecdysteroid-regulated gene switches are refractory to human endogenous steroids, and show very low basal transgene expression, high inducibility, and broad dose-response.

Steroid hydroxyl groups, individually and severally were methylated or otherwise alkylated. Thereby, 23 new semi-synthetic steroids were synthesized, purified and assigned structurally. Alkylation positions were chosen to maximize interactions with the EcR. The resulting steroids were assayed in cellular gene-switch systems. Other advantageous properties include potential increased membrane permeability and resistance to metabolism. MI-QSAR ADME calculations of the new steroids in comparison with their non-alkylated counterparts were performed. CoMFA/CoMSIA modeling of these steroids studied by multi-dimensional QSAR in combination with ca. 150 previously known steroids assayed in a natural *Drosophila* $B_{II}$ cell system was also performed. The new semi-synthetic steroids are useful as gene-switch activators for clinical gene therapy.

Synthesis—Materials and Methods.

PoA was supplied by René Lafont, Université Pierre et Marie Curie, Paris. 20E was supplied by Dr. V. Volodin, Institute of Biology, Russian Academy of Sciences, Syktyvkar, Russia. For solubility and logD measurements, PoA was purchased from Axxora/Alexis Corp. while 20E and muristerone A were obtained from Sigma-Aldrich Inc. Other reagents and solvents were purchased from Fisher Scientific and Sigma-Aldrich; deuterated solvents for NMR analysis were purchased from Goss Scientific Instruments Ltd (Great Baddow, U.K.). Dry acetone and $CH_2Cl_2$ were distilled before use. Water for HPLC was deionized to a degree of purity of 17 ohms. All other HPLC solvents were degassed immediately prior to use by filtration under suction through 0.45 µm (for aqueous solutions) or 0.5 µm (for organic solutions) Waters Millipore® filters. Anhydrous reaction conditions were achieved by flame-drying Schlenk reaction tubes under vacuum and introduction of a nitrogen or argon atmosphere before the reagents. Cannulae were used to transfer liquids. Steroids were freeze-dried before use. Silver oxide reactions were protected from light with an aluminum foil covering.

Reactions were monitored by HPLC interfaced with a diode-array detector (DAD) on a Gilson 170 system (Anachem Limited, Luton, U.K.), using a Sphereclone ODS2 column (5 µm, 150×4.60 mm; Phenomenex, Macclesfield, U.K.), subjected to a linear gradient from 30% to 100% methanol in water over 25 min, followed by 10 min at isocratic 100% methanol, at a flow-rate of 1 mL/min. Chromatographic monitoring was at wave-lengths (λ) of 242 nm and 300 nm. Equal volumes of reaction mixture were taken out at regular time intervals, the samples quenched with methanol, centrifuged and the supernatants filtered through a Minisart® 0.20 mm filter (Sartorius, Epsom, U.K.). The filtrates were concentrated under reduced pressure, made up to 30% methanol in water (v/v) to the minimum volume required for dissolution, and injected.

Separation of individual steroid ethers in the crude reaction mixtures was carried out by development of suitable HPLC systems, which involved one or more of the following methods. (A) semi-preparative $C_{18}$-HPLC (Phenomenex Sphereclone ODS2; 250×10 mm, 5 µm) at a flow-rate of 2 mL/min; (B) preparative $C_{18}$-HPLC (Phenomenex Sphereclone ODS2; 250×21.20 mm, 5 µm, flow-rate=5 mL/min). ($C_1/C_2$) semi-preparative silica column (Kinesis Zorbax Sil; 250×9.4 mm, 5 µm, flow-rate=2 mL/min), eluted isocratically with $CH_2Cl_2$:2-PrOH:$H_2O$ 160:30:1.5 ($C_1$-) or 125:30:2.0 ($C_2$), v/v/v.

Compound purity was HPLC-verified using two different reversed-phase columns (Phenomenex Sphereclone $C_{18}$ and $C_6$, 5 µm, 150×4.60 mm) and one normal-phase column (Kinesis-GRACE Apex II Diol, 5 µm, 150×4.60 mm), and is expressed as % total peak area at λ=242 nm, for all compounds except 22, ($\lambda_{max}$=299 nm), for which λ=300 nm was used.

Product quantification was carried out by UV spectroscopy on a Shimadzu UV-2401PC (Shimadzu GB, Milton Keynes, U.K.) for compounds containing either the 14α-hydroxy-7-en-6-one moiety ($\lambda_{max}$=242 nm, molar extinction coefficient [ε]=12,400 $Lmol^{-1}$ $cm^{-1}$) or the 14α-hydroxy-7,9(11)-dien-6-one moiety ($\lambda_{max}$=299 nm, ε=14,190 $Lmol^{-1}$ $cm^{-1}$). Concentrations were calculated according to the Lambert-Beer equation.

One-dimensional ($^1$H and $^{13}$C) and two-dimensional (1H-1H COSY, $^1$H-$^1$H NOESY, $^1$H-$^{13}$C HMQC and $^1$H-$^{13}$C HMBC) NMR spectra were recorded either on an automated Bruker ACF-300 spectrometer or on a Bruker AVANCE DRX-400 spectrometer. Samples were dissolved in methanol-$d_4$ containing tetramethylsilane (TMS) as an internal standard. $^{13}$C spectra were calibrated with the middle signal of the methanol heptet at 49.00 ppm. $^1$H and $^{13}$C chemical shifts (δ) are expressed in parts per million (ppm). Coupling constant (J) and width at half-height ($w_{1/2}$) values are reported in Hertz (Hz).

High-resolution mass spectroscopy was performed in either the chemical ionisation mode (CIMS) or the positive-ion Fast Atom Bombardment mode (FABMS). CIMS was recorded on a Micromass GCT spectrometer equipped with a direct inlet probe or on a Jeol 700 spectrometer equipped with a direct inlet probe, using in both cases $CH_4$ as reagent gas, methanol as solvent, source temperature of 200° C. and a probe temperature of 500-650° C. FABMS was also recorded on the Jeol 700 spectrometer, using Xe as reagent gas, source temperature at 30° C. and "Magic Bullet" (a 4:1 mixture of 1,4-dithio-L-threitol and 1,4-dithioerythreitol) as matrix.

Synthesis of Steroids with O-alkyl ether functionalities at the 2-OH, 3-OH, 14-OH and/or 22-OH.

Prior to etherification, the 2,3- and/or 20,22-diol groups of the starting ecdysteroid were selectively protected by transformation into the corresponding 20,22-phenylboronate, 2,3- acetonide or 2,3,20,22-diacetonide analogue (FIG. 1). Synthetic procedures for steroid ethers 1 and 2 follow as illustrative examples.

Synthesis of 20-hydroxyecdysone 2-methyl ether and 20-hydroxyecdysone 3-methyl ether.

$Ag_2O$ (116.0 mg, 10 eq) was added to a stirred solution of freshly prepared 20E 20,22-phenylboronate (25a; 30 mg, 53 µmol) in DMF (2 mL) at room temperature under anhydrous conditions. $CH_3I$ (258 µL, 44.7 eq) was added in four portions during the course of the reaction, and additional $Ag_2O$ (10 eq) was added after 4 h. The reaction was monitored by HPLC-DAD. After 7.5 h, ethyl acetate (25 mL) was added and the mixture was filtered through a Celite® (BDH Chemical Ltd., Poole, U.K.) pad over a sintered-glass filter funnel of porosity 4 (Weiss-Gallenkamp, U.K.). The filter was washed with additional ethyl acetate (150 mL) and the solvents evaporated in vacuo. The crude reaction mixture was pre-purified by solid-phase extraction using a Sep-Pak® Vac 35 cc $C_{18}$-10 g cartridge (Waters, Elstree, U.K.). The phenylboronate group was then removed by dissolving the products in a 9:1 (v/v) mixture of THF and $H_2O_2$ (100 volumes, pre-neutralised with NaOH 0.1 N) and stirring at room temperature and neutral pH for 2.5 h, followed by dilution with $H_2O$, evaporation of THF and solid-phase extraction. The crude products were purified by semi-preparative $C_{18}$-HPLC (Phenomenex Sphereclone ODS2, 250×10 mm, 5 µm, flow-rate=2 mL/min, at 242 nm) with isocratic 1:1 $CH_3OH/H_2O$, wherein 2 eluted after 20 min (6 mg, 25%; purity>99%) and 1 after 23 min (13 mg, 50%; purity>99%).

Synthesis of Steroids with a O-alkyl ether functionality at the 25-OH: 20-hydroxyecdysone 25-methyl ether and 22,25-dimethyl ether.

DTBMP (88.8 mg, 6 eq) and methyl triflate (47 µL, 6 eq) were added to a solution of 20E 2,3-acetonide (25b; 37.5 mg, 72.1 µmol) in dry $CH_2Cl_2$ (3 mL). The mixture was stirred at room temperature under anhydrous conditions. After 55 h, the methyl triflate was removed under vacuum and the residue was treated with a 1:1 (v/v) mixture of 0.1 M HCl and 1,4-dioxane. The methylated steroids were purified by preparative $C_{18}$-HPLC (Phenomenex Sphereclone ODS2, 250×21.20 mm, 5 µm, flow-rate=5 mL/min) using isocratic 60% $CH_3OH/H_2O$. Yield: 11.15 mg (31%; purity>99%) 10 and 5.63 mg (15%; purity>99%) 14.

Cellular gene-switch assays—Drosophila $B_{II}$ cell morphology.

The *D. melanogaster* $B_{II}$ cell line bioassay was used to test the activity of EcR ligands. Assays were performed in quadruplicate. In brief, stock solutions ($10^{-3}$ M to $10^{-1}$ M) in MeOH were prepared for each of the test compounds. Aliquots (20 µL) of each dilution were transferred to wells of a microtitre plate and solvent was evaporated. Cell suspension (200 µL) at approximately $2 \times 10^5$ cells/mL medium was added to each well and the covered plate was incubated in a humid environment at 25° C. for 7 days. Cellular response is measured turbidometrically (405 nm) as a function of steroid concentration.

Cellular Gene-Switch Assays—Engineered EcR:USP/RXR Systems.

Cellular gene-switch assays were performed by transfecting the following constructs in mouse embryonic fibroblast cells (NIH3T3). The wild-type D-, E- and F-domains from (a) *Choristoneura fumiferana* EcR (CfEcR-DEF), (b) Choristoneura fumiferana EcR with a E274V/V390I/Y410E mutation in the E-domain, (c) *Aedes aegypti* EcR (AaEcR-DEF), and (d) *Drosophila melanogaster* EcR (DmEcR-DEF) were fused to a GAL4-DBD and placed under the control of the CMV promoter. A chimeric RXR from *Homo sapiens* RXRβ and *Locusta migratoria* RXR was fused to VP16-AD and placed under the control of an SV40e. The inducible luciferase reporter plasmid, pFRLuc, (Stratagene Cloning Systems, La Jolla, Calif., USA) contains five copies of the GAL4 response element and a synthetic minimal promoter. The VgEcR/RXR gene switch system, which employs a hybrid EcR bearing a VP16 activation domain and a 3-residue mutated DBD that recognizes an asymmetric EcR- and glucocorticoid receptor response element, was obtained from Invitrogen Inc. (Carlsbad, Calif., USA), and employed in an analogous manner by transient transfection in NIH3T3 cells using a luciferase reporter-containing vector.

NIH3T3 cells were maintained at 37° C. and 5% $CO_2$ in Dulbecco's modified Eagle's medium (DMEM) supplemented with 10% Bovine Calf Serum, both obtained from Mediatech, Inc., Manassas, Va. Cells were plated in a 96-well plate at a density of 2,500 cells/well in 50 µL of growth medium. The following day cells were first treated with 35 µL of serum-free DMEM containing dimethyl sulfoxide (DMSO; control) or a DMSO solution containing ligand. Cells were then transfected with 15 µl of serum-free DMEM containing 0.04 µg of EcR construct, 0.04 µg of RXR construct, and 0.16 µg of luciferase reporter construct per well, using SuperFect transfection reagent (Qiagen Inc., Valencia, Calif., USA) according to the manufacturer's instructions. Ligands were tested at 8 doses from 0.01-33 µM and the final DMSO concentration was 0.33% in both control and treatment wells. After a 48 hour post-treatment and transfection incubation, the cells were assayed for luciferase activity using the Bright-Glo™ Luciferase Assay System (Promega Corporation, Madison, Wis., USA) following the manufacturer's instructions. 3D-QSAR Training Set and Test Set. A library of ecdysteroids and associated $B_{II}$ activity values were used to generate or validate a 3D-QSAR model. Fifteen O-alkylated steroids (1-7, 9-15 and 18) were included in the analysis, while the other compounds were either isolated from plants, purchased, or generously provided by other researchers. A purity requirement of at least 97% was set for all compounds subjected to activity tests. Tested steroid ethers were at least 98% pure. A check for accuracy was carried out for of both structure and activity data in the QSAR library.

Twenty steroids were partitioned from the 3D-QSAR training set to generate an independent test set for external validation of the model. Test set selection was carried out using the 4DQSAR-MS methodology, which computes chemical similarity scores on the basis of the 4D-fingerprint molecular similarity matrix.

Molecular Modeling and 3D-QSAR Analysis.

Molecular modeling, comparative molecular field analysis (COMFA) and comparative molecular similarity index analysis (COMSIA) were performed using SYBYL 7.0. The reported crystal structure of PoA bound to *H. Virescens* (Hv) EcR (PDB code=1R1K) was used as a molecular template for conformational selection for the QSAR molecular set. Molecules requiring arbitrary conformational decisions were individually superimposed to PoA in complex with HvEcR and query substituents on the steroid scaffold were manually adjusted to maximize steric acceptability in the ligand-binding pocket. The resulting 3D-models of the compounds were energy-minimized using the standard Tripos Force Field with Gasteiger-Hückel charges, aligned by the 17-carbon steroid cores and positioned at the center of the SYBYL coordinate lattice. Partial atomic charges were assigned using the semi-empirical MNDO method (ESP fit) computed in SYBYL via the MOPAC interface.

For CoMFA, Tripos standard steric and electrostatic, and indicator steric, electrostatic and hydrogen bond fields were calculated; for CoMSIA, steric, electrostatic, hydrophobic, H-bond donor and H-bond acceptor similarity indices were derived, using SYBYL default parameters, a 2 Å spaced grid and an $sp^3$ $C^{+1}$ probe. Partial least squares (PLS) or sample-distance partial least squares (SAMPLS) analyses with leave-one-out (LOO) cross-validation were used to find a relationship between CoMFA/CoMSIA field descriptors and $B_{II}$ activities of the compounds. A minimum sigma (column filtering) of 0.5 kcal/mol was applied to improve the signal-to-noise ratio. Statistical significance of the resulting models was judged jointly by the LOO cross-validation correlation coefficient, $q^2$, and the standard error of prediction, $S_{PRESS}$. Final model was generated by non-cross-validated conventional PLS analysis derived using the optimum number of components of the corresponding LOO cross-validation analysis, after removal of seven compounds from the initial pool of steroids (training set=140 compounds). Model validation involved the prediction of $B_{II}$ activity values for the test set and comparison to the observed values.

ADME Properties.

The octanol-water partition coefficients (M log P) of steroid O-alkyl ether analogues were determined by scaling against previously calculated M log P values of non-ether steroids. Caco-2 cell permeation coefficients and the blood-brain barrier partition coefficients were made using established membrane-interaction QSAR (MI-QSAR) models. MI-QSAR analysis includes, in the descriptor pool used in the development of a QSAR model, properties and features explicitly derived from the simulation of the transport of each of the solutes (small organic compounds) comprising the training set through a model membrane assembly composed of phospholipids, in this case dimyristoylphosphatidylcholine (DMPC) molecules. Estimates of steroid binding to human serum albumin (HSA) were obtained using 3D-FEFF-QSAR analysis. This approach calculates the free energy, $\Delta G$, of the binding of an steroid ligand to HSA using a scaled QSAR model as a scoring function. Ka values were derived using $\Delta G=RT \ln (Ka)$. $Ka=(1/Kb)$, where Kb is the molecule's binding affinity to HSA, under the assumption that binding occurs exclusively to HSA, a binary complex is formed, and an excess of HSA ([HSA]=0.6 mM) is present as compared to the concentration of the ligand. Aqueous solubility of the steroid O-alkyl ether analogues were determined using the AMSOL method and software.

Physicochemical Measurements.

Log D was measured by Absorption Systems, Inc. Ponasterone A and 20E were measured at 100 µM in equal volumes of pH 7.4 buffer and water-saturated octanol in a 1.5 mL shake flask system in duplicate using testosterone standard. Each shake flask was agitated for 60 minutes at room temperature, then allowed to stand for 1 hour at room temperature. Serial dilutions of the organic and aqueous layers were prepared and concentrations of test compound at each dilution were determined using a generic LC/MS/MS method with a minimum 4 point calibration curve. Water solubility was measured by Robertson-Microlit, Inc. Samples of saturated solutions of PoA, 20E, muristerone A, and diacylhydrazine were dissolved in HPLC grade water, stirred at 25° C. for 1, 5, and 10 days, and then filtered using 0.45 micron filter to obtain a clear solution. For each substance, UV absorbance was measured at the maxima of 249, 248, 239 nm, and 219 nm, respectively, diluting if necessary. Absorbance was compared to that of a reference standard at the same absorbance maximum for a 1-2% solution of the same steroid in $CH_3OH$, allowing for up to 10 nM maxima shift due to solvent effect.

Synthesis.

Twenty-three steroid O-alkyl ethers were synthesized FIG. 2), including derivatives of 20E (25), the most abundant insect molting hormone, PoA (26), one of the most potent natural ecdysteroid, and dachryhainansterone (27), a moderately strong agonist with an unusual core structure. The derivatives of 20E are five monomethyl ethers at the 2-, 3-, 14-, 22- or 25-OH (1-4, 10), four dimethyl ethers at the 22-OH and one each of 2-, 3-, 14-, and 25-OH (11-14), and one tetramethyl ether (15). PoA derivatives include three mono-O-methyl ethers at the 2-, 14- or 22-OH (16-18), and three analogues with a double ether functionality (19-21). Beside methyl ethers, several 20E 22-O-ether analogues were prepared, including compounds with O-n-alkyl groups up to a four-carbon chain (5, 6 and 8) and the allyl (7), benzyl (8) and 2'-ethyloxiranyl (23) ether groups. Selective introduction of a methyl group on individual hydroxyl positions was obtained using the protection/deprotection strategy depicted in FIG. 1, which involves the transformation of the 2,3-cis- and/or 20,22-diol groups into acetonide or phenylboronate groups. Simultaneous preparation of singly- and multiply-methylated analogues (16, 17, 19, 20) was achieved by a one-pot reaction approach starting with the unprotected ecdysteroid. This method is advantageous in terms of reaction times, but requires careful HPLC-driven reaction-monitoring and leads to a higher ratio of multiply vs. singly methylated analogues. In methylation reactions involving $Ag_2O$ and $CH_3I$, the reactivity sequence of ecdysteroid hydroxyl group is 22-OH>2-OH>3-OH>>14-OH. While methylation of the tertiary 25-OH of 20E was not observed using $Ag_2O/CH_3I$, the 14-OH could be converted into a $CH_3O$-group by increasing the reaction temperature (up to 60° C.) or the amount of the reagents. However, large excess or prolonged exposure to $Ag_2O$ led to product degradation, such as dehydration and/or chromophore alteration. As a case in point, formation of a methylated PoA derivative with an altered chromophore (7,9 (11)-dien-6-one group), DaH 22-methyl ether (22), was observed after a prolonged exposure (46 h) of PoA to $Ag_2O/CH_3I$ at room temperature. A tentative reaction mechanism could involve the elimination by $Ag_2O$ of one of the two 11-H atoms, followed by a double bond migration towards conjugation. In the search for alternative O-methylation methods suitable for chemically sensitive molecules such as ecdysteroids, we found that six equivalents each of methyl triflate and DTBMP at 25° C. under anhydrous conditions promote smoothly and selectively 25-OH methylation of 20E 2,3-acetonide (25b), with a reactivity sequence of 25-OH>22-OH>>14-OH. This approach represents a newly developed procedure for O-methylation of polyhydroxylated steroids. In all of our experiments, the 20-OH position remained refractory to methylation.

NMR.

The $^1H$ and $^{13}C$ spectral assignments of O-alkyl ecdysteroids 1-23 were made relative to those of the parent compound (20E, PoA or DaH) and by examination of J coupling connectivity in $^1H$-$^1H$ COSY, $^1H$-$^{13}C$ HMQC and $^1H$-$^{13}C$ HMBC spectra. The $^1H$ signals of secondary ether substituents at the 2-, 3- and/or 22-positions showed a characteristic upfield shift of ca. 0.4 ppm, and correlated to $^{13}C$ signals which are downfield shifted of ca. 10 ppm with respect to the parent ecdysteroids. Steroids bearing a 14α-$OCH_3$ group are easily recognizable from their $^1H$-NMR spectra, wherein the 9α-H signals show an upfield shift of ca. 0.3 ppm ($\delta_H$=2.76-2.78 ppm), and their $^{13}C$-NMR spectra, wherein the 14-C signals showed a downfield shift of ca. 6 ppm ($\delta_C$=90.95-90.98 ppm). The alpha-stereochemistry of the 14-O-methyl group was confirmed in NOESY experiments by irradiation of the 9α-H signal, leading to a 3% enhancement of the 14-OCH$_3$ signal (2.97 ppm) and 13% enhancement of the 2α-H signal (3.53-3.81 ppm). 20E 25-methyl ether analogues showed a downfield shift of ca. 5 ppm for the 25-C signals (76.16 ppm) with respect to 20E, and an upfield shift of ca. 4 ppm for the 26-C and 27-C signals (25.52 and 25.27 ppm). In the $^1$H-NMR spectra of ecdysteroid methyl ether analogues, singlets arising from the 2β-OCH$_3$, 3β-OCH$_3$, 14α-OCH$_3$, 22-OCH$_3$ and 25-OCH$_3$ appeared at 3.39, 3.40, 2.97, 3.50 and 3.19 ppm, respectively. In the $^1$H-NMR spectra of 20E 22-ethyl, propyl and butyl ether analogues, the two protons attached to the alpha carbon of 22-OR groups appeared as diastereotopic signals with δ$_H$ ranging from 3.51 to 3.75 ppm. In the $^1$H-NMR spectrum of 23, the two doublets at 3.49 ppm and 3.39 ppm ($^2$J=12 Hz), corresponding to a $^{13}$C signal at 63.54 ppm, were assigned to the geminal oxiranyl protons of the 22-ethyloxiranyl group; the quaternary $^{13}$C signal of the O—C—O group of 23 fell at 110.25 ppm. *Drosophila* B$_{II}$ cell assay (FIG. 3).

*D. melanogaster* B11 cells naturally express native EcR-USP complex and give a specific and quantitative response to EcR agonists and antagonists. O-alkyl steroids 1-23 exerted agonist potencies in the B$_{II}$ bioassay at concentrations ranging from 100 μM down to 1 nM, depending on the number and the position of the ether substituent in the molecule. In particular, methylation of the 2-, 3-, 14- and 25-hydroxyl groups of 20E reduces potency, but 20E 22-methyl ether (4) maintains 20E potency. The 22-ethyl ether analogue (5) is slightly less potent than methyl, while the activity difference increases with larger alkyl groups of propyl, allyl and butyl (6, 7, 8). However, a 22-O-benzyl substituent (9) does not decrease 20E potency very much. O-alkylation of PoA at any position decreases potency in the B$_{II}$ bioassay.

Engineered EcR/RXR: USP Gene-Switch.

Capacity of the O-alkyl steroids to actuate gene expression was examined in a mouse cell line transiently transfected with the components of the inducible system. Primarily two gene switch versions were used: one based on the wild-type spruce budworm (Cf) EcR (wt-CfEcR-DEF) and the other based on the E274V/V390I/Y410E mutant of this receptor (mutant-CfEcR-DEF). With some steroids, similar experiments were conducted with yellow fever mosquito (Aa) and fruit fly (Dm) EcRs in the same gene switch format. A chimera between human RXRβ and an insect USP from *Locusta migratoria* (LmUSP) was fused to VP16-AD and used as partner protein for the EcR.

Steroids were evaluated by both potency (EC$_{50}$) and efficacy. The latter, RMFI, is calculated as the maximum fold-induction of the test ligand relative to the maximum fold induction of a non-steroidal diacylhydrazine EcR agonist (30) at its optimal tested concentration under the same assay conditions. Fold induction of a test or reference ligand is defined as the ratio of gene expression induced by the ligand and gene expression of a DMSO control.

In the wt-CfEcR gene switch PoA (26) showed the highest inducing activity among the steroids tested (EC$_{50}$=0.19 μM, RMFI=~0.18), while muristerone A and polypodine B were less potent (EC$_{50}$=7.4 μM and ~12, respectively) and 20E was inactive (EC$_{50}$>33 μM). Potency of PoA was decreased by O-alkylation at any position, albeit PoA 22-methyl ether (18) and dacryhainansterone 22-methyl ether (22) provided higher fold-inductions (RMFI=~0.6 and ~0.3, respectively) than PoA itself (RMFI=~0.2). A particular 20E O-alkylated analogue, 20E 22-ethyl ether (5), induced the reporter gene by 77% of maximum fold induction at ca. 5 μM concentration.

In the E274V/V390I/Y410E mutant-CfEcR gene switch, PoA and PoA 22-methyl ether are the best performing steroids (FIG. 4): EC$_{50}$ values were 0.1 μM for PoA and 0.7 μM for PoA 22-methyl ether, with RMFI values of 0.52 and 0.58, respectively. In this switch, muristerone A is relatively weak with an EC$_{50}$ of 1 μM; likewise polypodine B at ~7 μM. 20E was a very poor actuator (EC$_{50}$=20 μM). However, 20E potency was substantially improved by 22-ethylation, both in terms of EC$_{50}$ (0.76 μM for 5; ~20 μM for 20E) and RMFI (1.1 for 5; 0.12 for 20E). Although more modestly, 20E 22-n-propyl (6), 22-butyl (8), 22-benzyl (9) and 25-methyl (10) ethers also enhanced the performance of their parent compound, while 20E 22-allyl ether (7) gave the same activity as 20E. Thus, in both the wt and E274V/V390I/Y410E mutant formats of the CfEcR gene switch, PoA 22-methyl ether is the strongest O-alkyl ether and 20E 22-ethyl ether is a close runner-up.

Some O-alkylated steroids were further tested in gene-switches of the same general format, where, in addition to E274V/V390I/Y410E mutant-CfEcR and VgEcR/RXR, wild-type AaEcR or the wild-type DmEcR were substituted for CfEcR. Potency of PoA 22-methyl ether is higher than muristerone A, and is somewhat more potent than PoA in both the AaEcR- and DmEcR-based assays (EC$_{50}$=0.38 nM and 66 nM, respectively). The AaEcR system is more sensitive than CfEcR to both PoA 22-methyl ether and the tested standards PoA (1.1 nM) and muristerone A (9 nM) in terms of potency, but is less sensitive in terms of efficacy (for example, PoA: FI=166 at 1 μM [AaEcR] cf. ~900 at 1 μM [CfEcR]). Most of the difference is simply due to higher background levels in the "off" state in the AaEcR switch (FI=7.6 [AaEcR] cf. 0.7 [CfEcR]), rather than a lower absolute expression of the reporter gene (RLUs=~1046 [AaEcR] cf. 540 [CfEcR]). Relative to the AaEcR switch, the DmECR switch is more like the CfEcR switch in terms of background transcription, and is less responsive in the sense of efficacy. In 3T3 cells, the previously developed VgEcR/RXR switch format was induced by PoA and muristerone A at EC$_{50}$=0.641 and 0.851 μM, respectively, and by PoA 22-methyl ether at EC$_{50}$=0.553 μM. In comparison, the AaEcR- and DmEcR-based switches are responsive to these ligands at low (AaEcR) and mid (DmEcR) nanomolar concentrations, indicating a substantial potency improvement.

Final 3D-QSAR model. A diverse combination of molecular fields, including CoMFA steric and electrostatic fields, CoMSIA H-bond donor, H-bond acceptor and hydrophobic fields, as well as polar surface area (PSA) were chosen to best represent the ecdysteroid library. The statistics of the resulting 3D-QSAR model are summarized in FIG. 5.

Steroids and the EcR Gene Switch in Gene Therapeutics.

Use of the EcR gene switch has been demonstrated both in cell and tissue culture as well as animal models. The most potent ligands are represented by primarily two chemotypes: the synthetic diacylhydrazines and the natural, usually plant-derived, steroids. Representatives from both groups have been used successfully with the EcR gene switch in model studies. From the perspective of bioavailability, the diacylhydrazines have class II-type ADME characteristics (low solubility, high log P, high permeability) with few easily-metabolizable loci, while the ecdysteroids are more highly soluble, with lower log P and many hydroxyl groups which can be readily metabolized or conjugated.

Synthesis.

Twenty-three O-alkyl ecdysteroid analogues of 20E, PoA and DaH were synthesized. All mono-methyl ethers of 20E and PoA were obtained, with the exception of (a) the 3-methyl ether of PoA, obtained only together with 22-methylation, and (b) the 20-methyl ethers, since the 20-hydroxyl proved unreactive. The general synthesis relies on well-established ketal and borate diol protection strategies on the 2,3- and 20,22-diol groups respectively. Synthesis of 20E 22-methyl (4) and 22-ethyl (5) ethers and isolation of 20E 25-methyl ether (polypodoaurein, 10 from the fern *Polypodium aureum* L.) had been described before this study, but none of these had been subjected to gene-switch assays.

Cellular Gene-Switch Assays.

To test the gene-switch potency of ethers 1-23, two gene switch formats were used, and a third was briefly investigated with several ligands. The first was a natural *D. melanogaster* $B_{II}$ cell line. The $B_{II}$ cell-line is derived from hemocytes of a tumorous blood cell mutant (l[2]mbn). Addition of steroids to $B_{II}$ cells acts as a signal to induce phagocytosis, and the cells develop from an even layer of small cells to clumps of larger cells surrounded by clear areas. This response can be quantified turbidometrically.

The second gene-switch format is an engineered heterodimer pair. It utilizes an EcR ligand-binding domain linked to a bacterial GAL4 DNA binding-domain, which upon exposure to ligand, associates with a hybrid locust-human RXR linked to a viral VP16 activation domain. This complex in turn binds to the GAL4 response element upstream from a luciferase reporter gene, expression of which provides a fluorescene readout. The entire switch system is expressed transiently in murine 3T3 cells. EcR-LBD variants of this switch, in which the LBD sequences were derived from Choristoneura fumiferana (spruce budworm, CfEcR), *Aedes aegypti* (mosquito, AaEcR), and *Drosophila melanogaster* (fruit fly, DmEcR) were utilized (FIG. 8). Additionally, a mutant variant (E274V/V390I/Y410E) of CfEcR previously found to increase overall EcR ligand sensitivity, was tested. In each case, all other components of the assay system remained identical, except that a few steroids were tested in a different 3T3 cell line clone.

The third gene-switch format used for a few compounds is the DmEcR-derived VgEcR/RXR system previously used in murine studies in vivo.

Qualitative SAR of Steroids—22-O-Alkyl Ecdysteroids Retain or Improve the Inducing Activity Of Their Parent Compounds.

Steroids were paired according to the presence or absence of one or more methyl caps at given positions, and potency differences in the *Drosophila* $B_{II}$ assay were calculated (FIG. 6). The 20E and PoA ether derivatives with a single ether substitution (1-10, 16-18, 22-23) spanning the 2-, 3-, 14-, 22- and 25-positions permit direct derivation of a relationship between potency differences and capping of a particular OH-group. On average, methylation at each of the hydroxyl positions results in a decrease of potency, ranked according to the following order of depression of $EC_{50}$ log units: 14-OH (2.12), 2-OH (1.67), 25-OH (1.09), 3-OH (1.06), and 22-OH (0.35). Significantly, however, 22-methylation of 5 out of 9 steroids, including 20E itself (4, $-\log EC_{50}$=8.20), results in a modest increase of potency. Multiple methylation is generally additive in its effect.

The engineered gene switch systems showed a somewhat different response in both potency and SAR details. Among the steroids tested on the wt-CfEcR, only 20E 22-O-ethyl ether 5 indicated a clear improvement in potency ($EC_{50}$=4.85 µM, RMFI=0.77) as compared to 20E, an essentially inactive steroid in this assay. In the E274V/V390I/Y410E mutant CfEcR gene-switch assay, 5 again constitutes a quite substantial improvement ($EC_{50}$=0.76 µM, RMFI=1.10) over parent 20E ($EC_{50}$=~20 µM, RMFI=0.12). Other 22-ethers, such as n-propyl and benzyl, experience improvements as well. Unexpectedly, both muristerone A and polypodine B are weaker in the CfEcR format gene switch assays compared to the $B_{II}$ assay.

Against the wt-CfEcR, PoA suffers loss of potency and efficacy upon hydroxyl methylation. However, for the E274V/V390I/Y410E mutant of CfEcR, the highly potent PoA ($EC_{50}$=0.10 µM, RMFI=0.52) loses much less potency and actually gains efficacy upon 22-methylation (18, $EC_{50}$=0.70 µM, RMFI=0.58) resulting in desirable potency, metabolism and permeability characteristics. This trend continues for the AaEcR and DmEcR in the same two-hybrid system in mouse 3T3 cells. With AaEcR, 18 more potent ($EC_{50}$=0.38 nM) than PoA at 1.10 nM; with DmECR, it is equipotent at ~66 nM. Likewise, in the *Drosophila*-based, VgEcR/RXR system, 18 is equal or possibly more potent than PoA and muristerone A ($EC_{50}$=533 nM/RMFI=1.5 vs. $EC_{50}$=641 nM/RMFI=1.5 and $EC_{50}$=851 nM/RMFI=1.3, respectively), and can therefore be regarded as the best ligand for this system. In short, PoA can be methylated at the 22-position yielding a structure with one less hydroxyl group while maintaining activity. Moreover, since the physicochemical properties of the O-methylated structure should be superior, it may have a greater potential for therapeutic use than would PoA itself. We have shown 22-O-alkyl (Me, Et, Pr) and 22-O-benzyl steroids retain or improve the inducing activity of their parent compounds.

ADME.

Ecdysteroid ethers have a favorable ADME profile. Several ADME properties—water solubility, Log P (M log P), blood-brain barrier (BBB) permeation, Caco-2 cell permeability, and human serum albumin (HSA) binding were calculated for illustrative steroid ethers and reference compounds (FIG. 7).

Solubility.

PoA and 20E calculated aqueous solubilities are consistent with experimentally obtained values (0.18 mg/mL and 6.7 mg/mL, respectively). Generally, solubility increases with the number of hydroxyl groups (e.g. muristerone A>20E>PoA); correspondingly, hydroxyl group capping generally decreases solubility. Noteworthy exceptions are the 20E 22-alkyl ethers. For example, solubilities of steroids 5 (20E 22-O-ethyl ether) and 7 (20E 22-O-allyl ether) are slightly higher than their parent compound with a free 20,22-diol. One explanation is intramolecular hydrogen-bonding of the 20,22-diol of 20E with consequent diminished solubilizing intermolecular hydrogen-bonding, as compared to the 22-alkyl analogues, which can participate only in the 20-OH donor/22-OH acceptor sense, and are therefore under more thermodynamic constraint to hydrogen-bond with the solvent. In like manner, 22-OH/25-OH intramolecular hydrogen-bonding effects may also be significant. Methylation at 0-22 of 20E disrupts the intramolecular H-bond in the 22-OH donor/25-OH acceptor sense, and therefore depression of water solubility of 20E 22-O-methyl ethers vs. 20E is less than that of PoA 22-O-methyl ethers vs. PoA, which lack a 25-OH and hence cannot form this intra-H-bond. As concerns diacylhydrazine 30, there are 3 orders of magnitude difference between the calculated (3.6 mg/mL) and observed aqueous solubility (6.2 µg/mL). Experimentally, diacylhydrazines are readily crystallized materials. Perhaps the solubility discrepancy reveals a physical behavior unaccounted for by the MI-QSAR model.

M log P Values.

Like aqueous solubility, M log P values trend positively with alkylation. Again, 22-alkylation is an exception; alkylation at this position can actually lower M log P, for the same intramolecular bonding reasons invoked for aqueous solubility trends. M log P overestimates experimental values: 20E log $D_{exp}$=0.01 (log $P_{calc}$=1.25); PoA log $D_{exp}$=1.95 (log $P_{calc}$=2.19).

Blood-Brain Barrier Partition.

A measure of the ability of a molecule to cross the BBB is the logarithm of the BBB partition coefficient (log BB), which is equal to $\log(C_{brain}/C_{blood})$, where $C_{brain}$ is the concentration of the compound in the brain and $C_{blood}$ is the concentration of the compound in the blood. According to published experimental BBB partition data, log(BB) values>0.3 are associated with compounds which are readily distributed to the brain, whereas log(BB) values<−1 indicate molecules which poorly distribute to the brain. Our ADME estimates indicate that 20E, PoA and muristerone A moderately distribute into the brain (−0.89<log(BB)<−0.35). On the other hand, O-alkyl ether steroids show an increased ability to cross the BBB, particularly PoA 2-methyl ether (16: log (BB)= 0.16) and PoA 22-methyl ether (18: log(BB)=0.23). The positive log(BB) value is desirable for potential central nervous system (CNS) therapeutic agents. Also, 20E O-alkyl ether analogues have higher computed log(BB) values as compared to 20E.

Permeability.

Caco-2 cell permeation coefficients ($P_{Caco-2}$) of some of the steroids were determined using an established Caco-2 cell permeation QSAR model. As is shown in FIG. 7, $P_{Caco-2}$ values increase progressively from muristerone A to 20E to PoA, in parallel with an increase in molecular lipophilicity (M log P values) and a decrease in aqueous solubility. PoA O-alkyl ether derivatives 16, 18 and 20 show equal or higher $P_{Caco-2}$ values (from $20 \times 10^{-6}$ to $29 \times 10^{-6}$ cm/sec) than the parent molecule PoA ($19 \times 10^{-6}$ cm/sec) and 20E O-alkyl ether derivatives 4, 5, 7, 10 and 14 also permeate Caco-2 cells equally or more readily ($14-24 \times 10^{-6}$ cm/sec) than the parent compound 20E ($16.3 \times 10^{-6}$ cm/sec). These results indicate improved oral bioavailability properties of O-ether ecdysteroid derivatives.

Measured Physicochemical and Absorption Properties of Ecdysteroids: A) Caco II Permeability Assay:

Confluent monolayers (n=2) of Caco-2 cells, 21 to 28 days old in Transwell® wells were dosed with the test steroid in each of the apical and basolateral sides at pH 7.4±0.2. Each side was sampled at 120 minutes to determine apical-basoleteral (A-B) and basolateral-apical permeability (B-A). Concentrations of test compound were measured using a generic LC/MS/MS method with a minimum 4 point calibration curve. A substance characterized by (Papp A→B)<1.0×10-6 cm/s is considered to have low permeability. Greater than this value is high permeability. A substance is considered to experience significant efflux if efflux>3.0 and (Papp B→A)>1.0× 10-6 cm/s; B) Plasma Protein Binding Assay: Dialysis wells (n=2), with one side of each dialysis well containing phosphate buffered saline (PBS) at pH 7.4 and the other side of the well containing mixed-gender human plasma, were dosed with the test steroid. After ca. 24 hours at 37° C., both the plasma and the buffer side of each well were sampled and analyzed using LC/MS/MS. These experiments were performed at Absorption Systems, Inc., and results are presented in Table 8.

TABLE 8

| Ecdysteroid | Caco II permeability ($10^{-6}$ cm/s) | | | Plasma protein binding (%) |
| --- | --- | --- | --- | --- |
| | A-B | B-A | Efflux | |
| 20-Hydroxyecdysone | 0.11 | 0.39 | 3.5 | 9.2 |
| Ponasterone A | 2.26 | 13.9 | 6.2 | 57.4 |

Plasma Protein Binding.

HSA binding affinity is an important pharmacokinetic property considered in drug discovery and development. HSA binding allows solubilization of hydrophobic molecules in the circulatory system. The binding strength of a compound to serum albumin is one of the main factors determining the distribution of the compound to target tissues and, therefore, its bioavailability. As shown in FIG. 7, the ecdysteroids show similar HSA binding affinities, ranging from $2.1 \times 10^{-4}$ to $3.8 \times 10^{-4}$ (Ka values). The lowest HSA binding compound in the set is 20E 22-ethyl ether (5), which also has the lowest M log P value of the ethers in the set and the highest calculated aqueous solubility. The highest HSA binding compound is PoA 3,22-dimethyl ether (20), which also has the highest M log P value of the ethers in the set and is in the lower range of calculated aqueous solubility for ecdysteroids. Thus, there is a general correlation between ecdysteroid HSA binding and compound hydrophobicity and aqueous solubility.

Metabolism and Excretion.

The estimated half-life for 20E in human is 9 hours. Known metabolites in mice, rats and humans include products of dehydroxylation, reduction of the B-ring, epimerisation at C-3 and 20,22-diol cleavage. From first principles, as well as precedent examples of alkylative capping enhancing metabolic stability, ecdysteroid alkyl ethers should be more resilient than the corresponding non-ethers toward dehydroxylation, oxidative cleavage, and conjugation reactions; O-dealkylation steps would have to occur first.

OH capping is an effective way to improve physicochemical properties and especially the metabolism of ecdysteroids. An overall balance is achieved through alkylation: properties in excess (i.e., water solubility and hydrophilicity) are modulated in order to enhance properties that are deficient (metabolic instability, clearance). This is achieved without sacrificing potency.

Semi-Synthetic Ecdysteroids as Drugs.

Steroids, including ecdysteroids represent gene switch ligands additional to diacylhydrazines, which are another useful chemotype in EcR-based switch systems.

The alkylation strategy disclosed herein modulates ADME properties that impact bioavailability and drug delivery parameters. 22-O-alkylation represents one modification. Such alkylation provides improved steroidal actuators for switch-activated gene therapy. By methylation of specific ecdysteroid hydroxyl groups, we have established improved pharmacologically-relevant physicochemical properties of ecdysteroids while retaining or improving potency towards selected EcRs.

Addition of hydroxyl groups at the 2, 3, 14, 20, and 22 positions incrementally increases potency while hydroxylation at the 25 position decreases potency. Nevertheless, several outlier ligand/EcR combinations, such as cyasterone activation of E274V/V390I/Y410E mutant-CfEcR and canescensterone activation of *Bemisia argentifolii* BaEcR, exhibit an inversion of relative potency and illustrate directional design for orthogonal gene switches. The potency inversion between these two ligand/receptor pairs may be explained by steroid-tail contact residues V411 and M502 in E274V/V390I/Y410E mutant-CfEcR corresponding to two threonines in BaEcR. In general, the lepidopteran and non-lepidopteran classes distinguish themselves from one another by the V to T/N/S alteration at the CfEcR-V411 position. Another potency inversion is also observed with cyasterone operating on the E274V/V390I/Y410E mutant of CfEcR and polypodine B activating *Aedes aegypti* (Aa) EcR.

EXAMPLE TWO

We assayed a set of forty-two steroids against a group of ten EcRs representing nine arthropod species in a common two-hybrid gene switch format; data from the $B_{II}$ assay and the VGECR/RXR gene switch was interpreted in context. Trends and also unusual potency inversions were tabulated. The EcR sequences were aligned, contact residues from available crystal structures (LBDs from the lepidopteran *Heliothis virescens* [Hv], the hemipteran *Bemisia tabaci* [Bt] and the beetle *Tribolium castaneum* [Tc]) were annotated, and potency correlations between substituent changes on the ligands and residue patterns on the receptors were notated. SAR outliers offer revealing ligands in a ligand dataset. Potency inversions are identified for the construction of orthogonal gene switches.

We have identified new nanomolar and subnanomolar steroid/EcR combination(s). We also describe more extensive EcR screening data on several rare steroids. EcR sequences in the two-hybrid gene-switch format are evaluated for responsiveness, basal activity, and dynamic range. Two unexpected steroid/EcR orthogonalities are identified and assessed in view of EcR LBD sequence.

Materials & Methods

Isolation, Purification, and Synthesis of Steroids.

Semi-synthetic steroids 20E 2-methyl ether, 20E 3-methyl ether, 20E 22-methyl ether, 20E 2,22-dimethyl ether, 20E 3,33-dimethyl ether, 20E 2,3,14,22-tetramethyl ether, 20-hydroxyecdysone 22-O-pyrrole carboxylate, and turkesterone-11 alpha propionate, turkesterone-11 alpha hexanoate, turkesterone-11 alpha decanoate were prepared from 20E or turkesterone. The remaining steroids were isolated from plant materials, except for ponasterone A which was also synthesised from 20-hydroxyecdysone. Muristerone A which was purchased by AG Scientific Inc (San Diego, Calif.). The following compounds were generously supplied by other researchers: 2-deoxyecdysone, ecdysone, 2-deoxy-20-hydroxyecdysone, and cyasterone (Prof. René Lafont), taxisterone, polypodine B, ajugasterone C, (25S)-inokosterone, (25R)-inokosterone, makisterone A, makisterone C, carthamosterone, intergristerone A (Dr. Juraj Harmatha), 20-hydroxyecdysone (Dr. Vladimir Volodin), turkesterone (Prof. Zyadilla Saatov) and canescensterone (Prof. Apichart Suksamram). Reagents and solvents used for the synthesis/purification were purchased from Fisher Scientific and Sigma-Aldrich. Water for HPLC was deionized to a degree of purity of 17 W.

Purification of individual steroids was carried out by HPLC, which involved one or more of the following methods: (a) semi-preparative $C_{18}$-HPLC (Phenomenex Sphereclone ODS2; 250×10 mm, 5 μm, flow-rate=2 mL/min) and (b) preparative $C_{18}$-HPLC (Phenomenex Sphereclone ODS2; 250×21.20 mm, 5 μm, flow-rate=5 mL/min), eluted isocratically with suitable $CH_3OH/H_2O$ mixtures; (c) semi-preparative silica column (Kinesis Zorbax Sil; 250×9.4 mm, 5 μm, flow-rate=2 mL/min), eluted isocratically with $CH_2Cl_2$:2-PrOH:$H_2O$ 160:30:1.5 or 125:30:2.0, v/v/v.

All samples have been purified to at least 98% with RP-HPLC and/or NP(diol)-HPLC. Compound purity was verified by HPLC interfaced with a diode-array detector (DAD) on a Gilson 170 system (Anachem Limited, Luton, U.K.), using two different reversed-phase columns (Phenomenex Sphereclone $C_{18}$ and $C_6$, 5 μm, 150×4.60 mm; Phenomenex, Macclesfield, U.K.) subjected to a linear gradient from 30% to 100% $CH_3OH$ in $H_2O$ over 25 min, followed by 10 min at isocratic 100% $CH_3OH$, and one normal-phase column (Kinesis-GRACE Apex II Diol, 5 μm, 150×4.60 mm) subjected to a linear gradient from 2% to 10%, or 4% to 10%, $CH_3OH$ in $CH_2Cl_2$ all at a flow-rate of 1 mL/min and wave-lengths (λ) of 242 nm and 300 mm.

Product quantification was carried out by UV spectroscopy on a Shimadzu UV-2401PC (Shimadzu GB, Milton Keynes, U.K.) for compounds containing either the 14α-hydroxy-7-en-6-one moiety ($\lambda_{max}$=242 nm, molar extinction coefficient (ε)=12,400 $Lmol^{-1}$ $cm^{-1}$) or the 14α-hydroxy-7,9(11)-dien-6-one moiety ($\lambda_{max}$=299 nm, E=14,190 $Lmol^{-1}$ $cm^{-1}$). Concentrations were calculated according to the Lambert-Beer equation.

TABLE 9

| EcR | Order | Common Name | Scientific Name | Reference | Accession Number |
|---|---|---|---|---|---|
| BmEcR | lepidoptera | Silkworm | *Bombyx mori* | Swevers et al., 1995 | AAA87341 |
| MsEcR | lepidoptera | Tobacco hornworm | *Manduca sexta* | Fujiwara et al., 1995 | AAA86699 |
| CfEcR | lepidoptera | Spruce budworm | *Choristoneura fumiferana* | Kothapalli et al., 1995 | AAC36491 |
| mutant-CfEcR (E274V/V390I/Y410E) | lepidoptera | Spruce budworm | *Choristoneura fumiferana* | Palli and Kumar | — |
| DmEcR | diptera | Fruit fly | *Drosophila melanogaster* | Koelle et al., 1991 | AAA28498 |
| VGECR/RXR | diptera | Fruit fly | *Drosophila melanogaster* | Saez et al., | AAG02187 |
| AaEcR | diptera | Yellow fever mosquito | *Aedes aegypti* | Cho et al., 1995 | AAA87394 |
| AmaEcR | acarina (arachnida) | Ixodid tick | *Amblyomma americanum* | Guo et al., 1997 | AAB94567 |
| BaEcR | homoptera | Silverleaf whitefly | *Bemisia argentifolii* | Zhang, et. al. 2003 | DD156938[a] |
| NcEcR | homoptera | Leaf hopper | *Nephotettix cincticeps* | Palli, et. al., 2002 | AX407022[a] |

TABLE 9-continued

| EcR | Order | Common Name | Scientific Name | Reference | Accession Number |
|---|---|---|---|---|---|
| TmEcR | coleoptera | Yellow meal worm | *Tenebrio molitor* | Mouillet et al., 1997 | CAA72296 |

[a]nucleotide sequence

Cellular Gene-Switch Assays—*Drosophila* $B_{II}$ Cell Morphology.

The *D. melanogaster* $B_{II}$ cell line bioassay was used to test the activity of potential EcR ligands. Assays were performed in quadruplicate. Stock solutions ($10^{-3}$ M to $10^{-10}$ M) in methanol were prepared for each of the test compounds. Aliquots (20 µL) of each dilution were transferred to wells of a microtitre plate and solvent was evaporated. Wells were added 200 µL of cell suspension at approximately $2 \times 10^5$ cells/mL medium and the covered plate was incubated in a humid environment at 25° C. for 7 days. Cellular response as a function of steroid concentration was measured turbidometrically at 405 nm Cellular Gene-Switch Assays—Engineered EcR:USP/RXR Systems.

Cellular gene-switch assays were performed by transfecting the following constructs in mouse embryonic fibroblast cells (NIH3T3). The D, E and F domains from EcRs of Table 9 were fused to GAL4-DBD and placed under the control of the CMV promoter. Primers and cloning steps are described above. A chimeric RXR from *Homo sapiens* RXRβ and *Locusta migratoria* RXR fused to VP16-AD and under the control of an SV40e promoter. The inducible luciferase reporter plasmid, pFRLuc, (Stratagene Cloning Systems, La Jolla, Calif., USA) contains five copies of the GAL4 response element and a synthetic minimal promoter. The VgEcR/RXR gene switch system, which employs a hybrid EcR bearing a VP16 activation domain and a 3-residue mutated DBD that recognizes an asymmetric EcR- and glucocorticoid receptor response element, was obtained from Invitrogen Inc. (Carlsbad, Calif., USA), and employed in an analogous manner by transient transfection in NIH3T3 cells.

NIH3T3 cells (these NIH3T3 cells are from a different clonal population than the NIH3T3 cells of EXAMPLE ONE) were maintained at 37° C. and 5% $CO_2$ in Dulbecco's modified Eagle's medium (DMEM) supplemented with 10% Bovine Calf Serum, both obtained from Mediatech, Inc., Manassas, Va. Cells were plated in a 96-well plate at a density of 2,500 cells/well in 50 µL of growth medium. The following day cells were first treated with 35 µL of serum-free DMEM containing dimethyl sulfoxide (DMSO; control) or a DMSO solution containing ligand. Cells were then transfected with 15 µl of serum-free DMEM containing 0.04 µg of EcR construct, 0.04 µg of RXR construct, and 0.16 µg of luciferase reporter construct per well, using SuperFect transfection reagent (Qiagen Inc., Valencia, Calif., USA) according to the manufacturer's instructions. Ligands were tested at 8 doses from 0.01-33 µM and the final DMSO concentration was 0.33% in both control and treatment wells. After a 48 hour post-treatment and transfection incubation, the cells were assayed for luciferase activity using the Bright-Glo™ Luciferase Assay System (Promega Corporation, Madison, Wis., USA) following the manufacturer's instructions.

Protein sequences were obtained from Pubmed. Where sequences were available as nucleotide only (Ba and Nc), translation was performed using the EBI Transeq program (http://www.ebi.ac.uk/emboss/transeq/). Sequence alignment and phylogeny estimation were obtained using ClustalW2 (available on the worldwide web at ebi.ac.uk/Tools/clustalw2/). In cases where more than one EcR variant was available, preliminary alignments using ClustalW were performed to demonstrate that residue variations are located outside of the LBD.

Molecular modeling was performed using SYBYL 7.1 and 7.3. Cyasterone/E274V/V390I/Y410E mutant-CfEcR//canescensterone/BaEcR comparison: HvEcR with bound PoA (PDB: 1R1K) and BtEcR with bound PoA (LBD identical to BaEcR, PDB: 1Z5X) were aligned by homology in Sybyl 7.1, giving a weighted RMS distance=1.22, based on alignment of C-alpha atoms. Residues within a 6.5 Å heavy atom radius were identified. CfEcR V390 and Y410 were mutated to I and E, respectively. All other residues were removed from consideration. Cyasterone, docked in E274V/V390I/Y410E mutant-CfEcR, and canescensterone, docked in BaEcR, were manually modified from PoA in each crystal structure, optionally with side-chain minimization (Tripos Force Field with Gasteiger-Hückel charges), but no perturbation of the steroid ring system, in an effort to maximize receptor fit. For 24S-canescensterone, the M301 C—C—S—C torsion of BaEcR was moved 180° to avoid steric clash with the canescensterone pyrrole carbonyl, a reasonable adjustment considering that a) M301 is on H7 and points externally towards H11, b) this movement creates no other conflicts, and c) precedent for a methionine shift is found in the BYI06830:HvEcR crystal structure (PBD: 1R20). For 24R-canescensterone, the M301 C—C—S—C torsion of BaEcR was moved 10° to avoid steric clash with the canescensterone pyrrole carbonyl. Also, the steroid C23-24 bond torsion was adjusted 10° to attain a better pyrrole ring position. In summary, only few and plausible adjustments of the contact residues or steroid side chain were needed to accommodate cyasterone and canescensterone in their responsive receptors. Corresponding binding pocket residues of AaEcR and BtEcR were then compared for identity and pose. Cyasterone/E274V/V390I/Y410E mutant-CfEcR/polypodine B/AaEcR comparison: Cyasterone was used as above. Polypodine B was modified from PoA in the PoA:BtEcR complex. AaEcR residues relevant to orthogonal ligand recognition were identified in the following way. 6.5 Å binding pocket residues in the PoA:BtEcR crystal structure (PDB 1Z5X) were identified and the BtEcR sequence was aligned with AaEcR. Among these binding pocket residues, five differed between the two receptors: Bt-H200/Aa-Q353, Bt-T287/Aa-N441, Bt-M389/Aa-Q545, Bt-T393/Aa-M549, and Bt-V404/Aa-L560. Since each of these five are identical with their alignment counterparts in E274V/V390I/Y410E mutant-CfEcR, these five residues were eliminated as contributing to orthogonality. Additional residues between the two receptors that were both identical and similar in pose were also eliminated. BYI06830/Canescensterone overlay: HvEcR bound with PoA (PDB 1R1K) and BYI06830 (PDB 1R20) were aligned by homology. PoA was replaced with canescensterone as obtained above. The following 3D models were generated (data not shown): A. Superimposition of cyasterone (carbon atoms in cyan, oxygen atoms in red) docked in VY-CfEcR (green) with 24S-canescensterone (carbon atoms in yellow, oxygen atoms in red, nitrogen atoms in blue, hydrogen atoms in white) docked in BaEcR (orange). VY-CfEcR residues are derived from the PoA-bound HvEcR crystal structure (PDB code: 1R1K), except for HvEcR-V395 which was mutated to VY-CfEcR-I390, and HvEcR-Y415 which was mutated to VY-CfEcR-E410. Only residues within 6.5 Å (heavy atom distances) of the ligand and which are high interest or differ in identity or substantially in conformation between the two EcRs are depicted. Blue labels refer to VY-CfEcR residues and brown labels refer to BaEcR residues. Image is a view towards the beta-sheet with portions of helices H3 and H4 in the foreground. Canescensterone is depicted with a surface colored by electrostatic potential. Selected hydrogen-bonds between 24S-canescensterone and BaEcR residues (T337, T426) are indicated by dashed red lines. Cyasterone does not participate in analogous H-bond interactions. B. Superimposition of cyasterone (cyan) docked in VY-CfEcR (green) with polypodine B (yellow) docked in AaEcR (orange). Polypodine B is depicted with a surface colored by electrostatic potential. C. Superimposition of 24-S-canescensterone (yellow) as docked in HvEcR analogously to PoA:HvEcR crystal structure and the diacylhydrazine BY106830 (cyan) as found in the HvEcR crystal structure.

Results

The screening set of forty-two steroids is listed in FIGS. 9, 10 and 11. The largest subset of steroids vary in hydroxylation state at the 2-, 3-, 5-, 11-, 14-, 20-, 22- and 25-positions and methylation at the 2-, 3-, 14-, and 22-positions (FIG. 9). A second subset of steroids comprises a selection of side-chain modifications, including desaturation, alkylation, and chain-ring fusions (FIG. 10). The third and final subset contains steroids with unusual structural variations and one brassinosteroid (iso-homobrassinolide) (FIG. 11).

Gene switch systems constructed from each of ten different EcRs (FIG. 12) and using a two-hybrid format—GAL4 DBD fused upstream to EcR and VP16 activation domain fused upstream to an RXR-USP chimera—were transiently transfected into murine NIH 3T3 cells using pM and pVP16 plasmids, respectively. Luciferase was employed as the reporter gene, transiently transected with vector pFRLUC. Dose response curves were obtained for the forty-two member steroid set. $EC_{50}$ values were derived and are depicted in FIG. 13 (lepidopterans) and FIG. 14 (non-lepidopterans). A secondary steroid gene switch $EC_{50}$ dataset, principally comprising data from a subset of six steroid ethers but also from several natural steroids in the primary set, was also recorded for the same switch systems in a 3T3 cell line. These data also include assay results using the VgEcR/RXR system, shown in FIG. 15 and FIG. 16.

Efficacy was measured in three ways. The first method is relative light units (RLU) recorded directly from the luminometer. The second method is the ratio of RLUs at a test ligand concentration to the background RLUs, i.e., the fold induction (FI). The third method is the ratio of the maximum FI observed for a given ligand at any concentration to the maximum FI observed for the diacylhydrazine N-(2-ethyl-3-methoxybenzoyl)-N'-(3,5-dimethylbenzoyl)-N'-tert-butyl-hydrazine. These values are entered in FIGS. 13-16 as RMFI (relative maximum fold induction). As an indication of the basal expression for each switch system, background RLUs are entered in the last row of each table.

The combination of PoA/NcEcR showed an $EC_{50}$=0.3 nM (RMFI=1). Furthermore, PoA activating BmEcR showed an $EC_{50}$=0.11 μM, RMFI=0.98, diacylhydrazine reference FI=1776, background FI=3. And PoA activating E274V/V390I/Y410E mutant-CfEcR showed an $EC_{50}$=0.11 μM, RMFI=0.52, diacylhydrazine reference FI=4393, background FI=2. However, 20E showed virtually no response toward CfEcR.

An overview of steroid-potency/receptor-responsiveness is given in the stacked line diagram of FIG. 17, which depicts the $-\log(EC_{50})$ of selected steroids against each EcR type ordered by phylogeny. Crossovers indicate a potency inversion between two ligand-receptor pairs on opposite sides of the crossover. For example, cyasterone/E274V/V390I/Y410E mutant-CfEcR and canescensterone/BaEcR; and cyasterone/E274V/V390I/Y410E mutant-CfEcR and polypodine B/AaEcR. The dose-response curves for these two systems are depicted in FIG. 18 and FIG. 19. A graph of $-\log(EC_{50})$ vs. $-\log(EC_{50})$ for the E274V/V390I/Y410E mutant-CfEcR/BaEcR pair is depicted in FIG. 20.

The collected screening set represents structural and chemical diversity, including variations in hydroxylation number and position, the saturated linear $C_8$ side-chain, the cis-A/B-ring junction and the 7-en-6-one chromophore. The plant steroid, canescensterone, bears a pyrrole 2-carboxylate group attached to $C_{24}$. This compound has high biological activity towards the *Drosophila* $B_{II}$ cell line ($EC_{50}=5.3\times10^{-10}$ M). In this bioassay, all the tested steroids show some activity, with $EC_{50}$ spanning almost 6 order of magnitude (FIG. 14).

A series of methyl ethers of 20E and PoA were screened against multiple receptors (FIGS. 15 and 16).

Both PoA and 20E are more potent for the non-lepidopteran receptors than for the lepidopterans. The lepidopteran E274V/V390I/Y410E mutant-CfEcR also bears a modified region for the ecdysteroid tail due to the Y410E mutation. This, together with the V390I mutation, renders E274V/V390I/Y410E mutant-CfEcR more like non-lepidopteran EcRs.

PoA, muristerone A, stachysterone C, and isostachysterone C are active steroids across the tested set of EcRs (FIGS. 13 and 14). All have hydrophobic tails. Whereas cyasterone is somewhat selective for lepidopteran EcRs, canescensterone is selective for non-lepidopteran EcRs. Likewise, activity of ajugasterone C is higher in non-lepidopteran species. Except for BaEcR, canescensterone has generally weak (AaEcR and AmaEcR) or null RMFI values.

Six semi-synthetic steroid ethers along with selected natural ecdysteroids were tested in an alternative 3T3 fibroblast cell stock (FIGS. 15 and 16). In general, the following observations can be made: for E274V/V390I/Y410E mutant-CfEcR with the 20E 3-O-methyl ether, potency is maintained or even gained. Other ethers lose potency, such as, MsEcR with 20E 3-methyl ether, 20E 22-methyl ether, and 20E 3,22-O-dimethyl ethers.

Steroid potency and efficacy are comparable to diacylhydrazine (N-(2-ethyl-3-methoxybenzoyl)-N'-(3,5-dimethylbenzoyl)-N'-tert-butylhydrazine) in engineered EcR. For example, both PoA and diacylhydrazine are highly potent, single digit nM activators of AaEcR. However, PoA is most potent toward the Nc, Aa, and Ama EcRs (0.3-2 nM), whereas the diacylhydrazine is more potent with the lepidopteran receptors (3-20 nM). Ponasterone shows submicromolar potency toward all EcRs tested, but the diacylhydrazine has micromolar with BaEcR (6 uM). Except for AmaEcR, BaEcR, and TmEcR, the diacylhydrazine is somewhat more efficacious than PoA. Among the receptors studied, E274V/V390I/Y410E mutant-CfEcR and the other lepidopteran EcRs are the best optimized while AmaEcR and TmEcR are less optimized as gene switch systems, due to overall fold induction and background.

Multi-Ligand/Receptor Interactions.

The E274V/V390I/Y410E mutant-CfEcR//BaEcR pair is moderately correlated ($R^2=0.6$, FIG. 4). Correspondingly the stacked line plot (FIG. 17) of receptor $-\log(EC_{50})$, together with consideration of relative efficacy (RMFI), shows potency inversion between cyasterone (E274V/V390I/Y410E mutant-CfEcR>BaEcR) and canescensterone (BaEcR>E274V/V390I/Y410E mutant-CfEcR). Dose-response curves (FIG. 18) illustrate orthogonality.

Potency inversion occurs with the cyasterone/E274V/V390I/Y410E mutant-CfEcR/polypodine B/AaEcR duplex (FIG. 17). The E274V/V390I/Y410E mutant-CfEcR//AaEcR pair is also moderately correlated ($R^2=0.6$). Examination of the dose-response curves (FIG. 19) shows that the $EC_{50}$ margin is narrower than with the cyasterone/E274V/V390I/Y410E mutant-CfEcR//canescensterone/BaEcR system.

Gene Switch Applications.

Ligand inducible gene expression systems are useful for functional genomics, drug discovery, biotherapeutic protein production, trait expression in transgenic agriculture and animals, systems and synthetic biology; cell engineering, and gene therapy.

Feasibility has been demonstrated for at least two steroid ligands: PoA and muristerone A. Among non-natural, non-steroidal compounds, potency has been demonstrated for the amidoketones and tetrahydroquinoline chemotypes. In the diacylhydrazine family of ligands, some can activate engineered EcR-based switches at sub-nanomolar concentrations. Steroids, by contrast, have free hydroxyl groups and are metabolically fragile. Several of these hydroxyl groups are refashioned into more ADME-suitable pharmacophoric elements.

Biomedicine needs multiplex switches. In cancer simultaneous control of several deleterious gene functions can be important in disease suppression. To be practical, multiplex switches must be robust and as simple as engineering parameters will allow. Among EcR-based switches, the basic components of a steroid/diacylhydrazine and a THQ/diacylhydrazine duplex have been reported (Kumar et al. PNAS 2002 99:14710-15; Kumar et al. J Biol Chem 2004 279:27211-18). The cyastereone/canescensterone and cyasterone/polypodine B systems disclosed here represent steroid based orthogonal gene switches.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A compound having the formula:

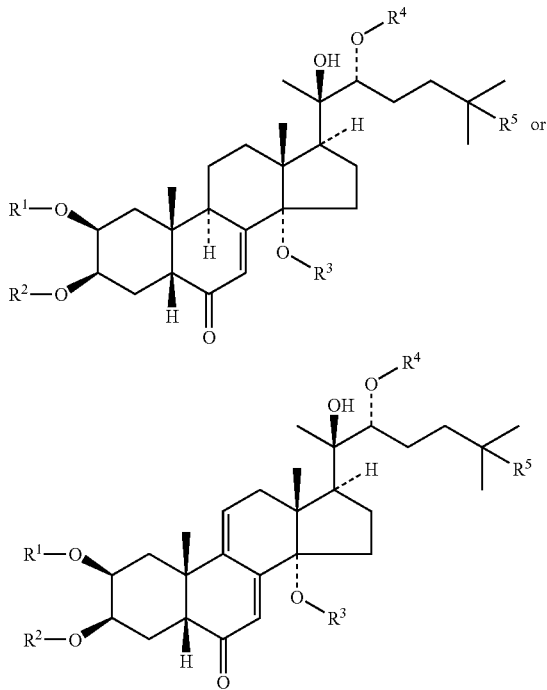

wherein $R^1$, $R^2$, $R^3$, and $R^4$ are:

a) H, $(C_1-C_6)$alkyl; $(C_1-C_6)$haloalkyl; $(C_1-C_6)$cyanoalkyl; $(C_1-C_6)$hydroxyalkyl; $(C_{1-4})$alkoxy$(C_1-C_6)$alkyl; $(C_2-C_6)$alkenyl optionally substituted with halo, cyano, hydroxyl, or $(C_1-C_4)$alkyl; $(C_2-C_6)$alkynyl optionally substituted with halo, cyano, hydroxyl, or $(C_1-C_4)$alkyl; $(C_3-C_5)$cycloalkyl optionally substituted with halo, cyano, hydroxyl, or $(C_1-C_4)$alkyl; or b) unsubstituted or substituted benzyl wherein the substituents are independently 1 to 5 H, halo, or $(C_1-C_6)$alkyl; and $R^5$ is H; OH; F; or Cl;

provided that:

when $R^1$, $R^2$, $R^3$, and $R^4$ are isopropyl, then $R^5$ is not hydroxyl;

when $R^5$ is H, hydroxyl, methoxy, or fluoro, then, at least one of $R^1$, $R^2$, $R^3$, and $R^4$ is not H;

when only one of $R^1$, $R^2$, $R^3$, and $R^4$ is methyl, and $R^5$ is H or hydroxyl, then the remainder of $R^1$, $R^2$, $R^3$, and $R^4$ are not H;

when both $R^4$ and one of $R^1$, $R^2$, and $R^3$ are methyl, then $R^5$ is neither H nor hydroxyl;

when $R^1$, $R^2$, $R^3$, and $R^4$ are all methyl, then $R^5$ is not hydroxyl;

when $R^1$, $R^2$, and $R^3$ are all H and $R^5$ is hydroxyl, then $R^4$ is not ethyl, n-propyl, n-butyl, allyl, or benzyl.

2. A composition comprising one or more compounds of claim 1 and a carrier.

3. A recombinant gene switch composition comprising:
at least one gene switch comprising an ecdysone receptor ligand binding domain; and
at least one activating ligand,
wherein said activating ligand is a compound of claim 1.

4. The recombinant gene switch composition of claim 3, wherein said composition comprises at least two gene switches.

5. The recombinant gene switch composition of claim 4, wherein one of said gene switches is activated by a non-steroidal ligand.

6. The recombinant gene switch composition of claim 5, wherein said non-steroidal ligand is selected from the group consisting of diacylhydrazine, amidoketone, and oxadiazoline.

7. The recombinant gene switch composition of claim 4, wherein each gene switch is encoded by one or more nucleic acids present in the same vector polynucleotide.

8. The recombinant gene switch composition of claim 4, wherein each gene switch forms heterodimer receptor complex.

9. The recombinant gene switch composition of claim 8, wherein said heterodimer receptor complex of each gene switch has a common component.

10. The recombinant gene switch composition of claim 9, wherein said common component comprises a retinoid X receptor ligand binding domain or a retinoid X receptor/ultraspiracle protein chimeric ligand binding domain.

11. A composition comprising a plurality of individually operable recombinant gene switches, wherein each individually operable recombinant gene switch comprises:
a first recombinant cassette comprising first polynucleotide encoding a first polypeptide comprising:
a DNA-binding domain that recognizes a response element operatively linked with a gene of interest whose expression is to be modulated;
an ecdysone receptor ligand binding domain, a mutant ecdysone receptor ligand binding domain, a V390I/Y410E mutant of the *Choristoneura fumiferana* ecdysone receptor ligand binding domain, or a E274V/V390I/Y410E mutant of the *Choristoneura fumiferana* ecdysone receptor ligand binding domain;
a second recombinant cassette comprising:
a response element capable of binding to said DNA binding domain;
a promoter that is activated by the transactivation domain; and
a gene of interest;
wherein the composition comprises a plurality of ligands, wherein at least one ligand is
a compound of claim 1.

12. A composition comprising a plurality of individually operable recombinant gene switches comprising an ecdysone receptor ligand binding domain, each gene switch being controlled by a different ligand, wherein each individually operable gene switch comprises:
A) one or more gene expression cassette(s) comprising:
a first polynucleotide encoding a first polypeptide comprising:
a transactivation domain;
a nuclear receptor ligand binding domain;
a second polynucleotide encoding a second polypeptide comprising:
a DNA-binding domain that recognizes a response element operatively linked with a gene of interest whose expression is to be modulated;
a nuclear receptor ligand binding domain;
a third polynucleotide comprising:
a response element capable of binding to said DNA binding domain;

a promoter operably linked to the response element; and
a gene of interest;
B) a ligand, wherein the ligand is
a compound of claim 1.

13. The composition of claim 12, wherein said composition comprises at least two gene switches.

14. The composition of claim 13, wherein one of said gene switches is activated by a non-steroidal ligand.

15. The composition of claim 14, wherein said non-steroidal ligand is selected from the group consisting of diacylhydrazine, amidoketone, and oxadiazoline.

16. The composition of claim 12, wherein each gene switch is encoded by one or more nucleic acids present in the same vector polynucleotide.

17. The composition of claim 12, wherein each gene switch forms a heterodimer receptor complex.

18. The composition of claim 17, wherein said heterodimer receptor complex of each gene switch has a common component.

19. The composition of claim 18, wherein the common component comprises a retinoid X receptor ligand binding domain or a retinoid X receptor/ultraspiracle protein chimeric ligand binding domain.

20. The composition of claim 12, wherein each individually operable gene switch controls a different gene of interest.

21. The composition of claim 12, wherein one gene of interest is capable of killing a cell.

22. The composition of claim 21, wherein said gene of interest capable of killing a cell is a toxin.

23. The composition of claim 12, wherein one gene of interest is a therapeutic gene of interest.

24. The composition of claim 12, wherein one gene of interest is a cytokine.

25. The composition of claim 12, wherein one or more nuclear receptor ligand binding domains is a Group H nuclear receptor ligand binding domain.

26. The composition of claim 12, wherein one or more nuclear receptor ligand binding domains is an ultraspiracle protein ligand binding domain, a retinoid X receptor ligand binding domain, a retinoid X receptor homolog ligand binding domain, or a chimera of a retinoid X receptor ligand binding domain.

27. The composition of claim 12, wherein one or more nuclear receptor ligand binding domains is a Group H nuclear receptor ligand binding domain; and wherein one or more nuclear receptor ligand binding domains is an ultraspiracle protein ligand binding domain, a retinoid X receptor ligand binding domain, a retinoid X receptor homolog ligand binding domain, or a chimera of a retinoid X receptor ligand binding domain.

28. The composition of claim 27, wherein the Group H nuclear receptor ligand binding domain is from an ecdysone receptor, a mutant ecdysone receptor, a lepidopteran ecdysone receptor, a mutant lepideopteran ecdysone receptor, a *Choristoneura fumiferana* ecdysone receptor, a V390I/Y410E mutant of the *Choristoneura fumiferana* ecdysone receptor, or a E274V/V390I/Y410E mutant of the *Choristoneura fumiferana* ecdysone receptor.

29. A method of activating a recombinant gene switch system comprising an ecdysone ligand binding domain by administering an effective amount of a ligand, wherein said ligand is a compound of claim 1, wherein said recombinant gene switch composition is responsive to said ligand.

30. A method of modulating the expression of a gene of interest in a host cell, wherein the host cell comprises a first recombinant cassette, wherein the first recombinant cassette comprises:
a first polynucleotide encoding one or more polypeptides collectively comprising:
a transactivation domain;
a DNA-binding domain that recognizes a response element operatively linked with a gene of interest whose expression is to be modulated;
a nuclear receptor ligand binding domain, a Group H nuclear receptor ligand binding domain, an ecdysone receptor ligand binding domain, a substitution mutant of the *Choristoneura fumiferana* ecdysone receptor ligand binding domain, a V390I/Y410E mutant of the *Choristoneura fumiferana* ecdysone receptor ligand binding domain, or a E274V/V390I/Y410E mutant of the *Choristoneura fumiferana* ecdysone receptor ligand binding domain; and
a second recombinant cassette comprising:
a response element capable of binding to said DNA binding domain;
a promoter operatively linked to the response element; and
a gene of interest;
the method comprising contacting said host cell with a compound of claim 1.

31. A method of modulating the expression of a gene of interest in a host cell, wherein the host cell includes:
a first recombinant cassette comprising a first polynucleotide encoding a first polypeptide comprising:
a transactivation domain;
a Group H nuclear receptor ligand binding domain;
a second recombinant cassette comprising a second polynucleotide encoding a second polypeptide comprising:
a DNA-binding domain that recognizes a response element operatively linked with a gene of interest whose expression is to be modulated;
a Group H nuclear receptor ligand binding domain, an ecdysone receptor ligand binding domain, a substitution mutant of an ecdysone receptor ligand binding domain, a V390I/Y410E mutant of the *Choristoneura fumiferana* ecdysone receptor ligand binding domain, or a E274V/V390I/Y410E mutant of the *Choristoneura fumiferana* ecdysone receptor ligand binding domain;
a third recombinant cassette comprising:
a response element capable of binding to said DNA binding domain;
a promoter operably linked to the response element; and
a gene of interest;
the method comprising contacting said host cell with a compound of claim 1.

* * * * *

UNITED STATES PATENT AND TRADEMARK OFFICE
CERTIFICATE OF CORRECTION

| | | |
|---|---|---|
| PATENT NO. | : 8,536,354 B2 | Page 1 of 1 |
| APPLICATION NO. | : 12/404943 | |
| DATED | : September 17, 2013 | |
| INVENTOR(S) | : Hormann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 470 days.

Signed and Sealed this
Twenty-fourth Day of February, 2015

Michelle K. Lee
*Deputy Director of the United States Patent and Trademark Office*